(12) United States Patent
Müller et al.

(10) Patent No.: US 6,746,989 B1
(45) Date of Patent: Jun. 8, 2004

(54) SUBSTITUTED BENZOYLPYRAZOLES AS HERBICIDES

(75) Inventors: Klaus-Helmut Müller, Düsseldorf (DE); Stefan Lehr, Langenfeld (DE); Otto Schallner, Monheim (DE); Hans-Georg Schwarz, Langenfeld (DE); Heinz-Jürgen Wroblowsky, Langenfeld (DE); Mark Wilhelm Drewes, Langenfeld (DE); Dieter Feucht, Monheim (DE); Rolf Pontzen, Leichlingen (DE); Ingo Wetcholowsky, Cond. Estancia Marambaia (BR)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/937,631

(22) PCT Filed: Mar. 15, 2000

(86) PCT No.: PCT/EP00/02292
§ 371 (c)(1),
(2), (4) Date: Sep. 26, 2001

(87) PCT Pub. No.: WO00/58306
PCT Pub. Date: Oct. 5, 2000

(30) Foreign Application Priority Data

Mar. 27, 1999 (DE) ......................... 199 14 140

(51) Int. Cl.$^7$ ..................... A01N 43/647; C07D 271/06
(52) U.S. Cl. ..................... 504/261; 504/265; 504/270; 504/271; 504/273; 504/277; 504/278; 504/282; 548/132; 548/213; 548/230; 548/229; 548/227; 548/244; 548/243; 548/263.2; 548/263.8; 548/312.4; 548/364.1; 548/365.1
(58) Field of Search ..................... 504/261, 265, 504/270, 271, 273, 277, 278, 282; 548/132, 213, 230, 229, 227, 244, 243, 263.2, 263.8, 312.4, 364.1, 365.1

(56) References Cited

U.S. PATENT DOCUMENTS

| | | | |
|---|---|---|---|
| 4,931,565 A | 6/1990 | Baba et al. | 548/363 |
| 4,986,845 A | 1/1991 | Oya et al. | 71/92 |
| 5,006,148 A | 4/1991 | Fischer et al. | 71/72 |
| RE34,779 E | 11/1994 | Oya et al. | 504/282 |
| 5,378,681 A | 1/1995 | Schallner et al. | 504/273 |
| 5,476,946 A | 12/1995 | Linker et al. | 504/273 |
| 5,663,362 A | 9/1997 | Haas et al. | 548/253.2 |
| 5,846,907 A | 12/1998 | von Deyn et al. | 504/221 |
| 5,939,360 A | 8/1999 | Adachi et al. | 504/271 |
| 5,948,917 A | 9/1999 | Adachi et al. | 548/247 |
| 6,165,944 A | 12/2000 | von Deyn et al. | 504/271 |

FOREIGN PATENT DOCUMENTS

| | | |
|---|---|---|
| CA | 2102750 | 5/1994 |
| CA | 2119673 | 9/1994 |
| DE | 4405614 | 8/1995 |

(List continued on next page.)

OTHER PUBLICATIONS

Chem. Abstracts 100:209881 & JP-A-58225070.
Chem. Abstracts 113:23939 & JP-A-02015069.

Primary Examiner—Joseph K. McKane
Assistant Examiner—Andrea D. Small
(74) Attorney, Agent, or Firm—Richard E. L. Henderson; Raymond J. Harmuth

(57) ABSTRACT

The invention relates to novel substituted benzoylpyrazoles of the general formula (I),

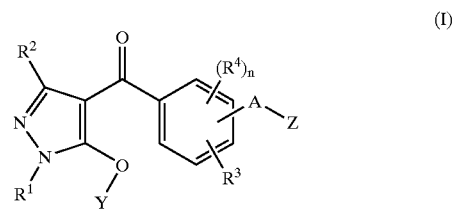

in which n represents the numbers 0, 1, 2 or 3, A represents a single bond or represents alkanediyl (alkylene), $R^1$ represents in each case optionally substituted alkyl, alkenyl, alkinyl or cycloalkyl, $R^2$ represents hydrogen, cyano, carbamoyl, thiocarbamoyl, halogen, or represents in each case optionally substituted alkyl, alkoxy, alkylthio, alkoxycarbonyl or cycloalkyl, $R^3$ represents hydrogen, nitro, cyano, carboxyl, carbamoyl, thiocarbamoyl, halogen, or represents in each case optionally substituted alkyl, alkoxy, alkylthio, alkylsulfinyl, alkylsulfonyl, alkylamino, dialkylamino or dialkylaminosulfonyl, $R^4$ represents nitro, cyano, carboxyl, carbamoyl, thiocarbamoyl, halogen, or represents in each case optionally substituted alkyl, alkoxy, alkylthio, alkylsulfinyl, alkylsulfonyl, alkylamino, dialkylamino or dialkylaminosulfonyl, Y represents hydrogen or represents in each case optionally substituted alkyl, alkylcarbonyl, alkoxycarbonyl, alkylsulfonyl, alkylaminocarbonyl, dialkylaminocarbonyl, alkenyl, alkenylcarbonyl, alkenylsulfonyl, alkinyl, alkinylcarbonyl, cycloalkyl, cycloalkylcarbonyl, cycloalkylalkyl, phenylcarbonyl, phenylsulfonyl, phenylalkyl or phenylcarbonylalkyl, and Z represents an optionally substituted 4- to 12-membered saturated or unsaturated monocyclic or bicyclic heterocyclic grouping which contains 1 to 4 heteroatoms (up to 4 nitrogen atoms and optionally—alternatively or additionally—one oxygen atom or one sulfur atom, or an SO grouping or an $SO_2$ grouping) and which additionally contains one to three oxo groups (C=O) and/or thioxo groups (C=S) as component of the heterocycle, and also to processes for their preparation and to their use as herbicides.

9 Claims, No Drawings

FOREIGN PATENT DOCUMENTS

| | | |
|---|---|---|
| EP | 0 900 795 | 3/1999 |
| WO | 97/41105 | 11/1997 |
| WO | 97/41116 | 11/1997 |
| WO | 97/41117 | 11/1997 |
| WO | 97/46530 | 12/1997 |
| WO | 98/28981 | 7/1998 |
| WO | 98/31681 | 7/1998 |
| WO | WO 98/31681 * | 7/1998 |
| WO | 98/42678 | 10/1998 |
| WO | 99/07697 | 2/1999 |

* cited by examiner

SUBSTITUTED BENZOYLPYRAZOLES AS HERBICIDES

The invention relates to novel substituted benzoylpyrazoles, to processes for their preparation and to their use as herbicides.

It is already known that certain substituted benzoylpyrazoles have herbicidal properties (cf. EP-A-352543, WO-A-96/26206, WO-A-97/35850, WO-A-97/41105, WO-A-97/41116, WO-A-97/41117, WO-A-97/41118, WO-A-97/46530, WO-A98/28981, WO-A-98/31681, WO-A-98/31682, WO-A-99/07697). However, the activity of these compounds is not entirely satisfactory.

This invention now provides the novel substituted benzoylpyrazoles of the general formula (I)

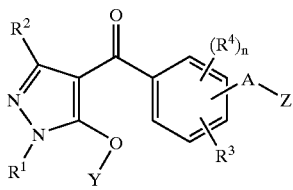

in which
n represents the numbers 0, 1, 2 or 3,
A represents a single bond or represents alkanediyl (alkylene),
$R^1$ represents in each case optionally substituted alkyl, alkenyl, alkinyl or cycloalkyl,
$R^2$ represents hydrogen, cyano, carbamoyl, thiocarbamoyl, halogen, or represents in each case optionally substituted alkyl, alkoxy, alkylthio, alkoxycarbonyl or cycloalkyl,
$R^3$ represents hydrogen, nitro, cyano, carboxyl, carbamoyl, thiocarbamoyl, halogen, or represents in each case optionally substituted alkyl, alkoxy, alkylthio, alkylsulfinyl, alkylsulfonyl, alkylamino, dialkylamino or dialkylaminosulfonyl,
$R^4$ represents nitro, cyano, carboxyl, carbamoyl, thiocarbamoyl, halogen, or represents in each case optionally substituted alkyl, alkoxy, alkylthio, alkylsulfinyl, alkylsulfonyl, alkylamino, dialkylamino or dialkylaminosulfonyl,
Y represents hydrogen or represents in each case optionally substituted alkyl, alkylcarbonyl, alkoxycarbonyl, alkylsulfonyl, alkylaminocarbonyl, dialkylaminocarbonyl, alkenyl, alkenylcarbonyl, alkenylsulfonyl, alkinyl, alkinylcarbonyl, cycloalkyl, cycloalkylcarbonyl, cycloalkylalkyl, phenylcarbonyl, phenylsulfonyl, phenylalkyl or phenylcarbonylalkyl, and
Z represents an optionally substituted 4- to 12-membered saturated or unsaturated monocyclic or bicyclic heterocyclic grouping which contains 1 to 4 heteroatoms (up to 4 nitrogen atoms and optionally—alternatively or additionally—one oxygen atom or one sulfur atom, or an $SO$ grouping or an $SO_2$ grouping) and which additionally contains one to three oxo groups (C=O) and/or thioxo groups (C=S) as component of the heterocycle,
including all possible tautomeric forms of the compounds of the general formula (I) and the possible salts of the compounds of the general formula (I).

In the definitions, the hydrocarbon chains, such as alkyl or alkanediyl, are in each case straight-chain or branched-including in combination with heteroatoms, such as in alkoxy.

n preferably represents the numbers 0, 1 or 2.
A preferably represents a single bond or represents alkanediyl(alkylene) having 1 to 4 carbon atoms.
$R^1$ preferably represents optionally cyano-, carboxyl-, carbamoyl-, halogen-, $C_1$–$C_4$-alkoxy-, $C_1$–$C_4$-alkylcarbonyl-, $C_1$–$C_4$-alkoxy-carbonyl-, $C_1$–$C_4$-alkylthio-, $C_1$–$C_4$-alkylsulfinyl- or $C_1$–$C_4$-alkylsulfonyl-substituted alkyl having 1 to 6 carbon atoms, represents in each case optionally cyano-, carboxyl-, carbamoyl-, halogen- or $C_1$–$C_4$-alkoxy-carbonyl-substituted alkenyl or alkinyl having in each case 2 to 6 carbon atoms, or represents optionally cyano-, carboxyl-, carbamoyl-, halogen-, $C_1$–$C_4$-alkyl- or $C_1$–$C_4$-alkoxy-carbonyl-substituted cycloalkyl having 3 to 6 carbon atoms.
$R^2$ preferably represents hydrogen, cyano, carbamoyl, thiocarbamoyl, halogen, represents in each case optionally cyano-, halogen- or $C_1$–$C_4$-alkoxy-substituted alkyl, alkoxy or alkoxycarbonyl having in each case up to 6 carbon atoms, represents optionally halogen-substituted alkylthio having 1 to 6 carbon atoms, or represents optionally cyano-, halogen- or $C_1$–$C_4$-alkyl-substituted cycloalkyl having 3 to 6 carbon atoms.
$R^3$ preferably represents hydrogen, nitro, cyano, carboxyl, carbamoyl, thiocarbamoyl, halogen, represents in each case optionally halogen, $C_1$–$C_4$-alkoxy-, $C_1$–$C_4$-alkylthio-, $C_1$–$C_4$-alkylsulfinyl- or $C_1$–$C_4$-alkylsulfonyl-substituted alkyl, alkoxy, alkylthio, alkylsulfinyl or alkylsulfonyl having in each case up to 4 carbon atoms in the alkyl groups, or represents alkylamino, dialkylamino or dialkylaminosulfonyl having in each case up to 4 carbon atoms in the alkyl groups.
$R^4$ preferably represents nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulfinyl- or $C_1$–$C_4$-alkylsulfonyl-substituted alkyl, alkoxy, alkylthio, alkylsulfinyl or alkylsulfonyl having in each case up to 4 carbon atoms in the alkyl groups, or represents alkylamino, dialkylamino or dialkylaminosulfonyl having in each case up to 4 carbon atoms in the alkyl groups.
Y preferably represents hydrogen, represents in each case optionally cyano-, carboxyl-, carbamoyl-, halogen- or $C_1$–$C_4$-alkoxycarbonyl-substituted alkyl, alkylcarbonyl or alkoxycarbonyl having in each case up to 6 carbon atoms, represents in each case optionally halogen-substituted alkylsulfonyl, alkylaminocarbonyl or dialkylaminocarbonyl having in each case up to 6 carbon atoms in the alkyl groups, represents in each case optionally cyano-, carboxyl-, carbamoyl-, halogen- or $C_1$–$C_4$-alkoxy-carbonyl-substituted alkenyl, alkenylcarbonyl, alkinyl or alkinylcarbonyl having in each case 2 to 6 carbon atoms, represents optionally halogen-substituted alkenylsulfonyl having up to 6 carbon atoms represents in each case optionally cyano-, halogen- or $C_1$–$C_4$-alkyl-substituted cycloalkyl, cycloalkylcarbonyl or cycloalkylalkyl having in each case 3 to 6 carbon atoms in the cycloalkyl groups and optionally 1 to 3 carbon atoms in the alkyl moiety, or represents in each case optionally nitro-, cyano-, carboxyl-, carbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenylcarbonyl, phenylsulfonyl, phenyl-$C_1$–$C_4$-alkyl or phenylcarbonyl-$C_1$–$C_4$-alkyl.

Z preferably represents one of the heterocyclic groupings below

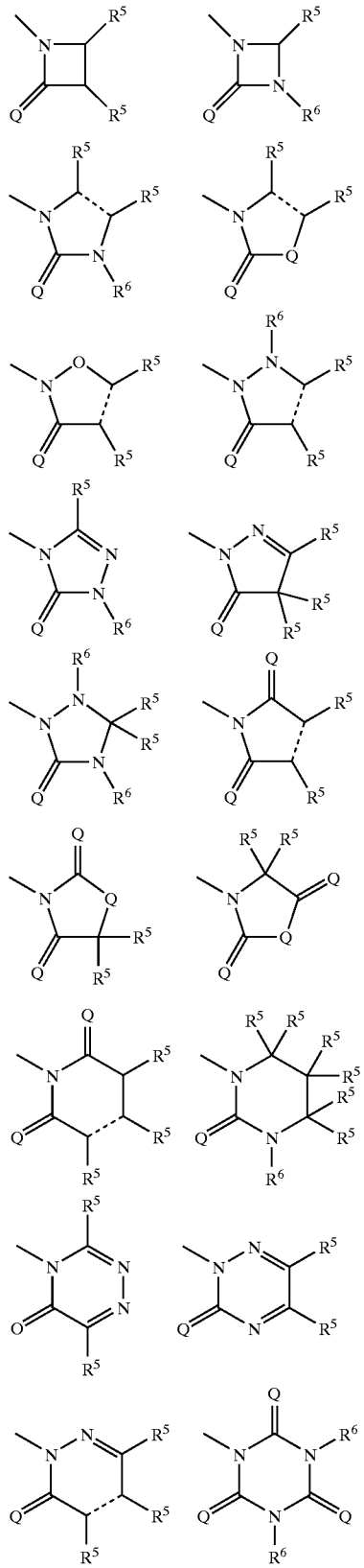

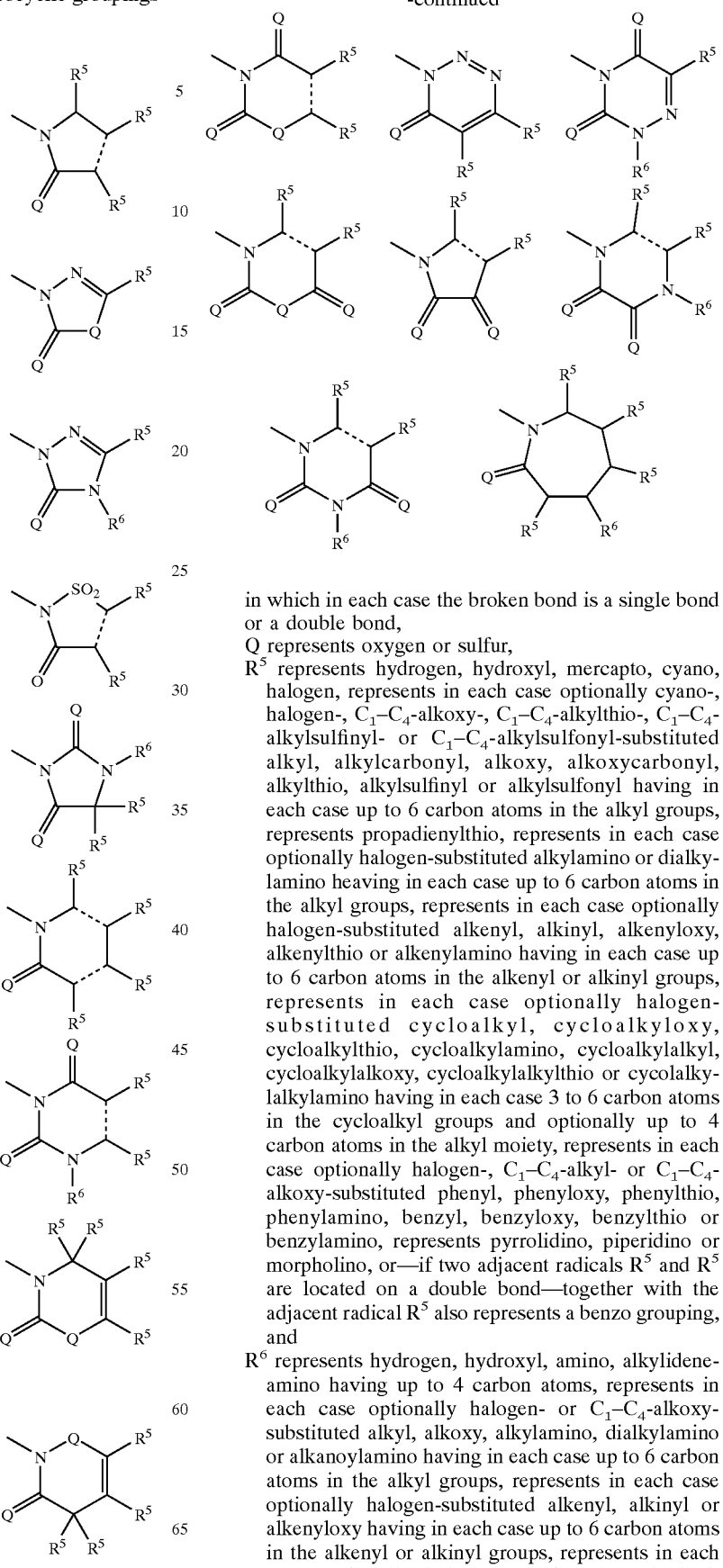

in which in each case the broken bond is a single bond or a double bond,

Q represents oxygen or sulfur, $R^5$ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulfinyl- or $C_1$–$C_4$-alkylsulfonyl-substituted alkyl, alkylcarbonyl, alkoxy, alkoxycarbonyl, alkylthio, alkylsulfinyl or alkylsulfonyl having in each case up to 6 carbon atoms in the alkyl groups, represents propadienylthio, represents in each case optionally halogen-substituted alkylamino or dialkylamino heaving in each case up to 6 carbon atoms in the alkyl groups, represents in each case optionally halogen-substituted alkenyl, alkinyl, alkenyloxy, alkenylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycolalkylalkylamino having in each case 3 to 6 carbon atoms in the cycloalkyl groups and optionally up to 4 carbon atoms in the alkyl moiety, represents in each case optionally halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, represents pyrrolidino, piperidino or morpholino, or—if two adjacent radicals $R^5$ and $R^5$ are located on a double bond—together with the adjacent radical $R^5$ also represents a benzo grouping, and $R^6$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ or $R^6$ represents optionally halogen- or $C_1$–$C_4$-alkyl-substituted alkanediyl having 3 to 5 carbon atoms, where the individual radicals $R^5$ and $R^6$—if a plurality of these are attached to the same heterocyclic groupings, may have identical or different meanings within the scope of the above definition.

Q preferably represents oxygen.

$R^5$ preferably represents hydrogen, hydroxyl, mercapto, cyano, fluorine, chlorine, bromine, iodine, represents in each case optionally fluorine-, chlorine-, methoxy-, ethoxy-, n- or i-propoxy-, n-, i-, s- or t-butoxy-, methylthio-, ethylthio-, n- or i-propylthio, n-, i-, s- or t-butylthio-, methylsulfinyl-, ethylsulfinyl-, n- or i-propylsulfinyl-, methylsulfonyl-, ethylsulfonyl-, n- or i-propylsulfonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulfinyl, ethylsulfinyl, n- or i-propylsulfinyl, methylsulfonyl, ethylsulfonyl, n- or i-propylsulfonyl, represents methylamino, ethylamino, n- or i-propylamino, n-, i-, s- or t-butylamino, dimethylamino, diethylamino, di-n-propylamino or di-i-propylamino, represents in each case optionally fluorine- and/or chlorine-substituted ethenyl, propenyl, butenyl, ethinyl, propinyl, butinyl, propenyloxy, butenyloxy, propenylthio, butenylthio, propenylamino or butenyl-amino, represents in each case optionally fluorine- and/or chlorine-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexymethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, represents in each case optionally fluorine-, chlorine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino, represents pyrrolidino, piperidino or morpholino, or—if two radicals $R^5$ and $R^5$ are located on a double bond—together with the adjacent radical $R^5$ also represents a benzo grouping.

$R^6$ preferably represents hydrogen, hydroxyl, amino, represents in each case optionally fluorine- and/or chlorine-, methoxy- or ethoxy-substituted, methyl, ethyl, n- or i-propyl, n-, i- or s-butyl, methoxy, ethoxy, n- or i-propoxy, methylamino, ethylamino or dimethylamino, represents in each case optionally fluorine- and/or chlorine-substituted ethenyl, propenyl, ethinyl, propinyl or propenyloxy, represents in each case optionally fluorine- and/or chlorine-substituted cyclopropyl, cyclobutyl, cyclopentyl, cyclohexyl, cyclopropylmethyl, cyclobutylmethyl, cyclopentylmethyl, cyclohexylmethyl, or represents in each case optionally fluorine-, chlorine-, methyl-, ethyl-, n- or i-propyl, n-, i-, s- or t-butyl-, methoxy-, ethoxy-, n- or i-propoxy-substituted phenyl or benzyl, or together with an adjacent radical $R^5$ or $R^6$ represents in each case optionally methyl- and/or ethyl-substituted propane-1,3-diyl(trimethylene), butane-1,4-diyl (tetramethylene) or pentane-1,5-diyl(pentamethylene).

n particularly preferably represents the numbers 0 or 1.

A particularly preferably represents a single bond, methylene, ethylidene (ethane-1,1-diyl) or dimethylene (ethane-1,2-diyl).

$R^1$ particularly preferably represents in each case optionally fluorine-, chlorine-, methoxy-, ethoxy-, n- or i-propoxy-, methylthio-, ethylthio-, n- or i-propylthio-, methylsulfinyl-, ethylsulfinyl-, n- or i-propylsulfinyl-, methylsulfonyl-, ethylsulfonyl-, n- or i-propylsulfonyl-substituted methyl, ethyl, n- or i-propyl, n-, i-, s- or t-butyl, represents in each case optionally fluorine-, chlorine- or bromine-substituted propenyl, butenyl, propinyl or butinyl, or represents in each case optionally cyano-, fluorine-, chlorine-, bromine-, methyl- or ethyl-substituted cyclopropyl, cyclobutyl, cyclopentyl or cyclohexyl.

$R^2$ particularly preferably represents hydrogen, cyano, carbamoyl, thiocarbamoyl, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, methoxycarbonyl, ethoxycarbonyl, n- or i-propoxycarbonyl, represents in each case optionally fluorine- and/or chlorine-substituted methylthio, ethylthio, n- or i-propylthio, or represents in each case optionally cyano-, fluorine-, chlorine-, bromine-, methyl- or ethyl-substituted cyclopropyl, cyclobutyl, cyclopentyl or cyclohexyl.

$R^3$ particularly preferably represents hydrogen, nitro, cyano, carboxyl, carbamoyl, thiocarbamoyl, fluorine, chlorine, bromine, iodine, represents in each case optionally fluorine- and/or chlorine-, methoxy-, ethoxy-, n- or i-propoxy-, methylthio-, ethylthio-, n- or i-propylthio-, methylsulfinyl-, ethylsulfinyl-, methylsulfonyl- or ethylsulfonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulfinyl, ethylsulfinyl, n- or i-propylsulfinyl, methylsulfonyl, ethylsulfonyl, n- or i-propylsulfonyl, or represents methylamino, ethylamino, n- or i-propylamino, dimethylamino, diethylamino, dimethylaminosulfonyl or diethylaminosulfonyl.

$R^4$ particularly preferably represents nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulfinyl-, ethylsulfinyl-, methylsulfonyl or ethylsulfonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulfinyl, ethylsulfinyl, n- or i-propylsulfinyl, methylsulfonyl, ethylsulfonyl, n- or i-propylsulfonyl, or represents methylamino, ethyl amino, n- or i-propylamino, dimethylamino, diethylamino, dimethylaminosulfonyl or diethylaminosulfonyl.

$R^5$ particularly preferably represents hydrogen, hydroxyl, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, fluoroethyl, chloroethyl, difluoroethyl, dichloroethyl, fluoro-n-propyl, fluoro-i-propyl, chloro-n-propyl, chloro-i-propyl, methoxymethyl, ethoxymethyl, methoxyethyl, ethoxyethyl, methoxy, ethoxy, n- or i-propoxy, n-, i-, s- or t-butoxy, fluoroethoxy, chloroethoxy, difluoroethoxy, dichloroethoxy, trifluoroethoxy, trichloroethoxy, chlorofluoroethoxy, chlorodifluoroethoxy, fluorodichloromethyl, methylthio, ethylthio, n- or i-propylthio, fluoroethylthio, chloroethylthio, difluoroethylthio, dichloroethylthio, chlorofluoroethylthio, chlorodifluoroethylthio, fluorodichloroethylthio, methylsulfinyl, ethylsulfinyl, n- or i-propylsulfinyl, methylsulfonyl, ethylsulfonyl, n- or i-propylsulfonyl, dimethylamino, propenylthio, butenylthio, propinylthio, butinylthio, cyclopropyl, cyclopropylmethyl, cyclopropylmethoxy, phenyl or phenoxy.

$R^6$ particularly preferably represents amino, methyl, ethyl, n- or i-propyl, n-, i-, s- or t-butyl, methoxy, ethoxy, methylamino, dimethylamino, cyclopropyl or cyclopropylmethyl, or together with $R^5$ represents propane-1,3-diyl(trimethylene), butane-1,4-diyl (tetramethylene) or pentane-1,5-diyl(pentamethylene).

Y particularly preferably represents hydrogen, represents in each case optionally cyano-, fluorine-, chlorine-, methoxy- or ethoxy-substituted methyl, ethyl, n- or i-propyl, acetyl, propionyl, n- or i-butyroyl, methoxycarbonyl or ethoxycarbonyl, represents in each case optionally fluorine-, chlorine- and/or bromine-substituted methylsulfonyl-, ethylsulfonyl-, n- or i-propylsulfonyl-, n-, i-, s- or t-butylsulfonyl-, methylaminocarbonyl, ethylaminocarbonyl, n- or i-propylaminocarbonyl, dimethylaminocarbonyl or diethylaminocarbonyl, represents in each case optionally fluorine-, chlorine- or bromine-substituted propenyl, butenyl, propenylcarbonyl, butenylcarbonyl, propenylsulfonyl, butenylsulfonyl, propinyl, butinyl, propinylcarbonyl or butinylcarbonyl, represents in each case optionally cyano-, fluorine-, chlorine-, methyl- or ethyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropylmethyl, cyclobutylmethyl, cyclopentylmethyl or cyclohexylmethyl, or represents in each case optionally nitro, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenylcarbonyl, phenylsulfonyl, benzyl or phenylcarbonylmethyl.

Z particularly preferably represents

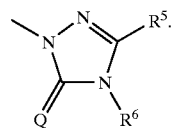

n very particularly preferably represents 0.

A very particularly preferably represents a single bond or represents methylene.

$R^1$ very particularly preferably represents in each case optionally fluorine, chlorine-, methoxy-, ethoxy-, methylthio-, ethylthio-, methylsulfinyl-, ethylsulfinyl-, methylsulfonyl- or ethylsulfonyl-substituted methyl, ethyl, n- or i-propyl, n-, i-, s- or t-butyl, or represents optionally cyano-, fluorine-, chlorine-, bromine-, methyl- or ethyl-substituted cyclopropyl.

$R^2$ very particularly preferably represents hydrogen, cyano, carbamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxycarbonyl, ethoxycarbonyl, n- or i-propoxycarbonyl, represents in each case optionally fluorine- and/or chlorine-substituted methylthio, ethylthio, n- or i-propylthio, or represents cyclopropyl.

$R^3$ very particularly preferably represents hydrogen, nitro, cyano, fluorine, chlorine, bromine, iodine, methyl, ethyl, trifluoromethyl, methoxymethyl, methylthiomethyl, methylsulfinylmethyl, methylsulfonylmethyl, methoxy, ethoxy, difluoromethoxy, trifluoromethoxy, methylthio, ethylthio, methylsulfinyl, ethylsulfinyl, methylsulfonyl, ethylsulfonyl or dimethylaminosulfonyl.

$R^4$ particularly preferably represents nitro, cyano, fluorine, chlorine, bromine, methyl, ethyl, trifluoromethyl, methoxymethyl, methylthiomethyl, methylsulfinylmethyl, methylsulfonylmethyl, methoxy, ethoxy, difluoromethoxy, trifluoromethoxy, methylthio, ethylthio, methylsulfinyl, ethylsulfinyl, methylsulfonyl, ethylsulfonyl, dimethylamino or dimethylaminosulfonyl.

$R^6$ very particularly preferably represents methyl, cyclopropyl, dimethylamino, methoxy or ethoxy.

Y very particularly preferably represents hydrogen.

A most preferably represents methylene.

$R^1$ most preferably represents methyl or ethyl.

$R^2$ most preferably represents hydrogen or methyl.

$R^3$ most preferably represents hydrogen, fluorine, chlorine, bromine, trifluoromethyl or methylsulfonyl.

$R^4$ most preferably represents (2-)chlorine, (4-)chlorine, (6-)trifluoromethyl or (2-)methylsulfonyl.

Preference according to the invention is given to compounds of the formula (I) which contains a combination of the meanings listed above as being preferred.

Particular preference according to the invention is given to the compounds of the formula (I) which contain a combination of the meanings listed above as being particularly preferred.

Very particular preference is given to the compounds of the formula (I) which contain a combination of the meanings listed above as being very particularly preferred.

Most preference according to the invention is given to the compounds of the formula (I) which contain a combination of the meanings listed above as being most preferred.

The present invention in particular provides the compounds of the general formulae (IA), (IB) and (IC):

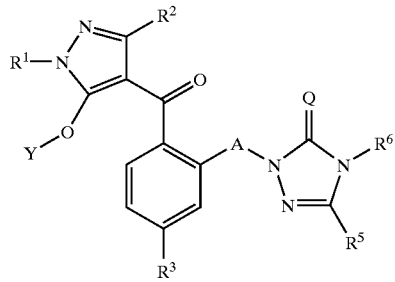
(IA)

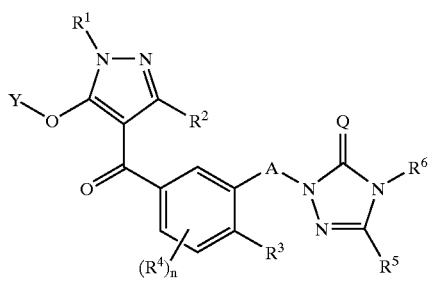
(IB)

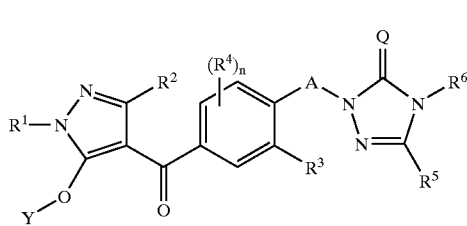
(IC)

in which n, A, Q, $R^1$, $R^2$, $R^3$, $R^4$, $R^5$, $R^6$ and Y are as defined above.

The invention preferably also provides sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulfonium, $C_5$- or $C_6$-Cycloalkyl-ammonium and di-($C_1$–$C_2$-alkyl)-benzylammonium salts of compounds of the formula (I), in which n, A, $R^1$, $R^2$, $R^3$, $R^4$, Y and Z are as defined above.

The abovementioned general or preferred radical definitions apply both to the end products of the formula (I) and, correspondingly to the starting materials or intermediates required in each case for the preparation. These radical definitions can be combined with one another as desired, i.e. including combinations between the given preferred ranges.

Examples of the compounds of the general formula (I) according to the invention are given in the groups below.

Group 1

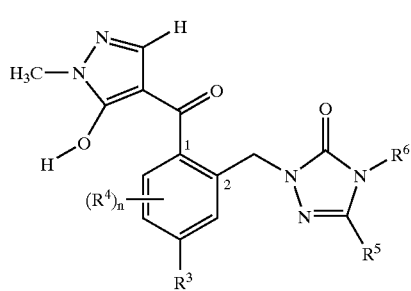
(IA-1)

Here, $R^3$, $(R^4)_n$, $R^5$ and $R^6$ have, for example, the meanings given in the table below:

| $R^3$ | (Position) $(R^4)_n$ | $R^5$ | $R^6$ |
|---|---|---|---|
| H | — | $CF_3$ | $CH_3$ |
| F | — | $CF_3$ | $CH_3$ |
| Cl | — | $CF_3$ | $CH_3$ |
| Br | — | $CF_3$ | $CH_3$ |
| I | — | $CF_3$ | $CH_3$ |
| $NO_2$ | — | $CF_3$ | $CH_3$ |
| CN | — | $CF_3$ | $CH_3$ |
| $CH_3$ | — | $CF_3$ | $CH_3$ |
| $OCH_3$ | — | $CF_3$ | $CH_3$ |
| $CF_3$ | — | $CF_3$ | $CH_3$ |
| $OCHF_2$ | — | $CF_3$ | $CH_3$ |
| $OCF_3$ | — | $CF_3$ | $CH_3$ |
| $SO_2CH_3$ | — | $CF_3$ | $CH_3$ |
| H | — | $OCH_3$ | $CH_3$ |
| F | — | $OCH_3$ | $CH_3$ |
| Cl | — | $OCH_3$ | $CH_3$ |
| Br | — | $OCH_3$ | $CH_3$ |
| I | — | $OCH_3$ | $CH_3$ |
| $NO_2$ | — | $OCH_3$ | $CH_3$ |
| CN | — | $OCH_3$ | $CH_3$ |
| $CH_3$ | — | $OCH_3$ | $CH_3$ |
| $OCH_3$ | — | $OCH_3$ | $CH_3$ |
| $CF_3$ | — | $OCH_3$ | $CH_3$ |
| $OCHF_2$ | — | $OCH_3$ | $CH_3$ |
| $OCF_3$ | — | $OCH_3$ | $CH_3$ |
| $SO_2CH_3$ | — | $OCH_3$ | $CH_3$ |
| H | — | $SCH_3$ | $CH_3$ |
| F | — | $SCH_3$ | $CH_3$ |
| Cl | — | $SCH_3$ | $CH_3$ |
| Br | — | $SCH_3$ | $CH_3$ |
| I | — | $SCH_3$ | $CH_3$ |
| $NO_2$ | — | $SCH_3$ | $CH_3$ |
| CN | — | $SCH_3$ | $CH_3$ |
| $CH_3$ | — | $SCH_3$ | $CH_3$ |
| $OCH_3$ | — | $SCH_3$ | $CH_3$ |
| $CF_3$ | — | $SCH_3$ | $CH_3$ |
| $OCHF_2$ | — | $SCH_3$ | $CH_3$ |
| $OCF_3$ | — | $SCH_3$ | $CH_3$ |
| $SO_2CH_3$ | — | $SCH_3$ | $CH_3$ |
| H | — | $OC_2H_5$ | $CH_3$ |
| F | — | $OC_2H_5$ | $CH_3$ |
| Cl | — | $OC_2H_5$ | $CH_3$ |
| Br | — | $OC_2H_5$ | $CH_3$ |
| I | — | $OC_2H_5$ | $CH_3$ |
| $NO_2$ | — | $OC_2H_5$ | $CH_3$ |
| CN | — | $OC_2H_5$ | $CH_3$ |
| $CH_3$ | — | $OC_2H_5$ | $CH_3$ |
| $OCH_3$ | — | $OC_2H_5$ | $CH_3$ |
| $CF_3$ | — | $OC_2H_5$ | $CH_3$ |
| $OCHF_2$ | — | $OC_2H_5$ | $CH_3$ |
| $OCF_3$ | — | $OC_2H_5$ | $CH_3$ |
| $SO_2CH_3$ | — | $OC_2H_5$ | $CH_3$ |
| H | — | $N(CH_3)_2$ | $CH_3$ |
| F | — | $N(CH_3)_2$ | $CH_3$ |
| Cl | — | $N(CH_3)_2$ | $CH_3$ |
| Br | — | $N(CH_3)_2$ | $CH_3$ |
| I | — | $N(CH_3)_2$ | $CH_3$ |
| $NO_2$ | — | $N(CH_3)_2$ | $CH_3$ |
| CN | — | $N(CH_3)_2$ | $CH_3$ |
| $CH_3$ | — | $N(CH_3)_2$ | $CH_3$ |
| $OCH_3$ | — | $N(CH_3)_2$ | $CH_3$ |
| $CF_3$ | — | $N(CH_3)_2$ | $CH_3$ |
| $OCHF_2$ | — | $N(CH_3)_2$ | $CH_3$ |
| $OCF_3$ | — | $N(CH_3)_2$ | $CH_3$ |
| $SO_2CH_3$ | — | $N(CH_3)_2$ | $CH_3$ |
| H | — | $OCH_3$ | △ |
| F | — | $OCH_3$ | △ |
| Cl | — | $OCH_3$ | △ |
| Br | — | $OCH_3$ | △ |
| I | — | $OCH_3$ | △ |
| $NO_2$ | — | $OCH_3$ | △ |
| CN | — | $OCH_3$ | △ |
| $CH_3$ | — | $OCH_3$ | △ |

-continued

| $R^3$ | (Position) $(R^4)_n$ | $R^5$ | $R^6$ |
|---|---|---|---|
| OCH₃ | — | OCH₃ | △ |
| CF₃ | — | OCH₃ | △ |
| OCHF₂ | — | OCH₃ | △ |
| OCF₃ | — | OCH₃ | △ |
| SO₂CH₃ | — | OCH₃ | △ |
| H | (5-) Cl | CF₃ | CH₃ |
| F | (5-) Cl | CH₃ | CH₃ |
| Cl | (5-) Cl | OCH₃ | CH₃ |
| Br | (5-) Cl | Br | △ |
| Cl | (5-) Cl | CF₃ | CH₃ |
| NO₂ | (5-) Cl | CH₃ | CH₃ |
| Cl | (5-) Cl | SCH₃ | CH₃ |
| CH₃ | (5-) Cl | Cl | CH₃ |
| OCH₃ | (5-) Cl | OCH₃ | CH₃ |
| CF₃ | (5-) Cl | CF₃ | CH₃ |
| OCHF₂ | (5-) Cl | CH₃ | CH₃ |
| OCF₃ | (5-) Cl | CH₃ | CH₃ |
| SO₂CH₃ | (5-) Cl | OCH₃ | CH₃ |

Group 2 (IA-2)

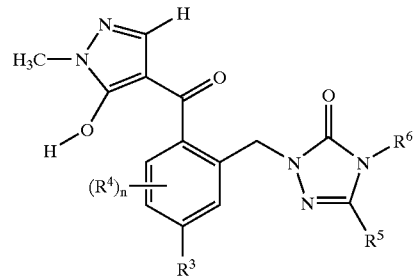

Here, $R^3$, $(R^4)_n$, $R^5$ and $R^6$ have, for example, the meanings given above in group 1.

Group 3 (IA-3)

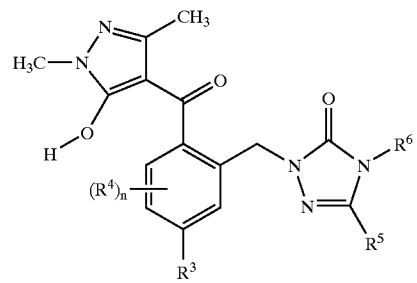

Here, $R^3$, $(R^4)_n$, $R^5$ and $R^6$ have, for example, the meanings given above in group 1.

Group 4 (IB-1)

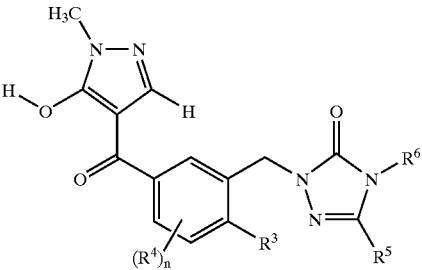

Here, $R^3$, $(R^4)_n$, $R^5$ and $R^6$ have, for example, the meanings given in the table below:

| $R^3$ | (Position) $(R^4)_n$ | $R^5$ | $R^6$ |
|---|---|---|---|
| Cl | (2-) Cl | CF₃ | CH₃ |
| Cl | (2-) Cl | SCH₃ | CH₃ |
| Cl | (2-) Cl | SC₂H₅ | CH₃ |
| Cl | (2-) Cl | SC₃H₇ | CH₃ |
| Cl | (2-) Cl | SC₃H₇-i | CH₃ |
| Cl | (2-) Cl | 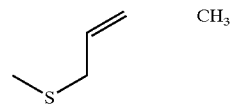 | CH₃ |
| Cl | (2-) Cl | 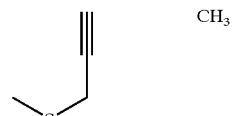 | CH₃ |
| Cl | (2-) Cl | 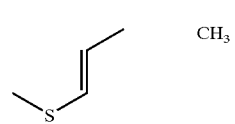 | CH₃ |
| Cl | (2-) Cl |  | CH₃ |
| Cl | (2-) Cl |  | CH₃ |
| Cl | (2-) Cl | SCH=C=CH₂ | CH₃ |
| Cl | (2-) Cl | SCH₂CN | CH₃ |
| Cl | (2-) Cl | SCH₂CH₂CN | CH₃ |
| Cl | (2-) Cl | OCH₃ | CH₃ |
| Cl | (2-) Cl | OC₂H₅ | CH₃ |
| Cl | (2-) Cl | OC₃H₇ | CH₃ |
| Cl | (2-) Cl | OC₃H₇-i | CH₃ |
| Cl | (2-) Cl | OC₄H₉ | CH₃ |
| Cl | (2-) Cl | OCH₂CF₃ | CH₃ |
| Cl | (2-) Cl | 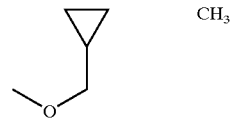 | CH₃ |

-continued

| R³ | (Position) (R⁴)ₙ | R⁵ | R⁶ |
|---|---|---|---|
| Cl | (2-) Cl | OC₆H₅ | CH₃ |
| Cl | (2-) Cl | H | CH₃ |
| Cl | (2-) Cl | CH₃ | CH₃ |
| Cl | (2-) Cl | C₂H₅ | CH₃ |
| Cl | (2-) Cl | C₃H₇ | CH₃ |
| Cl | (2-) Cl | C₃H₇-i | CH₃ |
| Cl | (2-) Cl | C₄H₉ | CH₃ |
| Cl | (2-) Cl | C₄H₉-i | CH₃ |
| Cl | (2-) Cl | C₄H₉-s | CH₃ |
| Cl | (2-) Cl | C₄H₉-t | CH₃ |
| Cl | (2-) Cl | cyclopropyl-CH₂ | CH₃ |
| Cl | (2-) Cl | cyclopropyl-CH₂CH₂ | CH₃ |
| Cl | (2-) Cl | CH=CHCH₃ | CH₃ |
| Cl | (2-) Cl | benzyl (C₆H₅CH₂) | CH₃ |
| Cl | (2-) Cl | 4-Cl-C₆H₄-CH₂ | CH₃ |
| Cl | (2-) Cl | C₆H₅CH₂CH₂ | CH₃ |
| Cl | (2-) Cl | N(CH₃)₂ | CH₃ |
| Cl | (2-) Cl | 4-morpholinyl | CH₃ |
| Cl | (2-) Cl | Cl | CH₃ |
| Cl | (2-) Cl | Br | CH₃ |
| SO₂CH₃ | (2-) Cl | CF₃ | CH₃ |
| SO₂CH₃ | (2-) Cl | SCH₃ | CH₃ |
| SO₂CH₃ | (2-) Cl | SC₂H₅ | CH₃ |
| SO₂CH₃ | (2-) Cl | SC₃H₇ | CH₃ |
| SO₂CH₃ | (2-) Cl | SC₃H₇-i | CH₃ |
| SO₂CH₃ | (2-) Cl | SCH₂CH=CH₂ | CH₃ |
| SO₂CH₃ | (2-) Cl | SCH₂C≡CH | CH₃ |
| SO₂CH₃ | (2-) Cl | SCH=CHCH₃ | CH₃ |
| SO₂CH₃ | (2-) Cl | SCH=C=CH₂ (propynyl-S-) | CH₃ |
| SO₂CH₃ | (2-) Cl | S-CH₂-cyclopropyl | CH₃ |
| SO₂CH₃ | (2-) Cl | SCH=C=CH₂ | CH₃ |
| SO₂CH₃ | (2-) Cl | SCH₂CN | CH₃ |
| SO₂CH₃ | (2-) Cl | SCH₂CH₂CN | CH₃ |
| SO₂CH₃ | (2-) Cl | OCH₃ | CH₃ |
| SO₂CH₃ | (2-) Cl | OC₂H₅ | CH₃ |
| SO₂CH₃ | (2-) Cl | OC₃H₇ | CH₃ |
| SO₂CH₃ | (2-) Cl | OC₃H₇-i | CH₃ |
| SO₂CH₃ | (2-) Cl | OC₄H₉ | CH₃ |
| SO₂CH₃ | (2-) Cl | OCH₂CF₃ | CH₃ |
| SO₂CH₃ | (2-) Cl | OCH₂-cyclopropyl (glycidyl-like) | CH₃ |
| SO₂CH₃ | (2-) Cl | OC₆H₅ | CH₃ |
| SO₂CH₃ | (2-) Cl | H | CH₃ |
| SO₂CH₃ | (2-) Cl | CH₃ | CH₃ |
| SO₂CH₃ | (2-) Cl | C₂H₅ | CH₃ |
| SO₂CH₃ | (2-) Cl | C₃H₇ | CH₃ |
| SO₂CH₃ | (2-) Cl | C₃H₇-i | CH₃ |
| SO₂CH₃ | (2-) Cl | C₄H₉ | CH₃ |
| SO₂CH₃ | (2-) Cl | C₄H₉-i | CH₃ |
| SO₂CH₃ | (2-) Cl | C₄H₉-s | CH₃ |
| SO₂CH₃ | (2-) Cl | C₄H₉-t | CH₃ |
| SO₂CH₃ | (2-) Cl | cyclopropyl-CH₂ | CH₃ |
| SO₂CH₃ | (2-) Cl | cyclopropyl-CH₂CH₂ | CH₃ |
| SO₂CH₃ | (2-) Cl | CH=CHCH₃ | CH₃ |
| SO₂CH₃ | (2-) Cl | benzyl (C₆H₅CH₂) | CH₃ |
| SO₂CH₃ | (2-) Cl | 4-Cl-C₆H₄-CH₂ | CH₃ |
| SO₂CH₃ | (2-) Cl | C₆H₅CH₂CH₂ | CH₃ |
| SO₂CH₃ | (2-) Cl | N(CH₃)₂ | CH₃ |
| SO₂CH₃ | (2-) Cl | 4-morpholinyl | CH₃ |

-continued

| R³ | (Position) (R⁴)ₙ | R⁵ | R⁶ |
|---|---|---|---|
| SO₂CH₃ | (2-) Cl | Cl | CH₃ |
| SO₂CH₃ | (2-) Cl | Br | CH₃ |
| Cl | (2-) SO₂CH₃ | CF₃ | CH₃ |
| Cl | (2-) SO₂CH₃ | SCH₃ | CH₃ |
| Cl | (2-) SO₂CH₃ | SC₂H₅ | CH₃ |
| Cl | (2-) SO₂CH₃ | SC₃H₇ | CH₃ |
| Cl | (2-) SO₂CH₃ | SC₃H₇-i | CH₃ |
| Cl | (2-) SO₂CH₃ | allyl-S– | CH₃ |
| Cl | (2-) SO₂CH₃ | propargyl-S– | CH₃ |
| Cl | (2-) SO₂CH₃ | propenyl-S– | CH₃ |
| Cl | (2-) SO₂CH₃ | propynyl-S– | CH₃ |
| Cl | (2-) SO₂CH₃ | cyclopropyl-CH₂-S– | CH₃ |
| Cl | (2-) SO₂CH₃ | SCH=C=CH₂ | CH₃ |
| Cl | (2-) SO₂CH₃ | SCH₂CN | CH₃ |
| Cl | (2-) SO₂CH₃ | SCH₂CH₂CN | CH₃ |
| Cl | (2-) SO₂CH₃ | OCH₃ | CH₃ |
| Cl | (2-) SO₂CH₃ | OC₂H₅ | CH₃ |
| Cl | (2-) SO₂CH₃ | OC₃H₇ | CH₃ |
| Cl | (2-) SO₂CH₃ | OC₃H₇-i | CH₃ |
| Cl | (2-) SO₂CH₃ | OC₄H₉ | CH₃ |
| Cl | (2-) SO₂CH₃ | OCH₂CF₃ | CH₃ |
| Cl | (2-) SO₂CH₃ | cyclopropyl-CH₂-O– | CH₃ |
| Cl | (2-) SO₂CH₃ | OC₆H₅ | CH₃ |
| Cl | (2-) SO₂CH₃ | H | CH₃ |
| Cl | (2-) SO₂CH₃ | CH₃ | CH₃ |
| Cl | (2-) SO₂CH₃ | C₂H₅ | CH₃ |
| Cl | (2-) SO₂CH₃ | C₃H₇ | CH₃ |
| Cl | (2-) SO₂CH₃ | C₃H₇-i | CH₃ |
| Cl | (2-) SO₂CH₃ | C₄H₉ | CH₃ |
| Cl | (2-) SO₂CH₃ | C₄H₉-i | CH₃ |
| Cl | (2-) SO₂CH₃ | C₄H₉-s | CH₃ |
| Cl | (2-) SO₂CH₃ | C₄H₉-t | CH₃ |
| Cl | (2-) SO₂CH₃ | cyclopropyl | CH₃ |
| Cl | (2-) SO₂CH₃ | cyclopropyl-CH₂– | CH₃ |
| Cl | (2-) SO₂CH₃ | CH=CHCH₃ | CH₃ |
| Cl | (2-) SO₂CH₃ | phenyl | CH₃ |
| Cl | (2-) SO₂CH₃ | 4-chlorophenyl | CH₃ |
| Cl | (2-) SO₂CH₃ | benzyl-CH₂– | CH₃ |
| Cl | (2-) SO₂CH₃ | N(CH₃)₂ | CH₃ |
| Cl | (2-) SO₂CH₃ | morpholinyl | CH₃ |
| Cl | (2-) SO₂CH₃ | Cl | CH₃ |
| Cl | (2-) SO₂CH₃ | Br | CH₃ |
| Cl | (2-) Cl | CF₃ | cyclopropyl |
| Cl | (2-) Cl | SCH₃ | cyclopropyl |
| Cl | (2-) Cl | SC₂H₅ | cyclopropyl |
| Cl | (2-) Cl | SC₃H₇ | cyclopropyl |
| Cl | (2-) Cl | SC₃H₇-i | cyclopropyl |
| Cl | (2-) Cl | allyl-S– | cyclopropyl |
| Cl | (2-) Cl | propargyl-S– | cyclopropyl |
| Cl | (2-) Cl | propenyl-S– | cyclopropyl |

-continued

| $R^3$ | (Position)$(R^4)_n$ | $R^5$ | $R^6$ |
|---|---|---|---|
| Cl | (2-) Cl | C≡C-CH₂-S- | cyclopropyl |
| Cl | (2-) Cl | cyclopropyl-CH₂-S- | cyclopropyl |
| Cl | (2-) Cl | SCH=C=CH₂ | cyclopropyl |
| Cl | (2-) Cl | SCH₂CN | cyclopropyl |
| Cl | (2-) Cl | SCH₂CH₂CN | cyclopropyl |
| Cl | (2-) Cl | OCH₃ | cyclopropyl |
| Cl | (2-) Cl | OC₂H₅ | cyclopropyl |
| Cl | (2-) Cl | OC₃H₇ | cyclopropyl |
| Cl | (2-) Cl | OC₃H₇-i | cyclopropyl |
| Cl | (2-) Cl | OC₄H₉ | cyclopropyl |
| Cl | (2-) Cl | OCH₂CF₃ | cyclopropyl |
| Cl | (2-) Cl | cyclopropyl-CH₂-O-CH₃ | cyclopropyl |
| Cl | (2-) Cl | OC₆H₅ | cyclopropyl |
| Cl | (2-) Cl | H | cyclopropyl |
| Cl | (2-) Cl | CH₃ | cyclopropyl |
| Cl | (2-) Cl | C₂H₅ | cyclopropyl |
| Cl | (2-) Cl | C₃H₇ | cyclopropyl |
| Cl | (2-) Cl | C₃H₇-i | cyclopropyl |
| Cl | (2-) Cl | C₄H₉ | cyclopropyl |
| Cl | (2-) Cl | C₄H₉-i | cyclopropyl |
| Cl | (2-) Cl | C₄H₉-s | cyclopropyl |
| Cl | (2-) Cl | C₄H₉-t | cyclopropyl |
| Cl | (2-) Cl | cyclopropyl | cyclopropyl |
| Cl | (2-) Cl | cyclopropyl-CH₂- | cyclopropyl |
| Cl | (2-) Cl | CH=CHCH₃ | cyclopropyl |
| Cl | (2-) Cl | phenyl | cyclopropyl |
| Cl | (2-) Cl | 4-Cl-phenyl | cyclopropyl |
| Cl | (2-) Cl | benzyl-CH₂- | cyclopropyl |
| Cl | (2-) Cl | N(CH₃)₂ | cyclopropyl |
| Cl | (2-) Cl | morpholino | cyclopropyl |
| Cl | (2-) Cl | Cl | cyclopropyl |
| Cl | (2-) Cl | Br | cyclopropyl |

-continued

| R³ | (Position)(R⁴)ₙ | R⁵ | R⁶ |
|---|---|---|---|
| SO₂CH₃ | (2-) Cl | CF₃ |  |
| SO₂CH₃ | (2-) Cl | SCH₃ |  |
| SO₂CH₃ | (2-) Cl | SC₂H₅ |  |
| SO₂CH₃ | (2-) Cl | SC₃H₇ |  |
| SO₂CH₃ | (2-) Cl | SC₃H₇-i |  |
| SO₂CH₃ | (2-) Cl |  |  |
| SO₂CH₃ | (2-) Cl |  |  |
| SO₂CH₃ | (2-) Cl | 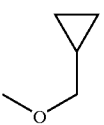 |  |
| SO₂CH₃ | (2-) Cl | 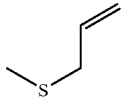 |  |
| SO₂CH₃ | (2-) Cl |  | 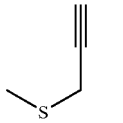 |
| SO₂CH₃ | (2-) Cl | SCH=C=CH₂ |  |
| SO₂CH₃ | (2-) Cl | SCH₂CN |  |
| SO₂CH₃ | (2-) Cl | SCH₂CH₂CN | 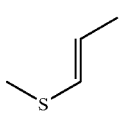 |
| SO₂CH₃ | (2-) Cl | OCH₃ |  |
| SO₂CH₃ | (2-) Cl | OC₂H₅ |  |

-continued

| R³ | (Position)(R⁴)ₙ | R⁵ | R⁶ |
|---|---|---|---|
| SO₂CH₃ | (2-) Cl | OC₃H₇ | 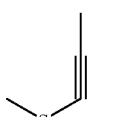 |
| SO₂CH₃ | (2-) Cl | OC₃H₇-i |  |
| SO₂CH₃ | (2-) Cl | OC₄H₉ |  |
| SO₂CH₃ | (2-) Cl | OCH₂CF₃ | 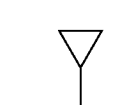 |
| SO₂CH₃ | (2-) Cl |  |  |
| SO₂CH₃ | (2-) Cl | OC₆H₅ | 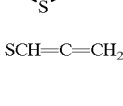 |
| SO₂CH₃ | (2-) Cl | H |  |
| SO₂CH₃ | (2-) Cl | CH₃ |  |
| SO₂CH₃ | (2-) Cl | C₂H₅ |  |
| SO₂CH₃ | (2-) Cl | C₃H₇ |  |
| SO₂CH₃ | (2-) Cl | C₃H₇-i |  |
| SO₂CH₃ | (2-) Cl | C₄H₉ |  |
| SO₂CH₃ | (2-) Cl | C₄H₉-i |  |
| SO₂CH₃ | (2-) Cl | C₄H₉-s |  |
| SO₂CH₃ | (2-) Cl | C₄H₉-t |  |
| SO₂CH₃ | (2-) Cl |  |  |

-continued

| R³ | (Position) (R⁴)ₙ | R⁵ | R⁶ |
|---|---|---|---|
| SO₂CH₃ | (2-) Cl | 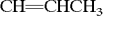 |  |
| SO₂CH₃ | (2-) Cl | CH=CHCH₃ | 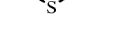 |
| SO₂CH₃ | (2-) Cl |  |  |
| SO₂CH₃ | (2-) Cl | 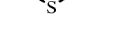 |  |
| SO₂CH₃ | (2-) Cl | 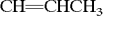 |  |
| SO₂CH₃ | (2-) Cl | N(CH₃)₂ | 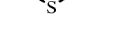 |
| SO₂CH₃ | (2-) Cl |  | 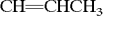 |
| SO₂CH₃ | (2-) Cl | Cl |  |
| SO₂CH₃ | (2-) Cl | Br | 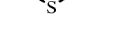 |
| Cl | (2-) SO₂CH₃ | CF₃ |  |
| Cl | (2-) SO₂CH₃ | SCH₃ | 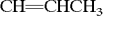 |
| Cl | (2-) SO₂CH₃ | SC₂H₅ |  |
| Cl | (2-) SO₂CH₃ | SC₃H₇ | 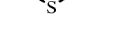 |
| Cl | (2-) SO₂CH₃ | SC₃H₇-i |  |
| Cl | (2-) SO₂CH₃ |  |  |

-continued

| R³ | (Position) (R⁴)ₙ | R⁵ | R⁶ |
|---|---|---|---|
| Cl | (2-) SO₂CH₃ | 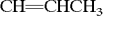 |  |
| Cl | (2-) SO₂CH₃ |  |  |
| Cl | (2-) SO₂CH₃ |  |  |
| Cl | (2-) SO₂CH₃ |  |  |
| Cl | (2-) SO₂CH₃ | SCH=C=CH₂ |  |
| Cl | (2-) SO₂CH₃ | SCH₂CN |  |
| Cl | (2-) SO₂CH₃ | SCH₂CH₂CN |  |
| Cl | (2-) SO₂CH₃ | OCH₃ |  |
| Cl | (2-) SO₂CH₃ | OC₂H₅ |  |
| Cl | (2-) SO₂CH₃ | OC₃H₇ |  |
| Cl | (2-) SO₂CH₃ | OC₃H₇-i |  |
| Cl | (2-) SO₂CH₃ | OC₄H₉ |  |
| Cl | (2-) SO₂CH₃ | OCH₂CF₃ | 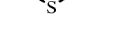 |
| Cl | (2-) SO₂CH₃ |  | 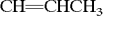 |
| Cl | (2-) SO₂CH₃ | OC₆H₅ |  |

-continued

| R³ | (Position)(R⁴)ₙ | R⁵ | R⁶ |
|---|---|---|---|
| Cl | (2-) | SO₂CH₃ | H | cyclopropyl |
| Cl | (2-) SO₂CH₃ | CH₃ | cyclopropyl |
| Cl | (2-) SO₂CH₃ | C₂H₅ | cyclopropyl |
| Cl | (2-) SO₂CH₃ | C₃H₇ | cyclopropyl |
| Cl | (2-) SO₂CH₃ | C₃H₇-i | cyclopropyl |
| Cl | (2-) SO₂CH₃ | C₄H₉ | cyclopropyl |
| Cl | (2-) SO₂CH₃ | C₄H₉-i | cyclopropyl |
| Cl | (2-) SO₂CH₃ | C₄H₉-s | cyclopropyl |
| Cl | (2-) SO₂CH₃ | C₄H₉-t | cyclopropyl |
| Cl | (2-) SO₂CH₃ | cyclopropyl | cyclopropyl |
| Cl | (2-) SO₂CH₃ | cyclopropylmethyl | cyclopropyl |
| Cl | (2-) SO₂CH₃ | CH=CHCH₃ | cyclopropyl |
| Cl | (2-) SO₂CH₃ | phenyl | cyclopropyl |
| Cl | (2-) SO₂CH₃ | 4-chlorophenyl | cyclopropyl |
| Cl | (2-) SO₂CH₃ | benzyl | cyclopropyl |
| Cl | (2-) SO₂CH₃ | N(CH₃)₂ | cyclopropyl |
| Cl | (2-) SO₂CH₃ | 4-methylmorpholin-yl | cyclopropyl |
| Cl | (2-) SO₂CH₃ | Cl | cyclopropyl |
| Cl | (2-) SO₂CH₃ | Br | cyclopropyl |
| Cl | (2-) Cl | CF₃ | N(CH₃)₂ |
| Cl | (2-) Cl | SCH₃ | N(CH₃)₂ |
| Cl | (2-) Cl | SC₂H₅ | N(CH₃)₂ |
| Cl | (2-) Cl | SC₃H₇ | N(CH₃)₂ |
| Cl | (2-) Cl | SC₃H₇-i | N(CH₃)₂ |
| Cl | (2-) Cl | SCH₂CH=CH₂ | N(CH₃)₂ |
| Cl | (2-) Cl | SCH₂C≡CH | N(CH₃)₂ |
| Cl | (2-) Cl | SCH=CHCH₃ | N(CH₃)₂ |
| Cl | (2-) Cl | SCH=CH₂ | N(CH₃)₂ |
| Cl | (2-) Cl | SCH₂-cyclopropyl | N(CH₃)₂ |
| Cl | (2-) Cl | SCH=C=CH₂ | N(CH₃)₂ |
| Cl | (2-) Cl | SCH₂CN | N(CH₃)₂ |
| Cl | (2-) Cl | SCH₂CH₂CN | N(CH₃)₂ |
| Cl | (2-) Cl | OCH₃ | N(CH₃)₂ |
| Cl | (2-) Cl | OC₂H₅ | N(CH₃)₂ |
| Cl | (2-) Cl | OC₃H₇ | N(CH₃)₂ |
| Cl | (2-) Cl | OC₃H₇-i | N(CH₃)₂ |
| Cl | (2-) Cl | OC₄H₉ | N(CH₃)₂ |
| Cl | (2-) Cl | OCH₂CF₃ | N(CH₃)₂ |
| Cl | (2-) Cl | OCH₂-cyclopropyl | N(CH₃)₂ |
| Cl | (2-) Cl | OC₆H₅ | N(CH₃)₂ |
| Cl | (2-) Cl | H | N(CH₃)₂ |
| Cl | (2-) Cl | CH₃ | N(CH₃)₂ |
| Cl | (2-) Cl | C₂H₅ | N(CH₃)₂ |
| Cl | (2-) Cl | C₃H₇ | N(CH₃)₂ |
| Cl | (2-) Cl | C₃H₇-i | N(CH₃)₂ |
| Cl | (2-) Cl | C₄H₉ | N(CH₃)₂ |

-continued

| R³ | (Position) (R⁴)ₙ | R⁵ | R⁶ |
|---|---|---|---|
| Cl | (2-) Cl | C₄H₉-i | N(CH₃)₂ |
| Cl | (2-) Cl | C₄H₉-s | N(CH₃)₂ |
| Cl | (2-) Cl | C₄H₉-t | N(CH₃)₂ |
| Cl | (2-) Cl | cyclopropyl-CH₂ | N(CH₃)₂ |
| Cl | (2-) Cl | cyclopropyl-CH₂CH₂ | N(CH₃)₂ |
| Cl | (2-) Cl | CH=CHCH₃ | N(CH₃)₂ |
| Cl | (2-) Cl | phenyl-CH₂ | N(CH₃)₂ |
| Cl | (2-) Cl | (4-Cl-phenyl)-CH₂ | N(CH₃)₂ |
| Cl | (2-) Cl | phenyl-CH₂CH₂ | N(CH₃)₂ |
| Cl | (2-) Cl | N(CH₃)₂ | N(CH₃)₂ |
| Cl | (2-) Cl | morpholinyl-CH₂ | N(CH₃)₂ |
| Cl | (2-) Cl | Cl | N(CH₃)₂ |
| Cl | (2-) Cl | Br | N(CH₃)₂ |
| SO₂CH₃ | (2-) Cl | CF₃ | N(CH₃)₂ |
| SO₂CH₃ | (2-) Cl | SCH₃ | N(CH₃)₂ |
| SO₂CH₃ | (2-) Cl | SC₂H₅ | N(CH₃)₂ |
| SO₂CH₃ | (2-) Cl | SC₃H₇ | N(CH₃)₂ |
| SO₂CH₃ | (2-) Cl | SC₃H₇-i | N(CH₃)₂ |
| SO₂CH₃ | (2-) Cl | SCH₂CH=CH₂ | N(CH₃)₂ |
| SO₂CH₃ | (2-) Cl | SCH₂C≡CH | N(CH₃)₂ |
| SO₂CH₃ | (2-) Cl | SCH=CHCH₃ | N(CH₃)₂ |
| SO₂CH₃ | (2-) Cl | SC≡CCH₃ | N(CH₃)₂ |
| SO₂CH₃ | (2-) Cl | S-CH₂-cyclopropyl | N(CH₃)₂ |
| SO₂CH₃ | (2-) Cl | SCH=C=CH₂ | N(CH₃)₂ |
| SO₂CH₃ | (2-) Cl | SCH₂CN | N(CH₃)₂ |
| SO₂CH₃ | (2-) Cl | SCH₂CH₂CN | N(CH₃)₂ |
| SO₂CH₃ | (2-) Cl | OCH₃ | N(CH₃)₂ |
| SO₂CH₃ | (2-) Cl | OC₂H₅ | N(CH₃)₂ |
| SO₂CH₃ | (2-) Cl | OC₃H₇ | N(CH₃)₂ |
| SO₂CH₃ | (2-) Cl | OC₃H₇-i | N(CH₃)₂ |
| SO₂CH₃ | (2-) Cl | OC₄H₉ | N(CH₃)₂ |
| SO₂CH₃ | (2-) Cl | OCH₂CF₃ | N(CH₃)₂ |
| SO₂CH₃ | (2-) Cl | O-CH₂-cyclopropyl | N(CH₃)₂ |
| SO₂CH₃ | (2-) Cl | OC₆H₅ | N(CH₃)₂ |
| SO₂CH₃ | (2-) Cl | H | N(CH₃)₂ |
| SO₂CH₃ | (2-) Cl | CH₃ | N(CH₃)₂ |
| SO₂CH₃ | (2-) Cl | C₂H₅ | N(CH₃)₂ |
| SO₂CH₃ | (2-) Cl | C₃H₇ | N(CH₃)₂ |
| SO₂CH₃ | (2-) Cl | C₃H₇-i | N(CH₃)₂ |
| SO₂CH₃ | (2-) Cl | C₄H₉ | N(CH₃)₂ |
| SO₂CH₃ | (2-) Cl | C₄H₉-i | N(CH₃)₂ |
| SO₂CH₃ | (2-) Cl | C₄H₉-s | N(CH₃)₂ |
| SO₂CH₃ | (2-) Cl | C₄H₉-t | N(CH₃)₂ |
| SO₂CH₃ | (2-) Cl | cyclopropyl-CH₂ | N(CH₃)₂ |
| SO₂CH₃ | (2-) Cl | cyclopropyl-CH₂CH₂ | N(CH₃)₂ |
| SO₂CH₃ | (2-) Cl | CH=CHCH₃ | N(CH₃)₂ |
| SO₂CH₃ | (2-) Cl | phenyl-CH₂ | N(CH₃)₂ |
| SO₂CH₃ | (2-) Cl | (4-Cl-phenyl)-CH₂ | N(CH₃)₂ |
| SO₂CH₃ | (2-) Cl | phenyl-CH₂CH₂ | N(CH₃)₂ |
| SO₂CH₃ | (2-) Cl | N(CH₃)₂ | N(CH₃)₂ |
| SO₂CH₃ | (2-) Cl | morpholinyl-CH₂ | N(CH₃)₂ |
| SO₂CH₃ | (2-) Cl | Cl | N(CH₃)₂ |
| SO₂CH₃ | (2-) Cl | Br | N(CH₃)₂ |
| Cl | (2-) SO₂CH₃ | CF₃ | N(CH₃)₂ |
| Cl | (2-) SO₂CH₃ | SCH₃ | N(CH₃)₂ |
| Cl | (2-) SO₂CH₃ | SC₂H₅ | N(CH₃)₂ |
| Cl | (2-) SO₂CH₃ | SC₃H₇ | N(CH₃)₂ |

-continued

| R³ | (Position) (R⁴)ₙ | R⁵ | R⁶ |
|---|---|---|---|
| Cl | (2-) SO₂CH₃ | SC₃H₇-i | N(CH₃)₂ |
| Cl | (2-) SO₂CH₃ | –SCH₂CH=CH₂ | N(CH₃)₂ |
| Cl | (2-) SO₂CH₃ | –SCH₂C≡CH | N(CH₃)₂ |
| Cl | (2-) SO₂CH₃ | –SCH=CHCH₃ | N(CH₃)₂ |
| Cl | (2-) SO₂CH₃ | –SC≡CCH₃ | N(CH₃)₂ |
| Cl | (2-) SO₂CH₃ | –SCH₂–(cyclopropyl) | N(CH₃)₂ |
| Cl | (2-) SO₂CH₃ | SCH=C=CH₂ | N(CH₃)₂ |
| Cl | (2-) SO₂CH₃ | SCH₂CN | N(CH₃)₂ |
| Cl | (2-) SO₂CH₃ | SCH₂CH₂CN | N(CH₃)₂ |
| Cl | (2-) SO₂CH₃ | OCH₃ | N(CH₃)₂ |
| Cl | (2-) SO₂CH₃ | OC₂H₅ | N(CH₃)₂ |
| Cl | (2-) SO₂CH₃ | OC₃H₇ | N(CH₃)₂ |
| Cl | (2-) SO₂CH₃ | OC₃H₇-i | N(CH₃)₂ |
| Cl | (2-) SO₂CH₃ | OC₄H₉ | N(CH₃)₂ |
| Cl | (2-) SO₂CH₃ | OCH₂CF₃ | N(CH₃)₂ |
| Cl | (2-) SO₂CH₃ | –OCH₂–(cyclopropyl) | N(CH₃)₂ |
| Cl | (2-) SO₂CH₃ | OC₆H₅ | N(CH₃)₂ |
| Cl | (2-) SO₂CH₃ | H | N(CH₃)₂ |
| Cl | (2-) SO₂CH₃ | CH₃ | N(CH₃)₂ |
| Cl | (2-) SO₂CH₃ | C₂H₅ | N(CH₃)₂ |
| Cl | (2-) SO₂CH₃ | C₃H₇ | N(CH₃)₂ |
| Cl | (2-) SO₂CH₃ | C₃H₇-i | N(CH₃)₂ |
| Cl | (2-) SO₂CH₃ | C₄H₉ | N(CH₃)₂ |
| Cl | (2-) SO₂CH₃ | C₄H₉-i | N(CH₃)₂ |
| Cl | (2-) SO₂CH₃ | C₄H₉-s | N(CH₃)₂ |
| Cl | (2-) SO₂CH₃ | C₄H₉-t | N(CH₃)₂ |
| Cl | (2-) SO₂CH₃ | cyclopropyl | N(CH₃)₂ |
| Cl | (2-) SO₂CH₃ | –CH₂–(cyclopropyl) | N(CH₃)₂ |
| Cl | (2-) SO₂CH₃ | CH=CHCH₃ | N(CH₃)₂ |
| Cl | (2-) SO₂CH₃ | phenyl | N(CH₃)₂ |
| Cl | (2-) SO₂CH₃ | 4-chlorophenyl | N(CH₃)₂ |
| Cl | (2-) SO₂CH₃ | benzyl (–CH₂C₆H₅) | N(CH₃)₂ |
| Cl | (2-) SO₂CH₃ | N(CH₃)₂ | N(CH₃)₂ |
| Cl | (2-) SO₂CH₃ | 4-methylmorpholin-4-yl | N(CH₃)₂ |
| Cl | (2-) SO₂CH₃ | Cl | N(CH₃)₂ |
| Cl | (2-) SO₂CH₃ | Br | N(CH₃)₂ |
| Cl | (2-) Cl | CH₃ | OCH₃ |
| Cl | (2-) Cl | C₂H₅ | OCH₃ |
| Cl | (2-) Cl | C₃H₇ | OCH₃ |
| Cl | (2-) Cl | SCH₃ | OCH₃ |
| Cl | (2-) Cl | SC₂H₅ | OCH₃ |
| Cl | (2-) Cl | OCH₃ | OCH₃ |
| Cl | (2-) Cl | OC₂H₅ | OCH₃ |
| Cl | (2-) Cl | CH₃ | OC₂H₅ |
| Cl | (2-) Cl | C₂H₅ | OC₂H₅ |
| Cl | (2-) Cl | C₃H₇ | OC₂H₅ |
| Cl | (2-) Cl | SCH₃ | OC₂H₅ |
| Cl | (2-) Cl | SC₂H₅ | OC₂H₅ |
| Cl | (2-) Cl | OCH₃ | OC₂H₅ |
| Cl | (2-) Cl | OC₂H₅ | OC₂H₅ |
| Cl | (2-) SO₂CH₃ | CH₃ | OCH₃ |
| Cl | (2-) SO₂CH₃ | C₂H₅ | OCH₃ |
| Cl | (2-) SO₂CH₃ | C₃H₇ | OCH₃ |
| Cl | (2-) SO₂CH₃ | SCH₃ | OCH₃ |
| Cl | (2-) SO₂CH₃ | SC₂H₅ | OCH₃ |
| Cl | (2-) SO₂CH₃ | OCH₃ | OCH₃ |
| Cl | (2-) SO₂CH₃ | OC₂H₅ | OCH₃ |
| Cl | (2-) SO₂CH₃ | CH₃ | OC₂H₅ |
| Cl | (2-) SO₂CH₃ | C₂H₅ | OC₂H₅ |
| Cl | (2-) SO₂CH₃ | C₃H₇ | OC₂H₅ |
| Cl | (2-) SO₂CH₃ | SCH₃ | OC₂H₅ |
| Cl | (2-) SO₂CH₃ | SC₂H₅ | OC₂H₅ |
| Cl | (2-) SO₂CH₃ | OCH₃ | OC₂H₅ |
| Cl | (2-) SO₂CH₃ | OC₂H₅ | OC₂H₅ |
| SO₂CH₃ | (2-) Cl | Cl | OCH₃ |
| SO₂CH₃ | (2-) Cl | Br | OCH₃ |
| SO₂CH₃ | (2-) Cl | CH₃ | OCH₃ |
| SO₂CH₃ | (2-) Cl | C₂H₅ | OCH₃ |
| SO₂CH₃ | (2-) Cl | C₃H₇ | OCH₃ |
| SO₂CH₃ | (2-) Cl | SCH₃ | OCH₃ |
| SO₂CH₃ | (2-) Cl | SC₂H₅ | OCH₃ |
| SO₂CH₃ | (2-) Cl | OCH₃ | OC₂H₅ |
| SO₂CH₃ | (2-) Cl | OC₂H₅ | OC₂H₅ |
| SO₂CH₃ | (2-) Cl | CH₃ | OC₂H₅ |
| SO₂CH₃ | (2-) Cl | C₂H₅ | OC₂H₅ |
| SO₂CH₃ | (2-) Cl | C₃H₇ | OC₂H₅ |
| SO₂CH₃ | (2-) Cl | SCH₃ | OC₂H₅ |
| SO₂CH₃ | (2-) Cl | SC₂H₅ | OC₂H₅ |
| SO₂CH₃ | (2-) Cl | OCH₃ | OC₂H₅ |

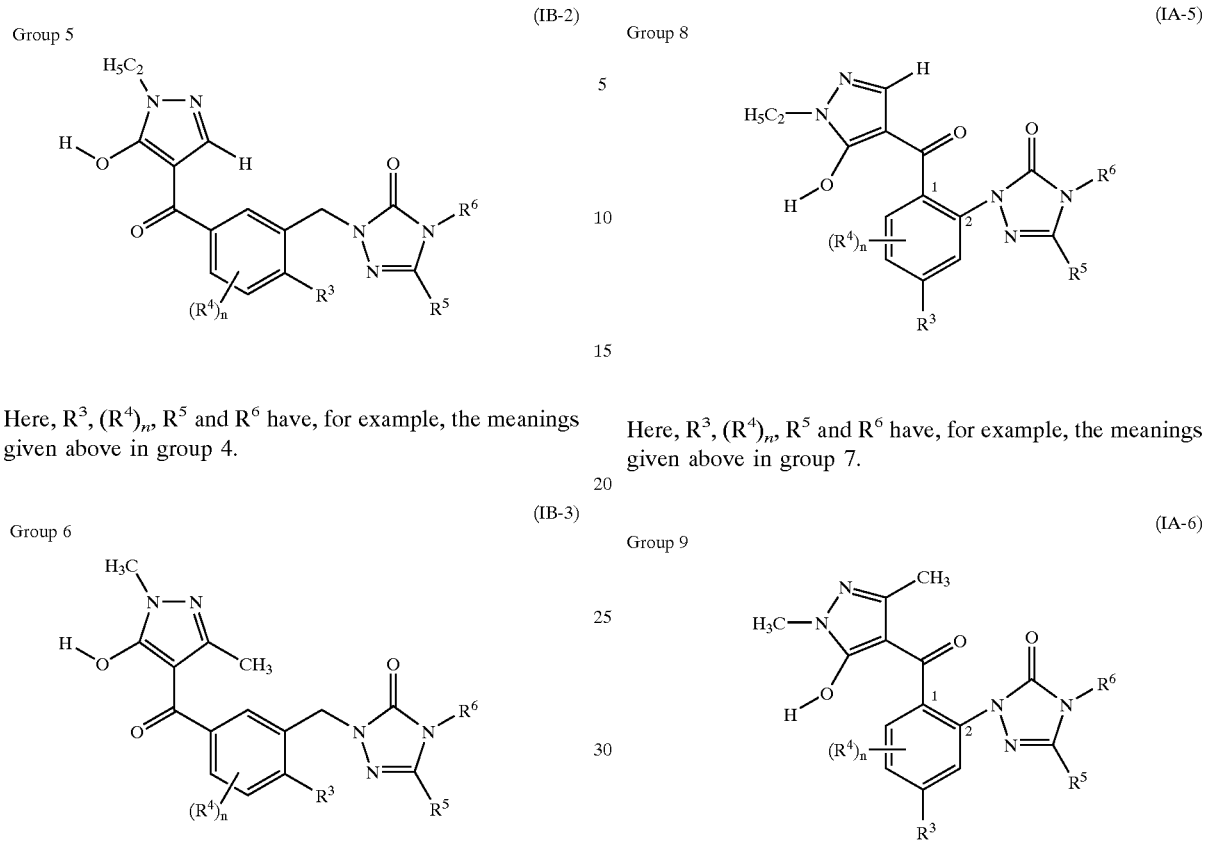

Group 5 (IB-2)

Here, $R^3$, $(R^4)_n$, $R^5$ and $R^6$ have, for example, the meanings given above in group 4.

Group 6 (IB-3)

Here $R^3$, $(R^4)_n$, $R^5$ and $R^6$ have, for example, the meanings given above in group 4.

Group 7 (IA-4)

Here, $R^3$, $(R^4)_n$, $R^5$ and $R^6$ have, for example, the meanings given in the table below:

| $R^3$ | (Position) $(R^4)_n$ | $R^5$ | $R^6$ |
|---|---|---|---|
| H | — | $CF_3$ | $CH_3$ |
| F | — | $CF_3$ | $CH_3$ |
| Cl | — | $CF_3$ | $CH_3$ |
| Br | — | $CF_3$ | $CH_3$ |

Group 8 (IA-5)

Here, $R^3$, $(R^4)_n$, $R^5$ and $R^6$ have, for example, the meanings given above in group 7.

Group 9 (IA-6)

Here, $R^3$, $(R^4)_n$, $R^5$ and $R^6$ have, for example, the meanings given above in group 7.

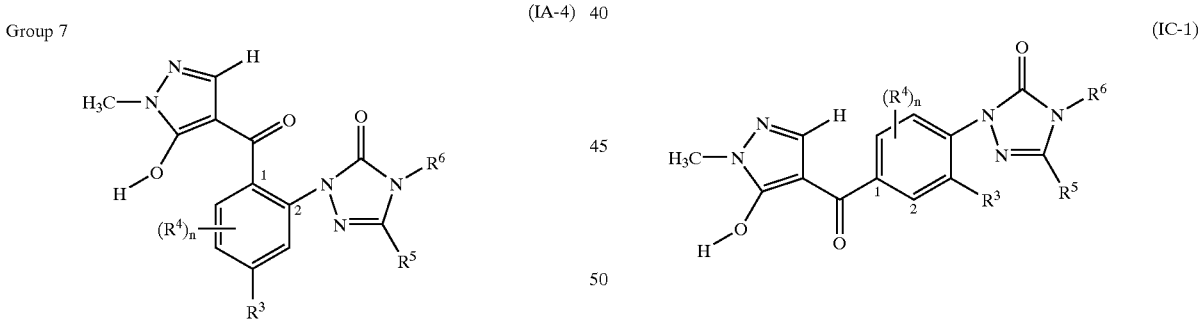

(IC-1)

Here, $R^3$, $(R^4)_n$, $R^5$ and $R^6$ have, for example, the meanings given in the table below:

| $R^3$ | (Position) $(R^4)_n$ | $R^5$ | $R^6$ |
|---|---|---|---|
| H | (2-) F | $CF_3$ | $CH_3$ |
| H | (2-) Cl | $CF_3$ | $CH_3$ |
| H | (2-) Br | $CF_3$ | $CH_3$ |
| H | — | $CF_3$ | $CH_3$ |

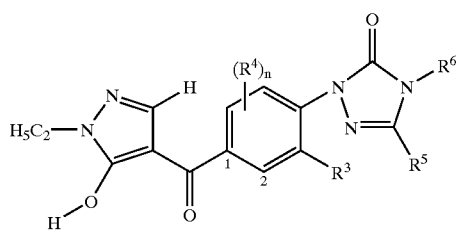
(IC-2)

Here, $R^3$, $(R^4)_n$, $R^5$ and $R^6$ have, for example, the meanings given above in group 10.

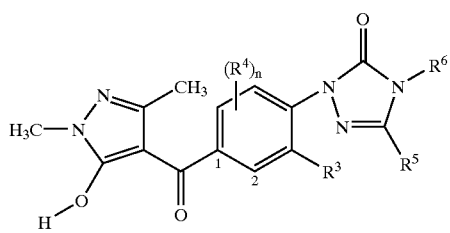
(IC-3)

Here, $R^3$, $(R^4)_n$, $R^5$ and $R^6$ have, for example, the meanings given above in group 10.

The novel substituted benzoylpyrazoles of the general formula (I) have strong and selective herbicidal activity.

Novel substituted benzoylpyrazoles of the general formula (I) are obtained when (a) pyrazoles of the general formula (II)

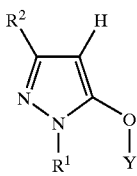
(II)

in which
$R^1$, $R^2$ and Y are as defined above,
are reacted with substituted benzoic acids of the general formula (III),

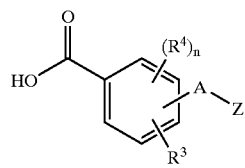
(III)

in which
n, A, $R^3$, $R^4$ and Z are as defined above,
in the presence of a dehydrating agent, if appropriate in the presence of one or more reaction auxiliaries and if appropriate in the presence of a diluent, or when (b) pyrazoles of the general formula (II)

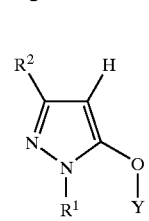
(II)

in which
$R^1$, $R^2$ and Y are as defined above,
are reacted with substituted benzoic acid derivatives of the general formula (IV)

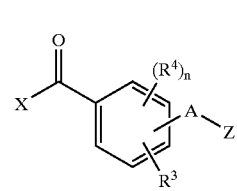
(IV)

in which
n, A, $R^3$, $R^4$ and Z are as defined above, and
X represents cyano, halogen or alkoxy,
—or with corresponding carboxylic anhydrides—
if appropriate in the presence of one or more reaction auxiliaries and if appropriate in the presence of a diluent, or when (c) substituted benzoylpyrazoles of the general formula (Ia)

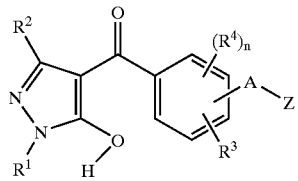
(Ia)

in which
n, A, $R^1$, $R^2$, $R^3$, $R^4$ and Z are as defined above,
are reacted with compounds of the general formula (V)

H—Y (V)

in which
Y is as defined above, except for hydrogen,
—or, if appropriate, with corresponding isocyanates or isothiocyanates—
if appropriate in the presence of one or more reaction auxiliaries and if appropriate in the presence of a diluent,
and, if appropriate, the resulting compounds of the formula (I) are subsequently subjected in a customary manner to electrophilic or nucleophilic and/or oxidation or reduction reactions within the scope of the definition of the substituents, or the compounds of the formula (I) are converted in a customary manner into salts.

The compounds of the formula (I) can be converted by customary methods into other compounds of the formula (I) in accordance with the above definition, for example by nucleophilic substitution (for example $R^5$: Cl→$OC_2H_5$, $SCH_3$) or by oxidation (for example $R^5$: $CH_2SCH_3$→$CH_2S(O)CH_3$).

Using, for example, 3-chloro-5-hydroxy-1-methyl-pyrazole and 2-(3-carboxy-5-fluoro-benzyl)-5-ethyl-4-methoxy-2,4-dihydro-3H-1,2,4-triazol-3-one as starting materials, the course of the reaction in the process (a) according to the invention can be illustrated by the following formula scheme:

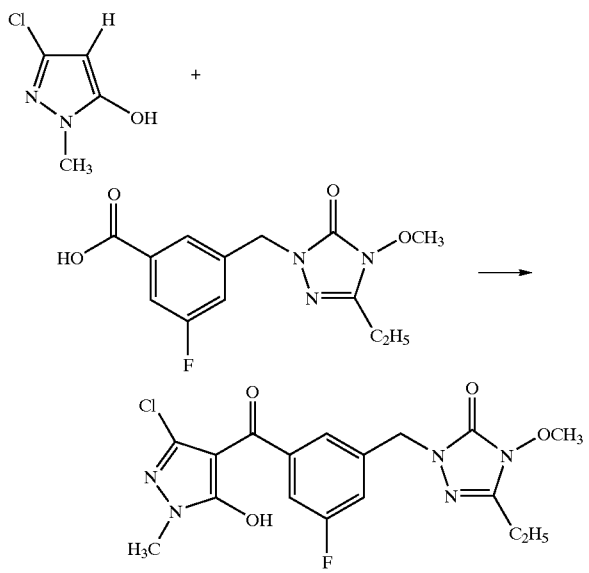

Using, for example, 3-cyano-5-hydroxy-1-ethyl-pyrazole and 2-(3-methoxycarbonyl-5-chloro-benzyl)-4-ethyl-5-methylthio-2,4-dihydro-3H-2,4-triazol-3-one as starting materials, the course of the reaction in the process (b) according to the invention can be illustrated by the following formula scheme:

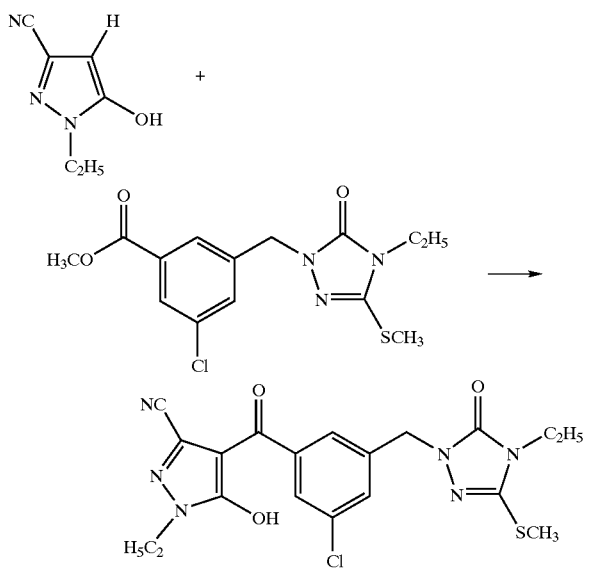

Using, for example, 4-methyl-5-trifluoromethyl-2-[3-chloro-4-(1-ethyl-5-hydroxy-pyrazol-4-yl-carbonyl)-phenyl-]2,4-triazol-3H-1,2,4-triazo-3-one and benzoyl chloride as starting materials, the course of the reaction in the process (c) according to the invention can be illustrated by the following formula scheme:

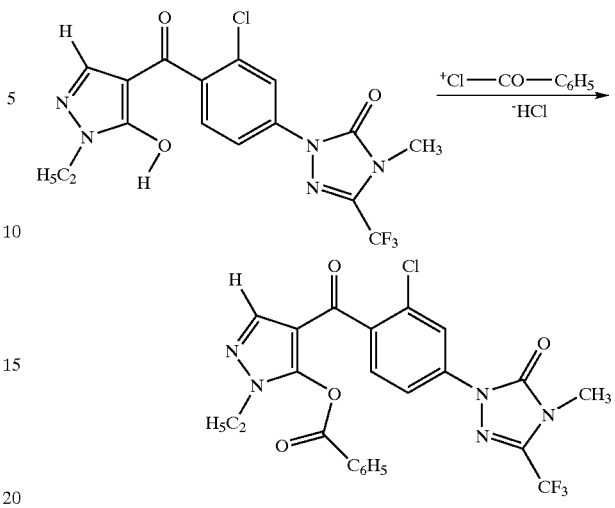

The formula (II) provides a general definition of the pyrazoles to be used as starting materials in the process (a) according to the invention for preparing compounds of the general formula (I). In the general formula (II), $R^1$, $R^2$ and Y preferably have those meanings which have already been mentioned above, in connection with the description of the compounds of the general formula (I) according to the invention, as being preferred, particularly preferred, very particularly preferred or most preferred for $R^1$, $R^2$ and Y.

The starting materials of the general formula (II) are known and/or can be prepared by processes known per se (cf. EP-A-240001).

The formula (III) provides a general definition of the benzoic acids further to be used as starting materials in the process (a) according to the invention. In the formula (III), n, A, $R^3$, $R^4$ and Z preferably have those meanings which have already been mentioned above, in connection with the description of the compounds of the formula (I) according to the invention, as being preferred, particularly preferred, very particularly preferred or most preferred for n, A, $R^3$, $R^4$ and Z.

Except for 2-(5-carboxy-2,4dichlorophenyl)-4-difluoromethyl-5-methyl-2,4-dihydro-3H-1,2,4-triazol-3-one—alias 2,4-dichloro-5-(4-difluoromethyl-4,5-dihydro-3-methyl-5-oxo-1H-1,2,4-triazol-1-yl)-benzoic acid (CAS Reg. No. 90208-77-8) and 2-(5-carboxy-2,4-dichloro-phenyl)-4,5-dimethyl-2,4-dihydro-3H-1,2,4-triazol-3-one—alias 2,4-dichloro-5-(4,5-dihydro-3,4-dimethyl-5-oxo-1H-1,2,4-triazol-1-yl)-benzoic acid (CAS Reg. No. 90208-76-7)—the starting materials of the general formula (III) have hitherto not been disclosed in the literature. However, except for 2-(5-carboxy-2,4-dichloro-phenyl)-4-difluoromethyl-5-methyl-2,4-dihydro-3H-1,2,4-triazol-3-one and 2-(5-carboxy-2,4-dichloro-phenyl)-4,5-dimethyl-2,4-dihydro-3H-1,2,4-triazol-3-one (cf. JP-A-58225070—cited in Chem. Abstracts 100:209881, JP-A-02015069—cited in Chem. Abstracts 113:23929), they are the subject of an earlier application which, however, has not been published earlier (cf. DE-A-19833360).

The substituted benzoic acids of the general formula (III) are obtained when benzoic acid derivatives of the general formula (VI)

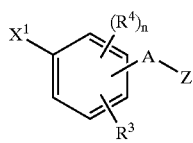

(VI)

in which
- n, A, R³ and R⁴ and Z are as defined above, and
- X¹ represents cyano, carbamoyl, halogenocarbonyl or alkoxycarbonyl,
- are reacted with water, if appropriate in the presence of a hydrolysis auxiliary, such as, for example, sulfuric acid, at temperatures between 50° C. and 120° C. (cf. the Preparation Examples).

The formula (IV) provides a general definition of the substituted benzoic acid derivatives to be used as starting materials in the process (b) according to the invention for preparing compounds of the general formula (I). In the general formula (IV), n, A, R³, R⁴ and Z preferably have those meanings which have already been mentioned above, in connection with the description of the compounds of the general formula (I) according to the invention, as being preferred, particularly preferred, very particularly preferred or most preferred for n, A, R³, R⁴ and Z; X preferably represents cyano, fluorine, chlorine, bromine or $C_1$–$C_4$-alkoxy, in particular chlorine, methoxy or ethoxy.

The starting materials of the general formula (IV)—and the precursors of the general formula (VI)—are known and/or can be prepared by processes known per se (cf. DE-A-3839480, DE-A-4239296, EP-A-597360, EP-A-609734, DE-A-4303676, EP-A-617026, DE-A-4405614, U.S. Pat. No. 5,378,681).

The formula (Ia) provides a general definition of the substituted benzoylpyrazoles to be used as starting materials in the process (c) according to the invention for preparing compounds of the general formula (I). In the general formula (Ia), n, A, R¹, R², R³, R⁴ and Z preferably have those meanings which have already been mentioned above, in connection with the description of the compounds of the general formula (I) according to the invention, as being preferred, particularly preferred, very particularly preferred or most preferred for n, A, R¹, R², R³, R⁴ and Z.

The starting materials of the general formula (Ia) are novel compounds according to the invention; they can be prepared by the processes (a) and (b) according to the invention.

The formula (V) provides a general definition of the compounds further to be used as starting materials in the [lacuna] (c) according to the invention. In the general formula (V), Y preferably has that meaning which has already been mentioned above, in connection with the description of the compounds of the general formula (I) according to the invention, as being preferred, particularly preferred, very particularly preferred or most preferred for Y.

The starting materials of the general formula (V) are known chemicals for synthesis.

The process (a) according to the invention for preparing the novel substituted benzoylpyrazoles of the general formula (I) is carried out using a dehydrating agent. Suitable dehydrating agents are the customary chemicals suitable for binding water.

Examples which may be mentioned are dicyclohexylcarbodiimide and carbonyl-bis-imidazole.

A particularly suitable dehydrating agent which may be mentioned is dicyclohexylcarbodiimide.

The process (a) according to the invention for preparing the novel substituted benzoylpyrazoles of the general formula (I) is, if appropriate, carried out using a reaction auxiliary.

Examples of suitable reaction auxiliaries which may be mentioned are sodium cyanide, potassium cyanide, acetone cyanohydrin, 2-cyano-2-(trimethylsilyloxy)-propane and trimethylsilyl cyanide.

A particularly suitable reaction auxiliary which may be mentioned is trimethylsilyl cyanide.

The process (b) according to the invention for preparing the novel substituted benzoylpyrazoles of the general formula (I) is, if appropriate, carried out using reaction auxiliaries.

Examples of suitable reaction auxiliaries which may be mentioned are (conc.) sulfuric acid, zinc chloride, aluminum chloride, and boron fluoride.

The processes according to the invention for preparing the novel substituted benzoylpyrazoles of the general formula (I) are, if appropriate, carried out using further reaction auxiliaries. Suitable (further) reaction auxiliaries for the processes according to the invention are, in general, basic organic nitrogen compounds, such as, for example, trimethylamine, triethylamine, tri-propylamine, tributylamine, ethyl-di-isopropylamine, N,N-dimethyl-cyclohexylamine, dicyclohexylamine, ethyldicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

Suitable diluents for carrying out the processes (a), (b) and (c) according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride or 1,4dichloro-ethane; ethers, such as diethyl ether, diisopropyl ether, dioxane, tetrahydrofuran, ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulfoxides, such as dimethyl sulfoxide.

When carrying out the processes (a), (b) and (c) according to the invention, the reaction temperatures can be varied within a relatively wide range. In general, the processes are carried out at temperatures between 0° C. and 150° C., preferably between 10° C. and 120° C.

The processes (a), (b) and (c) according to the invention are generally carried out under atmospheric pressure. However, it is also possible to carry out the processes according to the invention under elevated or reduced pressure—in general between 0.1 bar and 10 bar.

For carrying out the processes (a), (b) and (c) according to the invention, the starting materials are generally employed in approximately equimolar amounts. However, it is also possible to use a relatively large excess of one of the components. The reaction is generally carried out in a suitable diluent in the presence of a dehydrating agent, and the reaction mixture is generally stirred for a number of hours at the required temperature. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

According to the invention, it is possible to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including transgenic plants and including plant varieties which may or may not be protected by plant variety protection rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include crops, and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing on and, in the case of propagation material, in particular in the case of seeds, furthermore by single- or multi-layer coating.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitania, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera, Aegilops, Phalaris.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

Depending on the concentration, the active compounds according to the invention are suitable for total weed control, for example on industrial terrain and rail tracks and on paths and areas with or without tree growth. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when applied to the soil and on above-ground parts of plants. To a certain extent, they are also suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspoemulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulfoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates and protein hydrolyzates; suitable dispersants are: for example lignosulfite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlortoluron, cinidon(-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamnid, diquat, dithiopyr, diuron, dymron, epoprodan, ETPC, esprocarb, ethalfluralin, ethametsulfuron(-methyl), ethofumesate, ethoxyfen, ethoxysulfuron, etobenzanid, fenoxaprop(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz(-methyl), imazamelhapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonsaure, pendimethalin, pentoxazone, phenmediphaam, picolinafen, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin, triflusulfuron and tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

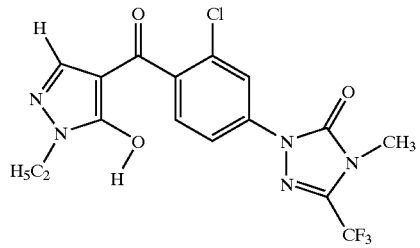

At room temperature (about 20° C.), a mixture of 1.64 g (5 mmol) of 4-methyl-5-trifluoromethyl-2-(3-chloro-4-carboxy-phenyl)-2,4-dihydro-3H-1,2,4-triazol-3-one, 0.62 g (5.5 mmol) of 1-ethyl-5-hydroxy-pyrazole and 40 ml of acetonitrile is admixed with stirring with 1.13 g (5.5 mmol) of dicyclohexylcarbodiimide, and the reaction mixture is stirred at room temperature for 16 hours. 1.0 g (10 mmol) of triethylamine and 0.2 g (2 mmol) of trimethylsilyl cyanide are then added, and the mixture is stirred at room temperature for three days. 60 ml of a 2% strength aqueous sodium carbonate solution are then added, and the mixture is stirred at room temperature for three hours. The precipitated dicyclohexylurea is removed by filtration with suction, and the mother liquor is extracted twice with diethyl ether. With stirring, the aqueous phase is adjusted by addition of conc. hydrochloric acid to a pH of about 1. The oily product that separates off during the addition is extracted with methylene chloride, and the extraction solution is dried with magnesium sulfate and filtered. From the filtrate, the solvent is carefully distilled off under waterpump vacuum.

This gives 1.5 g (72% of theory) of 4-methyl-5-trfluoromethyl-2-[3-chloro-4-(1-ethyl-5-hydroxy-pyrazol-4-carbonyl)-phenyl]-2,4-dihydro-3H-1,2,4-triazol-3-one as an amorphous product.

logP (determined at pH≈2): 2.63.

Similarly to Example 1, and in accordance with the general description of the preparation process according to the invention, it is also possible to prepare, for example, the compounds of the general formula (I)—or those of the formulae (IA), (IB) or (IC)—listed in Table 1 below.

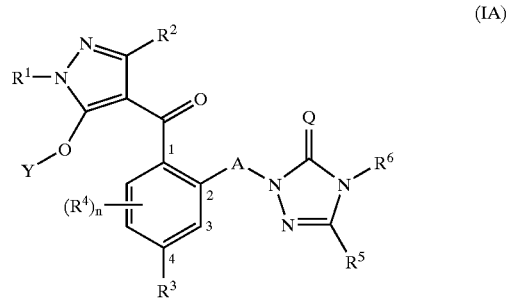

(IA)

-continued

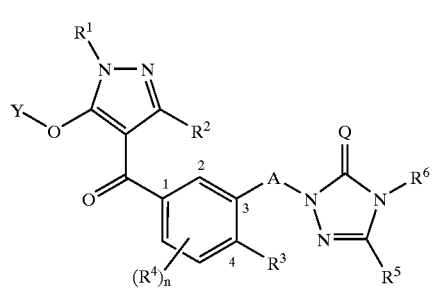

(IB)

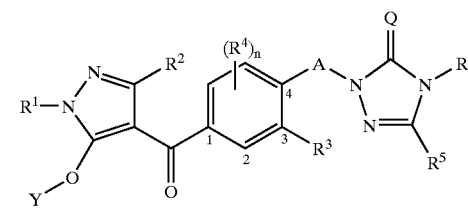

(IC)

TABLE 1

Examples of the compounds of the formula (I), (IA), (IB),(IC)
Here, Y in each case represents hydrogen

| Ex. No. | A | Q | $R^1$ | $R^2$ | $R^3$ | (Position) $(R^4)_n$ | $R^5$ | $R^6$ | (Formula) Physical data |
|---|---|---|---|---|---|---|---|---|---|
| 2 | $CH_2$ | O | $C_2H_5$ | H | $CF_3$ | — | $OC_2H_5$ | $CH_3$ | (IA) logP = 2.34[a] |
| 3 | $CH_2$ | O | $C_2H_5$ | H | $CF_3$ | — | $SCH_3$ | $CH_3$ | (IA) logP = 2.22[a] |
| 4 | $CH_2$ | O | $C_2H_5$ | H | $SO_2CH_3$ | — | $SCH_3$ | $CH_3$ | (IA) logP = 1.24[a] |
| 5 | $CH_2$ | O | $C_2H_5$ | H | $CF_3$ | — | $SC_2H_5$ | $CH_3$ | (IA) logP = 2.58[a] |
| 6 | $CH_2$ | O | $C_2H_5$ | H | $CF_3$ | — | $SC_3H_7$-i | $CH_3$ | (IA) logP = 2.90[a] |
| 7 | $CH_2$ | O | $C_2H_5$ | H | $CF_3$ | — | $OCH_3$ | cyclopropyl | (IA) logP = 2.28[a] |
| 8 | $CH_2$ | O | $C_2H_5$ | H | F | — | $N(CH_3)_2$ | $CH_3$ | (IA) logP = 1.61[a] |
| 9 | $CH_2$ | O | $CH_3$ | $CH_3$ | F | — | $N(CH_3)_2$ | $CH_3$ | (IA) logP = 1.32[a] |
| 10 | $CH_2$ | O | $CH_3$ | $CH_3$ | F | — | $OCH_3$ | cyclopropyl | (IA) logP = 1.50[a] |
| 11 | $CH_2$ | O | $CH_3$ | $CH_3$ | F | — | $OC_2H_5$ | cyclopropyl | (IA) logP = 1..80[a] |
| 12 | $CH_2$ | O | $C_2H_5$ | H | Br | — | $CH_2=CHCH_2S$- | $CH_3$ | (IA) logP = 2.69[a] |
| 13 | — | O | $C_2H_5$ | H | H | (6-) $CF_3$ | $CF_3$ | $CH_3$ | (IB) logP = 2.83[a] |
| 14 | — | O | $C_2H_5$ | H | H | (2-) Cl | $CH_3$ | $CH_3$ | (IC) logP = 1.71[a] |
| 15 | — | O | $C_2H_5$ | H | H | — | $CF_3$ | $CH_3$ | (IA) logP = 1.95[a] |
| 16 | — | O | $C_2H_5$ | H | Cl | — | $CF_3$ | $CH_3$ | (IA) logP = 2.47[a] |
| 17 | $CH_2$ | O | $C_2H_5$ | H | Cl | (2-) Cl | $CF_3$ | $CH_3$ | (IB) logP = 2.30[a] |
| 18 | $CH_2$ | O | $C_2H_5$ | H | Cl | (2-) Cl | $SCH_3$ | $CH_3$ | (IB) logP = 1.91[a] |
| 19 | $CH_2$ | O | $C_2H_5$ | H | Cl | (2-) Cl | $OC_2H_5$ | $CH_3$ | (IB) logP = 2.01[a] |
| 20 | $CH_2$ | O | $C_2H_5$ | H | Cl | (2-) Cl | cyclopropyl | cyclopropyl | (IB) logP = 2.14[a] |

TABLE 1-continued

Examples of the compounds of the formula (I), (IA), (IB),(IC)
Here, Y in each case represents hydrogen

| Ex. No. | A | Q | $R^1$ | $R^2$ | $R^3$ | (Position) $(R^4)_n$ | $R^5$ | $R^6$ | (Formula) Physical data |
|---|---|---|---|---|---|---|---|---|---|
| 21 | $CH_2$ | O | $C_2H_5$ | H | Cl | (2-) Cl | $OCH_3$ | $CH_3$ | (IB) logP = 1.69[a] |
| 22 | $CH_2$ | O | $C_2H_5$ | H | Cl | (2-) Cl | $OC_3H_7$-i | $CH_3$ | (IB) logP = 2.31[a] |
| 23 | $CH_2$ | O | $C_2H_5$ | H | Cl | (2-) Cl | $OCH_2CF_3$ | $CH_3$ | (IB) logP = 2.33[a] |
| 24 | $CH_2$ | O | $C_2H_5$ | H | Cl | (2-) Cl | Br | $CH_3$ | (IB) logP = 1.81[a] |
| 25 | $CH_2$ | O | $C_2H_5$ | H | Cl | (2-) Cl | H | $CH_3$ | (IB) logP = 1.28[a] |
| 26 | $CH_2$ | O | $C_2H_5$ | H | Cl | (2-) Cl |  | $CH_3$ | (IB) logP = 1.82[a] |
| 27 | — | O | $C_2H_5$ | H | Br | — | $CF_3$ | $CH_3$ | (IA) logP = 2.55[a] |
| 28 | $CH_2$ | O | $C_2H_5$ | H | Cl | (2-) Cl | $N(CH_3)_2$ | $CH_3$ | (IB) logP = 1.77[a] |
| 29 | $CH_2$ | O | $C_2H_5$ | H | Cl | (2-) Cl | $CH_3$ | $CH_3$ | (IB) logP = 1.38[a] |
| 30 | $CH_2$ | O | $C_2H_5$ | H | Cl | (2-) Cl | $R^5 + R^6$: $(CH_2)_4$ | $(cF.R^5)$ | (IB) logP = 1.55[a] |
| 31 | $CH_2$ | O | $C_2H_5$ | H | Cl | (2-) Cl | $OCH_3$ | 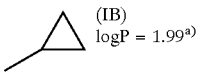 | (IB) logP = 1.99[a] |
| 32 | $CH_2$ | O | $C_2H_5$ | H | Cl | (2-) Cl | $OC_2H_5$ | 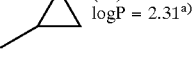 | (IB) logP = 2.31[a] |
| 33 | $CH_2$ | O | $C_2H_5$ | H | Cl | (2-) Cl | $OC_3H_7$-i | 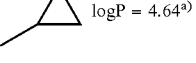 | (IB) logP = 4.64[a] |
| 34 | $CH_2$ | O | $C_2H_5$ | H | Cl | (2-) Cl | $OCH_2CF_3$ | 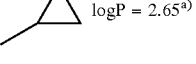 | (IB) logP = 2.65[a] |
| 35 | $CH_2$ | O | $C_2H_5$ | H | Cl | (2-) Cl | $SCH_3$ | 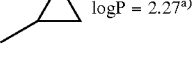 | (IB) logP = 2.27[a] |
| 36 | $CH_2$ | O | $C_2H_5$ | H | Cl | (2-) Cl | $CH_3$ | 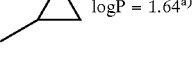 | (IB) logP = 1.64[a] |
| 37 | $CH_2$ | O | $C_2H_5$ | H | Cl | (2-) Cl | $N(CH_3)_2$ | 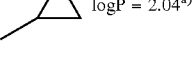 | (IB) logP = 2.04[a] |
| 38 | $CH_2$ | O | $C_2H_5$ | H | Cl | (2-) Cl | $C_2H_5$ | $OC_2H_5$ | (IB) logP = 2.16[a] |
| 39 | $CH_2$ | O | $CH_3$ | $CH_3$ | Cl | (2-) Cl | Br | $CH_3$ | (IB) logP = 1.52[a] |

TABLE 1-continued

Examples of the compounds of the formula (I), (IA), (IB),(IC)
Here, Y in each case represents hydrogen

| Ex. No. | A | Q | R¹ | R² | R³ | (Position) (R⁴)ₙ | R⁵ | R⁶ | (Formula) Physical data |
|---|---|---|---|---|---|---|---|---|---|
| 40 | $CH_2$ | O | $CH_3$ | H | Cl | (2-) Cl | Br | $CH_3$ | (IB) logP = 1.53[a] |
| 41 | $CH_2$ | O | $C_2H_5$ | $CH_3$ | Cl | (2-) Cl | $SCH_3$ | $CH_3$ | (IB) logP = 1.91[a] |
| 42 | $CH_2$ | O | $C_2H_5$ | $CH_3$ | Cl | (2-) Cl | $OC_2H_5$ | $CH_3$ | (IB) logP = 2.02[a] |
| 43 | $CH_2$ | O | $C_2H_5$ | $CH_3$ | Cl | (2-) Cl | $OCH_3$ | $CH_3$ | (IB) logP = 1.71[a] |
| 44 | $CH_2$ | O | $C_2H_5$ | $CH_3$ | Cl | (2-) Cl | Br | $CH_3$ | (IB) logP = 1.81[a] |
| 45 | $CH_2$ | O | $C_2H_5$ | $CH_3$ | Cl | (2-) Cl | $CH_3$ | $CH_3$ | (IB) logP = 1.40[a] |
| 46 | $CH_2$ | O | $t-C_4H_9$ | $CH_3$ | Cl | (2-) Cl | $SCH_3$ | $CH_3$ | (IB) logP = 3.30[a] |
| 47 | $CH_2$ | O | $t-C_4H_9$ | $CH_3$ | Cl | (2-) Cl | $OC_2H_5$ | $CH_3$ | (IB) logP = 3.44[a] |
| 48 | $CH_2$ | O | $t-C_4H_9$ | $CH_3$ | Cl | (2-) Cl | $OCH_3$ | $CH_3$ | (IB) logP = 3.02[a] |
| 49 | $CH_2$ | O | $t-C_4H_9$ | $CH_3$ | Cl | (2-) Cl | Br | $CH_3$ | (IB) logP = 3.19[a] |
| 50 | $CH_2$ | O | $t-C_4H_9$ | $CH_3$ | Cl | (2-) Cl | $CH_3$ | $CH_3$ | (IB) logP = 2.53[a] |
| 51 | $CH_2$ | O | $CH_3$ | $CH_3$ | Cl | (2-) Cl | $SCH_3$ | $CH_3$ | (IB) logP = 1.66[a] |
| 52 | $CH_2$ | O | $CH_3$ | $CH_3$ | Cl | (2-) Cl | $OC_2H_5$ | $CH_3$ | (IB) logP = 1.76[a] |
| 53 | $CH_2$ | O | $CH_3$ | $CH_3$ | Cl | (2-) Cl | $OCH_3$ | $CH_3$ | (IB) logP = 1.48[a] |
| 54 | $CH_2$ | O | $CH_3$ | $CH_3$ | Cl | (2-) Cl | $CH_3$ | $CH_3$ | (IB) logP = 1.20[a] |
| 55 | $CH_2$ | O | $CH_3$ | H | Cl | (2-) Cl | $SCH_3$ | $CH_3$ | (IB) logP = 1.67[a] |
| 56 | $CH_2$ | O | $CH_3$ | H | Cl | (2-) Cl | $OC_2H_5$ | $CH_3$ | (IB) logP = 1.77[a] |
| 57 | $CH_2$ | O | $CH_3$ | H | Cl | (2-) Cl | $OCH_3$ | $CH_3$ | (IB) logP = 1.48[a] |
| 58 | $CH_2$ | O | $CH_3$ | H | Cl | (2-) Cl | $CH_3$ | $CH_3$ | (IB) logP = 1.19[a] |
| 59 | $CH_2$ | O | $C_2H_5$ | H | $OCH_3$ | (2-) $NO_2$ | $OC_2H_5$ | $CH_3$ | (IC) logP = 1.99[a] |
| 60 | $CH_2$ | O | $C_2H_5$ | H | $OCH_3$ | (2-) $NO_2$ | $SCH_3$ | $CH_3$ | (IC) logP = 1.92[a] |
| 61 | $CH_2$ | O | $C_2H_5$ | H | $CF_3$ | — | $SCH_3$ | $CH_3$ | (IA-Na salt) |
| 62 | $CH_2$ | O | $C_2H_5$ | H | Cl | (2-) F | $SCH_3$ | $CH_3$ | (IB) logP = 1.99[a] |
| 63 | $CH_2$ | O | $C_2H_5$ | H | $CF_3$ | — | H | $CH_3$ | (IA) |
| 64 | $CH_2$ | O | $C_2H_5$ | H | $CF_3$ | — | $CH_3$ | $CH_3$ | (IA) logP = 1.80[a] |
| 65 | $CH_2$ | O | $C_2H_5$ | H | $CF_3$ | — | $CH_2OCH_3$ | $CH_3$ | (IA) logP = 1.98[a] |
| 66 | $CH_2$ | O | $C_2H_5$ | H | $CF_3$ | — | $OCH_3$ | $CH_3$ | (IA) logP = 2.27[a] |
| 67 | $CH_2$ | O | $C_2H_5$ | H | $SO_2CH_3$ | — | $CF_3$ | $CH_3$ | (IA) logP = 1.60[a] |
| 68 | $CH_2$ | O | $C_2H_5$ | H | $SO_2CH_3$ | — | $OCH_2CF_3$ | $CH_3$ | (IA) logP = 1.73[a] |
| 69 | $CH_2$ | O | $C_2H_5$ | H | F | (2-) Cl | $CH_3$ | $CH_3$ | (IB) logP = 1.27[a] |
| 70 | $CH_2$ | O | $C_2H_5$ | H | F | (2-) Cl | $SCH_3$ | $CH_3$ | (IB) logP = 1.76[a] |
| 71 | $CH_2$ | O | $C_2H_5$ | H | F | (2-) Cl | $OCH_3$ | $CH_3$ | (IB) logP = 1.55[a] |
| 72 | $CH_2$ | O | $C_2H_5$ | H | F | (2-) Cl | $N(CH_3)_2$ | $CH_3$ | (IB) logP = 1.62[a] |
| 73 | $CH_2$ | O | $C_2H_5$ | H | $SO_2CH_3$ | (2-) Cl | $SCH_3$ | $CH_3$ | (IB) m.p.: 204° C. |
| 74 | $CH_2$ | O | $C_2H_5$ | H | $SO_2CH_3$ | (2-) Cl | $OCH_3$ | $CH_3$ | (IB) m.p.: 183° C. |
| 75 | $CH_2$ | O | $C_2H_5$ | H | $SO_2CH_3$ | (2-) Cl | $OCH_2CF_3$ | $CH_3$ | (IB) m.p.: 192° C. |
| 76 | $CH_2$ | O | $C_2H_5$ | H | $SO_2CH_3$ | (2-) Cl | $CH_3$ | $CH_3$ | (IB) m.p.: 200° C. |

TABLE 1-continued

Examples of the compounds of the formula (I), (IA), (IB),(IC)
Here, Y in each case represents hydrogen

| Ex. No. | A | Q | $R^1$ | $R^2$ | $R^3$ | (Position) $(R^4)_n$ | $R^5$ | $R^6$ | (Formula) Physical data |
|---|---|---|---|---|---|---|---|---|---|
| 77 | $CH_2$ | O | $C_2H_5$ | H | $SO_2CH_3$ | (2-) Cl | $OCH_3$ | △ | (IB) m.p.: 205° C. |
| 78 | $CH_2$ | O | $C_2H_5$ | H | $SO_2CH_3$ | (2-) Cl | $SCH_3$ | △ | (IB) m.p.: 233° C. |
| 79 | $CH_2$ | O | $C_2H_5$ | H | $SO_2CH_3$ | (2-) Cl | $CH_3$ | △ | (IB) m.p.: 223° C. |
| 80 | $CH_2$ | O | $C_2H_5$ | H | $SO_2CH_3$ | (2-) Cl | $C_2H_5$ | $OC_2H_5$ | (IB) m.p.: 163° C. |

Similarly to Example 1, and in accordance with the general description of the preparation process according to the invention, it is also possible to prepare, for example, the compounds of the general formula (I)—or of the formula (ID)—listed in Table 2 below.

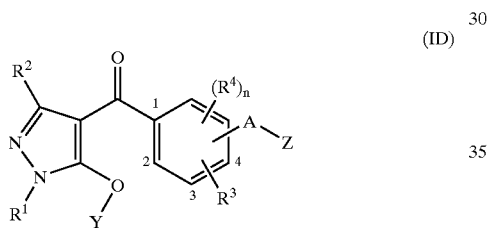

(ID)

TABLE 2

Further examples of the compounds of the formula (I)

| Ex. No. | $R^1$ | $R^2$ | (Position) $R^3$ | (Position) $(R^4)_n$ | (Position) -A-Z | Y | Physical data |
|---|---|---|---|---|---|---|---|
| ID-1 | $C_2H_5$ | H | (2-) Cl | (4-) Cl | (3-) 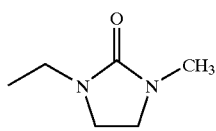 | H | logP = 1.64[a] |
| ID-2 | $C_2H_5$ | H | (2-) Cl | (4-) Cl | (3-) 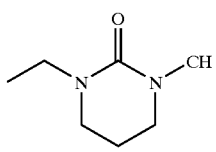 | H | logP = 1.77[a] |

TABLE 2-continued

Further examples of the compounds of the formula (I)

| Ex. No. | R¹ | R² | (Position) R³ | (Position) (R⁴)ₙ | (Position) -A–Z | Y | Physical data |
|---|---|---|---|---|---|---|---|
| ID-3 | $CH_3$ | H | (2-) Cl | (4-) Cl | (3-) [tetrahydro-1-ethyl-2-oxopyrimidin-3-yl-CH] | H | logP = 1.52[a] |
| ID-4 | $CH_3$ | $CH_3$ | (2-) Cl | (4-) Cl | (3-) [tetrahydro-1-ethyl-2-oxopyrimidin-3-yl-CH] | H | logP = 1.50[a] |
| ID-5 | $C_2H_5$ | $CH_3$ | (2-) Cl | (4-) Cl | (3-) [tetrahydro-1-ethyl-2-oxopyrimidin-3-yl-CH] | H | logP = 1.72[a] |
| ID-6 | $t\text{-}C_4H_9$ | $CH_3$ | (2-) Cl | (4-) Cl | (3-) [tetrahydro-1-ethyl-2-oxopyrimidin-3-yl-CH] | H | logP = 3.01[a] |
| ID-7 | $C_2H_5$ | H | (4-) $CF_3$ | — | (2-) [3-ethyl-2-oxo-5-(thiomethyl)-1,3,4-thiadiazol-3-yl] | H | logP = 2.98[a] |

TABLE 2-continued
Further examples of the compounds of the formula (I)
| Ex. No. | R¹ | R² | (Position) R³ | (Position) (R⁴)ₙ | (Position) -A–Z | Y | Physical data |
|---|---|---|---|---|---|---|---|
| ID-8 | $C_2H_5$ | H | (4-) $CF_3$ | — | (2-) 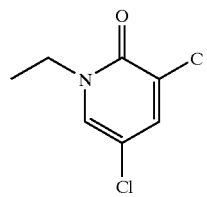 | H | logP = 2.75[a] |
| ID-9 | $C_2H_5$ | H | (4-) $CF_3$ | — | (2-) 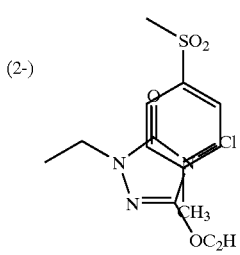 | | logP = 3.82[a] |
| ID-10 | $C_2H_5$ | H | (4-) $CF_3$ | — | (2-) 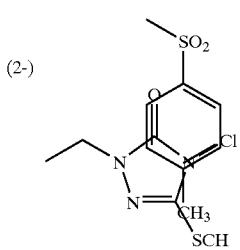 | | logP = 3.73[a] |
| ID-11 | $C_2H_5$ | H | (4-) $CF_3$ | — | (2-) 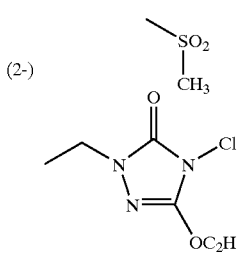 | | logP = 3.25[a] |
| ID-12 | $C_2H_5$ | H | (4-) $CF_3$ | — | (2-) 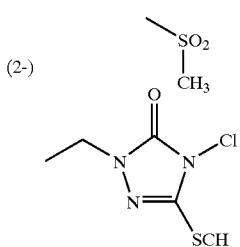 | | logP = 2.82[a] |

TABLE 2-continued
Further examples of the compounds of the formula (I)
| Ex. No. | R¹ | R² | (Position) R³ | (Position) (R⁴)ₙ | (Position) -A–Z | Y | Physical data |
|---|---|---|---|---|---|---|---|
| ID-13 | $C_2H_5$ | H | (4-) $CF_3$ | — | (2-) 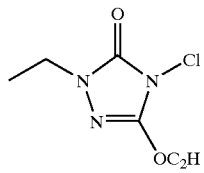 | $CH_3$ | logP = 2.74[a] |
| ID-14 | $C_2H_5$ | H | (4-) $CF_3$ | — | (2-) 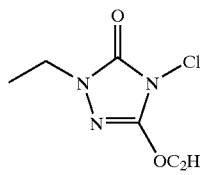 | $C_2H_5$ | logP = 2.82[a] |
| ID-15 | $C_2H_5$ | H | (4-) $CF_3$ | — | (2-) 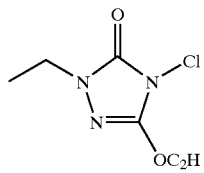 | $i-C_3H_7$ | logP = 3.11[a] |
| ID-16 | $C_2H_5$ | H | (4-) $CF_3$ | — | (2-) 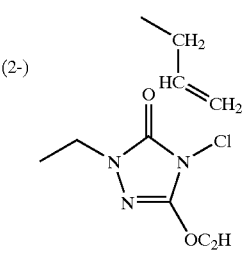 | | logP = 2.99[a] |
| ID-17 | $C_2H_5$ | H | (4-) $CF_3$ | — | (2-) 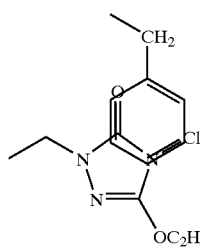 | | logP = 3.45[a] |

TABLE 2-continued

Further examples of the compounds of the formula (I)

| Ex. No. | R¹ | R² | (Position) R³ | (Position) (R⁴)ₙ | (Position) -A–Z | Y | Physical data |
|---|---|---|---|---|---|---|---|
| ID-18 | $C_2H_5$ | H | (4-) $CF_3$ | — | (2-) | 6-ethyl-4-chloro-1-ethyl-3-methyl-1H-indazol-7-yl-oxy (OC₂H) | logP = 3.79[a] |
| ID-19 | $C_2H_5$ | H | (4-) $CF_3$ | — | (2-) | 6-ethyl-4-chloro-1-ethyl-3-bromo-1H-indazol-7-yl-oxy (OC₂H) | logP = 3.97[a] |
| ID-20 | $C_2H_5$ | H | (4-) $CF_3$ | — | (2-) | 6-ethyl-4-chloro-1-ethyl-3-cyano-1H-indazol-7-yl-oxy (OC₂H) | logP = 3.12[a] |
| ID-21 | $C_2H_5$ | H | (4-) $CF_3$ | — | (2-) | 6-ethyl-4-chloro-1-ethyl-3-fluoro-1H-indazol-7-yl-oxy (OC₂H) | logP = 3.49[a] |
| ID-22 | $C_2H_5$ | H | (4-) $CF_3$ | — | (2-) | 6-ethyl-4-chloro-1-ethyl-3-chloro-1H-indazol-7-yl-oxy (OC₂H) | logP = 3.85[a] |

TABLE 2-continued
Further examples of the compounds of the formula (I)
| Ex. No. | R¹ | R² | (Position) R³ | (Position) (R⁴)ₙ | (Position) -A-Z | Y | Physical data |
|---|---|---|---|---|---|---|---|
| ID-23 | $C_2H_5$ | H | (4-) $CF_3$ | — | (2-) | 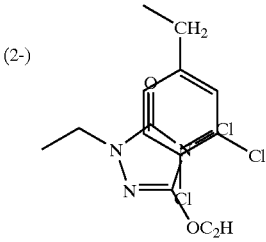 | logP = 4.26[a)] |
| ID-24 | $C_2H_5$ | H | (4-) $CF_3$ | — | (2-) | 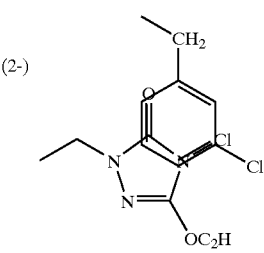 | logP = 3.84[a)] |
| ID-25 | $C_2H_5$ | H | (4-) $CF_3$ | — | (2-) | 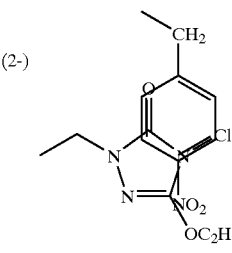 | logP = 3.33[a)] |
| ID-26 | $C_2H_5$ | H | (4-) $CF_3$ | — | (2-) | 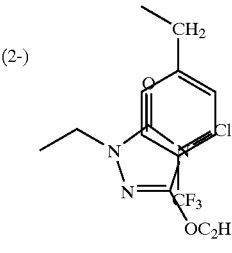 | logP = 3.98[a)] |
| ID-27 | $C_2H_5$ | H | (4-) $CF_3$ | — | (2-) | 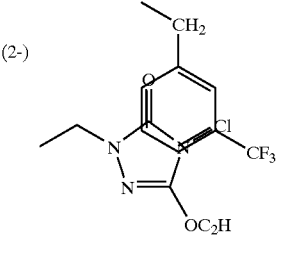 | logP = 3.94[a)] |

TABLE 2-continued
Further examples of the compounds of the formula (I)
| Ex. No. | R¹ | R² | (Position) R³ | (Position) (R⁴)ₙ | (Position) -A-Z | Y | Physical data |
|---|---|---|---|---|---|---|---|
| ID-28 | C₂H₅ | H | (4-) CF₃ | — | (2-) | 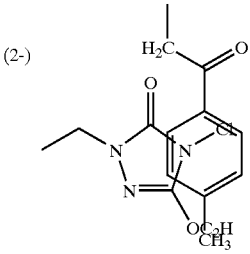 | logP = 3.57[a] |
| ID-29 | C₂H₅ | H | (4-) CF₃ | — | (2-) | 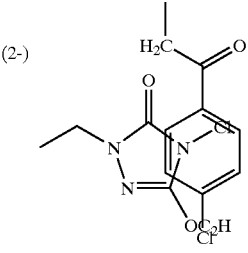 | logP = 3.75[a] |
| ID-30 | C₂H₅ | H | (4-) CF₃ | — | (2-) | CH₃ 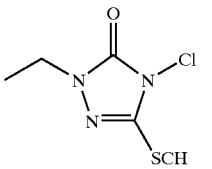 | logP = 2.65[a] |
| ID-31 | C₂H₅ | H | (4-) CF₃ | — | (2-) | C₂H₅ 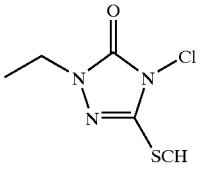 | logP = 2.71[a] |
| ID-32 | C₂H₅ | H | (4-) CF₃ | — | (2-) | i-C₃H₇ 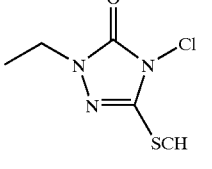 | logP = 3.00[a] |

TABLE 2-continued

Further examples of the compounds of the formula (I)

| Ex. No. | R¹ | R² | (Position) R³ | (Position) (R⁴)ₙ | (Position) -A-Z | Y | Physical data |
|---|---|---|---|---|---|---|---|
| ID-33 | $C_2H_5$ | H | (4-) $CF_3$ | — | (2-) | (triazolinone with ethyl, Cl, SCH, and OCH₂CH=CH₂ substituents) | logP = 2.89[a] |
| ID-34 | $C_2H_5$ | H | (4-) $CF_3$ | — | (2-) | (indazole with ethyl, Cl, SCH, OCH₂CH₃) | logP = 3.37[a] |
| ID-35 | $C_2H_5$ | H | (4-) $CF_3$ | — | (2-) | (indazole with ethyl, Cl, CH₃, SCH, OCH₂CH₃) | logP = 3.71[a] |
| ID-36 | $C_2H_5$ | H | (4-) $CF_3$ | — | (2-) | (indazole with ethyl, Cl, Br, SCH, OCH₂CH₃) | logP = 3.89[a] |
| ID-37 | $C_2H_5$ | H | (4-) $CF_3$ | — | (2-) | (indazole with ethyl, Cl, CN, SCH, OCH₂CH₃) | logP = 3.06[a] |

TABLE 2-continued

Further examples of the compounds of the formula (I)

| Ex. No. | $R^1$ | $R^2$ | (Position) $R^3$ | (Position) $(R^4)_n$ | (Position) -A–Z | Y | Physical data |
|---|---|---|---|---|---|---|---|
| ID-38 | $C_2H_5$ | H | (4-) $CF_3$ | — | (2-) | 1-ethyl-3-(methylthio)-4-fluoro-5-chloro-7-(oxymethyl)indazolyl | logP = 3.41[a] |
| ID-39 | $C_2H_5$ | H | (4-) $CF_3$ | — | (2-) | 1-ethyl-3-(methylthio)-4-chloro-5-chloro-7-(oxymethyl)indazolyl | logP = 3.78[a] |
| ID-40 | $C_2H_5$ | H | (4-) $CF_3$ | — | (2-) | 1-ethyl-3-(methylthio)-4-chloro-6-chloro-7-(oxymethyl)indazolyl | logP = 4.17[a] |
| ID-41 | $C_2H_5$ | H | (4-) $CF_3$ | — | (2-) | 1-ethyl-3-(methylthio)-5-chloro-6-chloro-7-(oxymethyl)indazolyl | logP = 3.76[a] |
| ID-42 | $C_2H_5$ | H | (4-) $CF_3$ | — | (2-) | 1-ethyl-3-(methylthio)-4-nitro-5-chloro-7-(oxymethyl)indazolyl | logP = 3.26[a] |

TABLE 2-continued

Further examples of the compounds of the formula (I)

| Ex. No. | R[1] | R[2] | (Position) R[3] | (Position) (R[4])$_n$ | (Position) -A-Z | Y | Physical data |
|---|---|---|---|---|---|---|---|
| ID-43 | $C_2H_5$ | H | (4-) $CF_3$ | — | (2-) | (structure) | logP = 3.89[a)] |
| ID-44 | $C_2H_5$ | H | (4-) $CF_3$ | — | (2-) | (structure) | logP = 3.85[a)] |
| ID-45 | $C_2H_5$ | H | (4-) $CF_3$ | — | (2-) | (structure) | logP = 3.19[a)] |
| ID-46 | $C_2H_5$ | H | (4-) $CF_3$ | — | (2-) | (structure) | logP = 3.47[a)] |
| ID-47 | $C_2H_5$ | H | (4-) CF | — | (2-) | (structure) | logP = 3.64[a)] |

TABLE 2-continued

Further examples of the compounds of the formula (I)

| Ex. No. | R¹ | R² | (Position) R³ | (Position) (R⁴)ₙ | (Position) -A–Z | Y | Physical data |
|---|---|---|---|---|---|---|---|
| ID-48 | $C_2H_5$ | H | (2-) $OCH_3$ | (4-) Cl | (3-) *1-ethyl-3-methylimidazolidin-2-one* | H | |
| ID-49 | $C_2H_5$ | H | (2-) $OCH_3$ | (4-) Cl | (3-) *1-ethyl-3-methylimidazolidin-2-one* | H | |
| ID-50 | $CH_3$ | H | (2-) Cl | (4-) Cl | (3-) *1-ethyl-3-methylimidazolidin-2-one* | H | logP = 1.41[a] |
| ID-51 | $CH_3$ | $CH_3$ | (2-) Cl | (4-) Cl | (3-) *1-ethyl-3-methylimidazolidin-2-one* | H | logP = 1.38[a] |
| ID-52 | $C_2H_5$ | $CH_3$ | (2-) Cl | (4-) Cl | (3-) *1-ethyl-3-methylimidazolidin-2-one* | H | logP = 1.56[a] |
| ID-53 | $t\text{-}C_4H_9$ | $CH_3$ | (2-) Cl | (4-) Cl | (3-) *1-ethyl-3-methylimidazolidin-2-one* | H | logP = 2.79[a] |

TABLE 2-continued

Further examples of the compounds of the formula (I)

| Ex. No. | R¹ | R² | (Position) R³ | (Position) (R⁴)ₙ | -A-Z | Y | Physical data |
|---|---|---|---|---|---|---|---|
| ID-54 | CH₃ | H | (2-) Cl | (4-) Cl | 1-ethyl-3-ethyl-imidazolidin-2-one-yl | H | logP = 1.62[a] |
| ID-55 | CH₃ | CH₃ | (2-) Cl | (4-) Cl | 1-ethyl-3-ethyl-imidazolidin-2-one-yl | H | logP = 1.57[a] |
| ID-56 | C₂H₅ | H | (2-) Cl | (4-) Cl | 1-ethyl-3-ethyl-imidazolidin-2-one-yl | H | logP = 1.88[a] |
| ID-57 | C₂H₅ | CH₃ | (2-) Cl | (4-) Cl | 1-ethyl-3-ethyl-imidazolidin-2-one-yl | H | logP = 1.79[a] |
| ID-58 | t-C₄H₉ | CH₃ | (2-) Cl | (4-) Cl | 1-ethyl-3-ethyl-imidazolidin-2-one-yl | H | logP = 3.15[a] |

The logP values given in Tables 1 and 2 were determined in accordance with EEC Directive 79/831 Annex V.A8 by HPLC (High Performance Liquid Chromatography) on a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—corresponding measurement results in Table 1 are marked [a]).

(b) Mobile phases for the determination in the neutral range: 0.01 molar aqueous phosphate buffer solution, acetonitrile; linear gradient from 10% acetonitrile to 90% acetonitrile—corresponding measurement results in Table 1 are marked [b]).

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

Starting Materials of Formula (III)

Example (III-1)

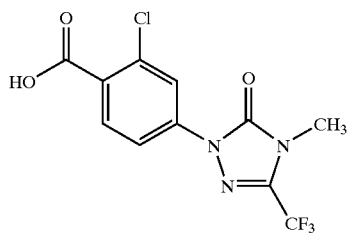

4.5 g (15 mmol) of 2-(3-chloro-4-cyano-phenyl)-4-methyl-5-trifluoromethyl-2,4-dihydro-3H-1,2,4-triazol-3-one are taken up in 80 ml of 60% strength sulfuric acid, and the mixture is heated at reflux for 6 hours. After cooling to room temperature, the resulting crystalline product is isolated by filtration with suction.

This gives 4.5 g (91% of theory) of 2-(3-carboxy-4-chloro-phenyl)-4-methyl-5-trifluoromethyl-2,4-dihydro-3H-1,2,4-triazol-3-one of melting point 223° C.

Example (III-2)

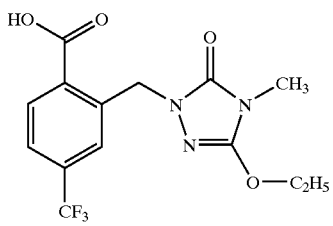

2 g (4.9 mmol) of 5-bromo-4-methyl-2-(2-ethoxycarbonyl-5-trifluoromethyl-benzyl)-2,4-dihydro-3H-1,2,4-triazol-3-one (cf. Example IV-1) are dissolved in 30 ml of 10% strength ethanolic potassium hydroxide solution and heated at reflux for 2 hours. The reaction mixture is concentrated under waterpump vacuum and the residue is taken up in 20 ml of water and acidified with dilute hydrochloric acid. The precipitated solid is filtered and dried.

This gives 1.2 g (71% of theory) of 5-ethoxy-4methyl-2-(2-carboxy-5-trifluormethyl-benzyl)-2,4-dihydro-3H-1,2,4-triazol-3-one as a solid product.

logP: 2.18$^{a)}$)

Example (III-3)

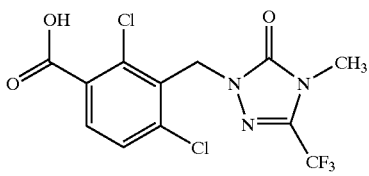

13.4 g (35 mmol) of 4-methyl-5-trifluoromethyl-2-(2,6-dichloro-3-methoxycarbonyl-benzyl)-2,4-dihydro-3H-1,2,4-triazol-3-one are initially charged in 60 ml of 1,4-dioxane, and a solution of 1.54 g (38.5 mmol) of sodium hydroxide in 20 ml of water is slowly metered in at room temperature. The reaction mixture is stirred at 60° C. for 150 minutes and then concentrated under waterpump vacuum. The residue is dissolved in 100 ml of water, and the pH of the solution is adjusted to 1 by addition of conc. hydrochloric acid. The resulting crystalline product is isolated by filtration with suction.

This gives 11.7 g (90% of theory) of 4-methyl-5-trifluoromethyl-2-(2,6-dichloro-3-carboxy-benzyl)-2,4-dihydro-3H-1,2,4-triazol-3-one of melting point 207° C.

Similarly to Examples (III-1) to (III-3), it is also possible to prepare, for example, the compounds of the general formula (III) listed in Table 3 below.

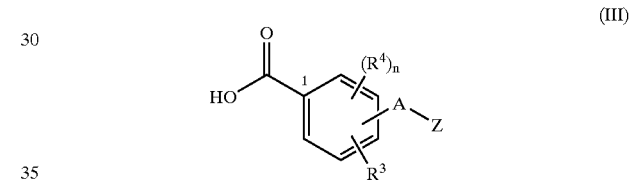

(III)

TABLE 32

Examples of the compounds of the formula (III)

| Ex. No. | (Position) R$^3$ | (Position) (R$^4$)$_n$ | (Position) —A—Z | Physical data |
|---------|------------------|------------------------|------------------|----------------|
| III-4 | (4-)Cl | — | (2-) ![structure] | logP = 1.39$^{a)}$ |
| III-5 | (4-)SO$_2$CH$_3$ | — | (3-) ![structure] | logP = 1.47$^{a)}$ |

TABLE 32-continued
Examples of the compounds of the formula (III)
| Ex. No. | (Position) R³ | (Position) (R⁴)ₙ | (Position) —A—Z | Physical data |
|---|---|---|---|---|
| III-6 | (4-)F | — | (2-) 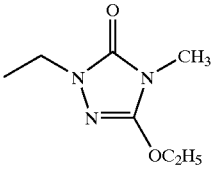 | logP = 1.73[a] |
| III-7 | (4-)CF₃ | — | (2-) 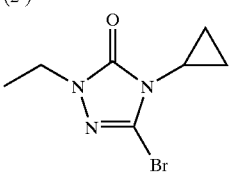 | logP = 1.65[a] |
| III-8 | (4-)Br | — | (2-) 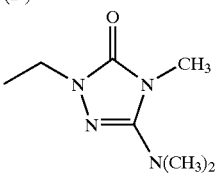 | logP = 1.74[a] |
| III-9 | (4-)CF₃ | — | (2-) 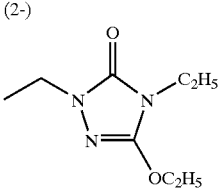 | logP = 2.43[a] |
| III-10 | (4-)CF₃ | — | (2-) 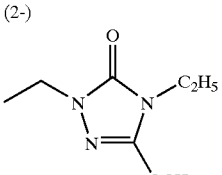 | logP = 2.12[a] |
| III-11 | (4-)CF₃ | — | (2-) 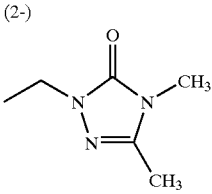 | logP = 1.61[a] |
| III-12 | (4-)CF₃ | — | (2-) 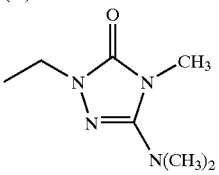 | logP = 1.93[a] |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-13 | (4-)CF₃ | — | (2-) 1-ethyl-4-methyl-5-bromo-1,2,4-triazol-3(4H)-one | logP = 2.01[a] |
| III-14 | (4-)CF₃ | — | (2-) N-ethylphthalimide | logP = 1.77[a] |
| III-15 | (3-)CH₃ | — | (2-) 1-ethyl-4-methyl-5-ethoxy-1,2,4-triazol-3(4H)-one | logP = 1.70[a] |
| III-16 | (4-)SO₂CH₃ | — | (2-) 1-ethyl-4-methyl-5-methylthio-1,2,4-triazol-3(4H)-one | logP = 1.07[a] |
| III-17 | (4-)CF₃ | — | (2-) 1-ethyl-4-methyl-5-ethylthio-1,2,4-triazol-3(4H)-one | logP = 2.35[a] |
| III-18 | (4-)CF₃ | — | (2-) 1-ethyl-4-methyl-5-(i-propylthio)-1,2,4-triazol-3(4H)-one | logP = 2.63[a] |
| III-19 | (4-)CF₃ | — | (2-) 1-ethyl-4-cyclopropyl-5-methoxy-1,2,4-triazol-3(4H)-one | logP = 2.13[a] |

TABLE 32-continued
Examples of the compounds of the formula (III)
| Ex. No. | (Position) R³ | (Position) (R⁴)ₙ | (Position) —A—Z | Physical data |
|---|---|---|---|---|
| III-20 | (4-)CF₃ | — | (2-) 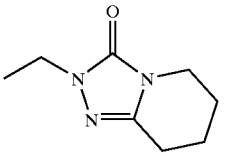 | logP = 1.82[a)] |
| III-21 | (4-)CF₃ | — | (2-) 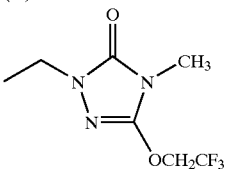 | logP = 2.48[a)] |
| III-22 | (4-)CF₃ | — | (2-) 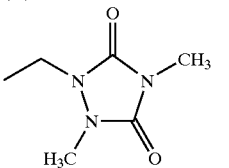 | logP = 1.73[a)] |
| III-23 | (4-)CF₃ | — | (2-) 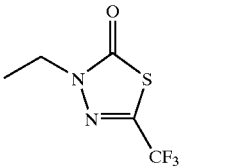 | logP = 3.11[a)] |
| III-24 | (4-)F | — | (2-) 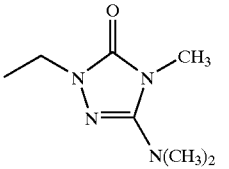 | logP = 1.43[a)] |
| III-25 | (4-)F | — | (2-) 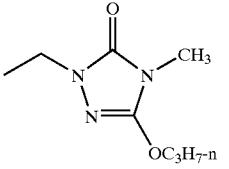 | logP = 1.97[a)] |
| III-26 | (4-)F | — | (2-) 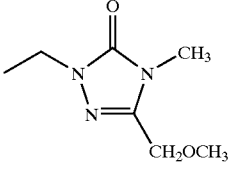 | logP = 1.30[a)] |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-27 | (4-)F | — | (2-) 1-ethyl-4-cyclopropyl-5-methoxy-1,2,4-triazol-3-one | logP = 1.63[a] |
| III-28 | (4-)F | — | (2-) 1-ethyl-4-cyclopropyl-5-ethoxy-1,2,4-triazol-3-one | logP = 1.93[a] |
| III-29 | (4-)CF₃ | — | (2-) 1-ethyl-4,4,5-trimethyl-pyrazol-3-one | logP = 1.78[a] |
| III-30 | (2-)Cl | (4-)Cl | (3-) 1-ethyl-4-methyl-5-methylthio-1,2,4-triazol-3-one | m.p.: 230° C. logP = 1.63[a] |
| III-31 | (2-)Cl | (4-)Cl | (3-) 1-ethyl-4-methyl-5-ethoxy-1,2,4-triazol-3-one | m.p.: 190° C. logP = 1.73[a] |
| III-32 | (2-)Cl | (4-)Cl | (3-) 1-ethyl-4-cyclopropyl-5-cyclopropyl-1,2,4-triazol-3-one | m.p.: 210° C. logP = 1.87[a] |
| III-33 | (2-)Cl | (4-)Cl | (3-) 1-ethyl-4-methyl-5-methoxy-1,2,4-triazol-3-one | m.p.: 210° C. logP = 1.43[a] |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-34 | (2-)Cl | (4-)Cl | (3-) 1-ethyl-4-methyl-5-(isopropoxy)-1H-1,2,4-triazol-3(4H)-one | m.p.: 164° C. logP = 2.01[a] |
| III-35 | (2-)Cl | (4-)Cl | (3-) 1-ethyl-4-methyl-5-(2,2,2-trifluoroethoxy)-1H-1,2,4-triazol-3(4H)-one | m.p.: 168° C. logP = 2.04[a] |
| III-36 | (2-)Cl | (4-)Cl | (3-) 5-bromo-1-ethyl-4-methyl-1H-1,2,4-triazol-3(4H)-one | m.p.: 218° C. logP = 1.53[a] |
| III-37 | (2-)Cl | (4-)Cl | (3-) 1-ethyl-4-methyl-1H-1,2,4-triazol-3(4H)-one | m.p.: 259° C. logP = 0.98[a] |
| III-38 | (2-)Cl | (4-)Cl | (3-) 5-cyclopropyl-1-ethyl-4-methyl-1H-1,2,4-triazol-3(4H)-one | m.p.: 210° C. logP = 1.56[a] |
| III-39 | (2-)Cl | (4-)Cl | (3-) 5-(dimethylamino)-1-ethyl-4-methyl-1H-1,2,4-triazol-3(4H)-one | m.p.: 197° C. logP = 1.51[a] |
| III-40 | (2-)Cl | (4-)Cl | (3-) 1-ethyl-4,5-dimethyl-1H-1,2,4-triazol-3(4H)-one | m.p.: 262° C. logP = 1.11[a] |

TABLE 32-continued
Examples of the compounds of the formula (III)
| Ex. No. | (Position) R³ | (Position) (R⁴)ₙ | (Position) —A—Z | Physical data |
|---|---|---|---|---|
| III-41 | (2-)Cl | (4-)Cl | (3-) 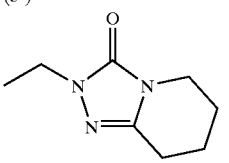 | m.p.: 249° C. logP = 1.30[a] |
| III-42 | (2-)Cl | (4-)Cl | (3-) 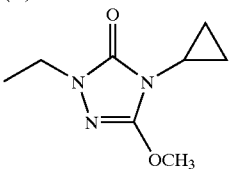 | m.p.: 200° C. logP = 1.71[a] |
| III-43 | (2-)Cl | (4-)Cl | (3-) 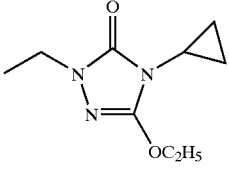 | m.p.: 189° C. logP = 2.01[a] |
| III-44 | (2-)Cl | (4-)Cl | (3-) 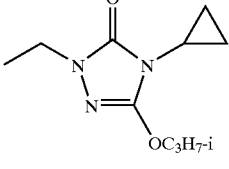 | m.p.: 178° C. logP = 2.28[a] |
| III-45 | (2-)Cl | (4-)Cl | (3-) 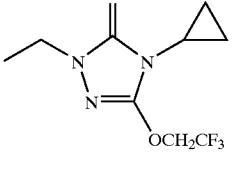 | m.p.: 161° C. logP = 2.31[a] |
| III-46 | (2-)Cl | (4-)Cl | (3-) 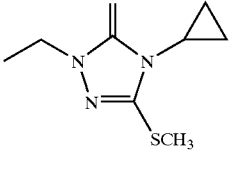 | m.p.: 200° C. logP = 1.98[a] |
| III-47 | (2-)Cl | (4-)Cl | (3-) 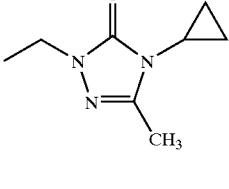 | m.p.: 201° C. logP = 1.39[a] |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-48 | (2-)Cl | (4-)Cl | (3-) [1-ethyl-4-cyclopropyl-5-(N(CH₃)₂)-1,2,4-triazol-3(4H)-one] | m.p.: 207° C. logP = 1.77[a] |
| III-49 | (2-)Cl | (4-)Cl | (3-) [1-ethyl-4-OC₂H₅-5-C₂H₅-1,2,4-triazol-3(4H)-one] | m.p.: 140° C. logP = 1.88[a] |
| III-50 | (4-)OCH₂CHF₂ | — | (2-) [1-ethyl-4-CH₃-5-CF₃-1,2,4-triazol-3(4H)-one] | m.p.: 154° C. logP = 2.14[a] |
| III-51 | — | — | (2-) [3-ethyl-1,2,3-benzotriazin-4(3H)-one] | m.p.: 214° C. logP = 1.87[a] |
| III-52 | — | — | (2-) [3-ethyl-benzoxazol-2(3H)-one] | m.p.: 194° C. logP = 2.07[a] |
| III-53 | — | — | (2-) [1-ethyl-3,5-dichloro-pyridin-2(1H)-one] | m.p.: 181° C. logP = 1.97[a] |
| III-54 | — | — | (2-) [1-ethyl-imidazolidine-2-thione] | m.p.: 251° C. logP = 1.14[a] |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-55 | (2-)Cl | (4-)Cl | (3-) | logP = 1.38[a] |
| III-56 | (2-)Cl | (4-)Cl | (3-) | logP = 1.48[a] |
| III-57 | (2-)Cl | (4-)Cl | (3-) | |
| III-58 | (4-)Cl | — | (2-) | ¹H-NMR (DMSO-D6, δ): 5.42 ppm. |
| III-59 | (4-)CF₃ | — | (2-) | ¹H-NMR (DMSO-D6, δ): 5.48 ppm. |
| III-60 | (4-)CF₃ | — | (2-) | ¹H-NMR (DMSO-D6, δ): 5.60 ppm. logP = 2.47[a] |
| III-61 | (4-)CF₃ | — | (2-) | logP = 2.33[a] |

TABLE 32-continued
Examples of the compounds of the formula (III)
| Ex. No. | (Position) R³ | (Position) (R⁴)ₙ | (Position) —A—Z | Physical data |
|---------|---------------|------------------|-----------------|---------------|
| III-62 | (4-)SO₂CH₃ | — | (3-) 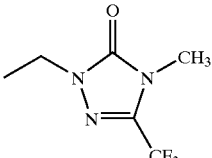 | ¹H-NMR (DMSO-D6, δ): 5.14 ppm. |
| III-63 | (4-)SO₂CH₃ | — | (2-) 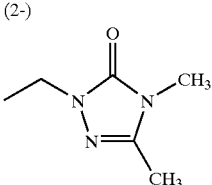 | ¹H-NMR (DMSO-D6, δ): 5.27 ppm. |
| III-64 | (4-)Cl | — | (3-) 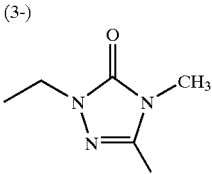 | ¹H-NMR (CDCl₃, δ): 5.12 ppm. |
| III-65 | (4-)Cl | — | (3-) 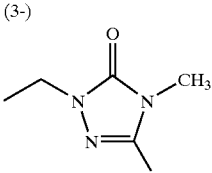 | ¹H-NMR (DMSO-D6, δ): 5.20 ppm. |
| III-66 | (4-)Cl | — | (2-) 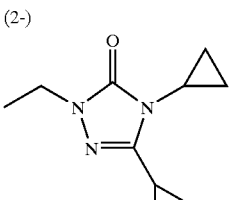 | ¹H-NMR (DMSO-D6, δ): 5.03 ppm. |
| III-67 | (4-)Br | — | (2-) 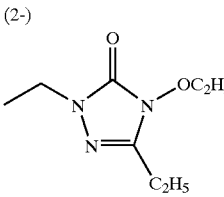 | ¹H-NMR (DMSO-D6, δ): 5.24 ppm. |
| III-68 | (4-)Br | — | (2-) 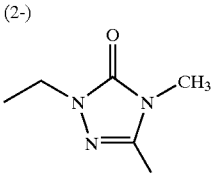 | ¹H-NMR (DMSO-D6, δ): 5.39 ppm. |

TABLE 32-continued
Examples of the compounds of the formula (III)
| Ex. No. | (Position) R³ | (Position) (R⁴)ₙ | (Position) —A—Z | Physical data |
|---|---|---|---|---|
| III-69 | (4-)F | — | (2-) 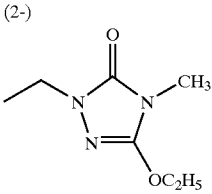 | ¹H-NMR (DMSO-D6, δ): 5.19 ppm. |
| III-70 | (4-)F | — | (2-) 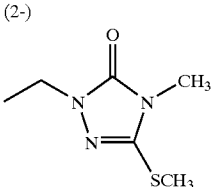 | ¹H-NMR (DMSO-D6, δ): 5.30 ppm. |
| III-71 | (4-)F | — | (2-) 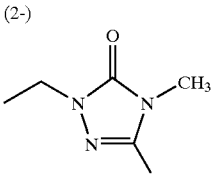 | ¹H-NMR (DMSO-D6, δ): 5.43 ppm. |
| III-72 | (4-)Br | — | (3-) 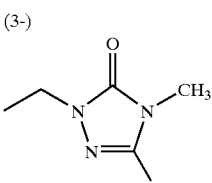 | ¹H-NMR, (CDCl₃ δ): 5.10 ppm. |
| III-73 | (4-)Br | — | (3-) 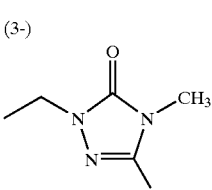 | ¹H-NMR (DMSO-D6, δ): 5.03 ppm. |
| III-74 | (4-)Br | — | (3-) 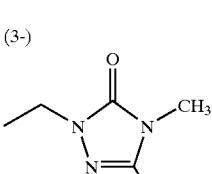 | ¹H-NMR (DMSO-D6, δ): 5.19 ppm. |
| III-75 | (4-)Br | — | (2-) 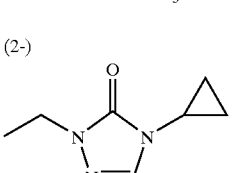 | ¹H-NMR (DMSO-D6, δ): 5.01 ppm. |

TABLE 32-continued
Examples of the compounds of the formula (III)
| Ex. No. | (Position) R³ | (Position) (R⁴)ₙ | (Position) —A—Z | Physical data |
|---|---|---|---|---|
| III-76 | (4-)Cl | — | (2-) 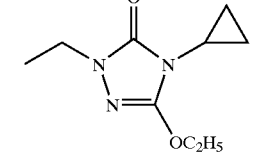 | ¹H-NMR (DMSO-D6, δ): 5.14 ppm. |
| III-77 | (4-)Cl | — | (2-) 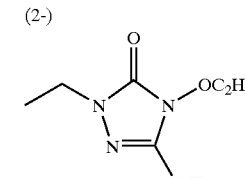 | ¹H-NMR (DMSO-D6, δ): 5.25 ppm. |
| III-78 | (4-)NO₂ | — | (2-) 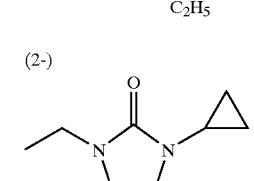 | ¹H-NMR (DMSO-D6, δ): 5.23 ppm. |
| III-79 | (4-)NO₂ | — | (2-) 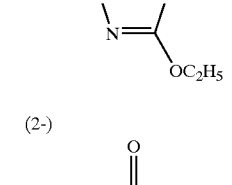 | ¹H-NMR (DMSO-D6, δ): 5.37 ppm. |
| III-80 | (4-)CF₃ | — | (2-) 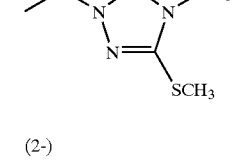 | logP = 2.46[a) |
| III-81 | (4-)CF₃ | — | (2-) 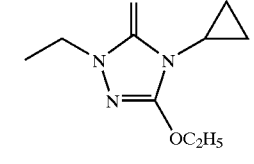 | ¹H-NMR (DMSO-D6, δ): 5.31 ppm. |
| III-82 | (4-)CF₃ | — | (2-) 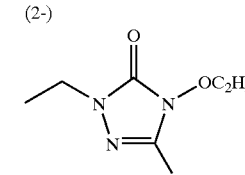 | logP = 2.08[a) |

TABLE 32-continued

Examples of the compounds of the formula (III)

| Ex. No. | (Position) R³ | (Position) (R⁴)ₙ | (Position) —A—Z | Physical data |
| --- | --- | --- | --- | --- |
| III-83 | (4-)OCH₃ | — | (2-) [1-ethyl-4-methyl-5-ethoxy-1,2,4-triazol-3(4H)-one] | ¹H-NMR (CDCl₃, δ): 5.38 ppm. |
| III-84 | (4-)OCH₃ | — | (2-) [1-ethyl-4-ethoxy-5-ethyl-1,2,4-triazol-3(4H)-one] | ¹H-NMR (CDCl₃, δ): 5.43 ppm. |
| III-85 | (4-)CF₃ | — | (2-) [1-ethyl-4-methyl-5-methoxymethyl-1,2,4-triazol-3(4H)-one] | ¹H-NMR (CDCl₃, δ): 5.47 ppm. |
| III-86 | (4-)Br | — | (2-) [2-ethyl-6,7-dihydro-5H-pyrrolo[2,1-c][1,2,4]triazol-3(2H)-one] | logP = 1.44[a)] |
| III-87 | (4-)Br | — | (2-) [2-ethyl-5,6,7,8-tetrahydro-[1,2,4]triazolo[4,3-a]pyridin-3(2H)-one] | logP = 1.63[a)] |
| III-88 | (4-)Br | — | (2-) [1-ethyl-4-methyl-5-isopropoxy-1,2,4-triazol-3(4H)-one] | logP = 2.27[a)] |
| III-89 | (4-)Br | — | (2-) [1-ethyl-4-methyl-5-n-propoxy-1,2,4-triazol-3(4H)-one] | logP = 2.31[a)] |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-90 | — | — | (2-) ethyl-4-methyl-5-CF₃-1,2,4-triazol-3(4H)-one | logP = 1.82[a] |
| III-91 | (4-)Br | — | (2-) ethyl-4-methyl-5-OC₂H₅-1,2,4-triazol-3(4H)-one | ¹H-NMR (CDCl₃, δ): 5.32 ppm. |
| III-92 | (4-)Br | — | (2-) ethyl-4-methyl-5-CF₃-1,2,4-triazol-3(4H)-one | ¹H-NMR (CDCl₃, δ): 5.53 ppm. |
| III-93 | (4-)F | — | (2-) ethyl-4-methyl-5-OC₂H₅-1,2,4-triazol-3(4H)-one | ¹H-NMR (CDCl₃, δ): 5.39 ppm. |
| III-94 | (4-)F | — | (2-) ethyl-4-methyl-5-CF₃-1,2,4-triazol-3(4H)-one | ¹H-NMR (CDCl₃, δ): 5.57 ppm. |
| III-95 | (4-)F | — | (2-) ethyl-4-OC₂H₅-5-C₂H₅-1,2,4-triazol-3(4H)-one | ¹H-NMR (CDCl₃, δ): 5.44 ppm. |
| III-96 | (4-)F | — | (2-) ethyl-4-methyl-5-OCH₃-1,2,4-triazol-3(4H)-one | ¹H-NMR (CDCl₃, δ): 5.41 ppm. |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-97 | — | — | (2-) [1,2,4-triazol-3(2H)-one, 2-ethyl-4-methyl-5-ethoxy] | ¹H-NMR (CDCl₃, δ): 5.34 ppm. |
| III-98 | — | — | (2-) [1,2,4-triazol-3(2H)-one, 2-ethyl-4-methyl-5-methoxy] | ¹H-NMR (CDCl₃, δ): 5.38 ppm. |
| III-99 | — | — | (2-) [1,2,4-triazol-3(2H)-one, 2-ethyl-4-cyclopropyl-5-cyclopropyl] | ¹H-NMR (CDCl₃, δ): 5.26 ppm. |
| III-100 | — | — | (2-) [1,2,4-triazol-3(2H)-one, 2-ethyl-4-methyl-5-methylthio] | ¹H-NMR (CDCl₃, δ): 5.43 ppm. |
| III-101 | — | — | (2-) [1,2,4-triazol-3(2H)-one, 2-ethyl-4-methyl-5-methylsulfonyl] | logP = 1.23[a)] |
| III-102 | (4-)SO₂CH₃ | — | (2-) [1,2,4-triazol-3(2H)-one, 2-ethyl-4-methyl-5-ethoxy] | logP = 1.14[a)] |
| III-103 | (4-)CF₃ | — | (2-) [1,2,4-triazol-3(2H)-one, 2-ethyl-4-methyl-5-isopropoxy] | logP = 2.45[a)] |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-104 | (4-)CF₃ | — | (2-) 1-ethyl-4-methyl-5-(n-propoxy)-1,2,4-triazol-3(4H)-one | logP = 2.48[a] |
| III-105 | (4-)Br | — | (2-) 5-bromo-1-ethyl-4-methyl-1,2,4-triazol-3(4H)-one | logP = 1.85[a] |
| III-106 | (4-)CF₃ | — | (3-) 1-ethyl-4-methyl-5-(i-propoxy)-1,2,4-triazol-3(4H)-one | logP = 2.74[a] |
| III-107 | (4-)CF₃ | — | (2-) 4-cyclopropyl-1-ethyl-5-(methoxymethyl)-1,2,4-triazol-3(4H)-one | logP = 2.01[a] |
| III-108 | (4-)CF₃ | — | (2-) 1-ethyl-4-methyl-5-(methoxymethyl)-1,2,4-triazol-3(4H)-one | logP = 1.79[a] |
| III-109 | (4-)CF₃ | — | (2-) 5-bromo-1-ethyl-4-methyl-1,2,4-triazol-3(4H)-one | logP = 1.65[a] |
| III-110 | (4-)Br | — | (2-) 1-ethyl-4-methyl-5-(methylthio)-1,2,4-triazol-3(4H)-one | logP = 1.90[a] |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-111 | (4-)Cl | — | (2-) 2-ethyl-4-methyl-5-(methylthio)-2,4-dihydro-3H-1,2,4-triazol-3-one | logP = 1.83[a] |
| III-112 | (4-)I | — | (2-) 2-ethyl-5-ethoxy-4-methyl-2,4-dihydro-3H-1,2,4-triazol-3-one | logP = 2.06[a] |
| III-113 | (4-)I | — | (2-) 2-ethyl-4-methyl-5-(trifluoromethyl)-2,4-dihydro-3H-1,2,4-triazol-3-one | m.p.: 104° C.<br>logP = 2.39[a] |
| III-114 | (4-)Br | — | (2-) 2-ethyl-2,3-dihydro-1H-phthalazin-1-one | m.p.: 191° C. |
| III-115 | (4-)Br | — | (2-) 3-ethyl-3,4-dihydro-1,2,3-benzotriazin-4-one | m.p.: 213° C. |
| III-116 | — | — | (2-) 2-ethylisoindoline-1,3-dione | |
| III-117 | — | — | (2-) 2-ethyl-4-methyl-5-(trifluoromethyl)-2,4-dihydro-3H-1,2,4-triazol-3-one | m.p.: 112° C. |

TABLE 32-continued

Examples of the compounds of the formula (III)

| Ex. No. | (Position) R³ | (Position) (R⁴)ₙ | (Position) —A—Z | Physical data |
|---------|---------------|------------------|-----------------|---------------|
| III-118 | (4-)CF₃ | — | (2-) [1-ethyl-4-methyl-5-trifluoromethyl-1,2,4-triazol-3(4H)-one] | m.p.: 158° C. |
| III-119 | (4-)CF₃ | — | (2-) [1-ethyl-4-cyclopropyl-5-cyclopropyl-1,2,4-triazol-3(4H)-one] | m.p.: 162° C. |
| III-120 | (4-)Cl | (5-)Cl | (2-) [1-ethyl-4-methyl-5-trifluoromethyl-1,2,4-triazol-3(4H)-one] | m.p.: 167° C. |
| III-121 | — | — | [1-ethyl-4-methyl-5-hydroxy-1,2,4-triazol-3(4H)-one] | m.p.: 188° C. |
| III-122 | — | — | (2-) [1-ethyl-4-cyclopropyl-5-cyclopropyl-1,2,4-triazol-3(4H)-one] | |
| III-123 | — | — | [1-ethyl-4-methyl-5-methyl-1,2,4-triazol-3(4H)-one] | m.p.: 131° C. |
| III-124 | (4-)Cl | — | (2-) [1-ethyl-4-methyl-5-trifluoromethyl-1,2,4-triazol-3(4H)-one] | m.p.: 109° C. |

TABLE 32-continued
Examples of the compounds of the formula (III)
| Ex. No. | (Position) R³ | (Position) (R⁴)ₙ | (Position) —A—Z | Physical data |
|---------|---------------|------------------|-----------------|---------------|
| III-125 | (4-)I | — | (2-) 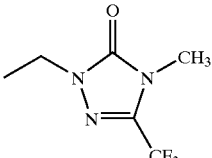 | m.p.: 104° C. |
| III-126 | (4-)Br | — | (2-) 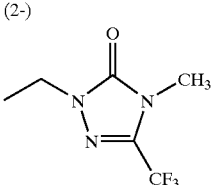 | m.p.: 99° C. |
| III-127 | (4-)Br | — | (2-) 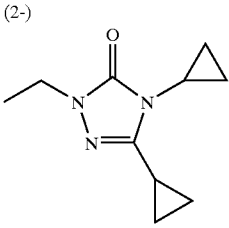 | m.p.: 174° C. |
| III-128 | — | — | (2-) 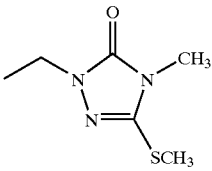 | m.p.: 122° C. |
| III-129 | (4-)Br | — | (2-) 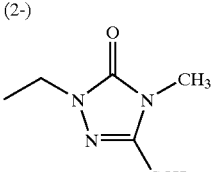 | m.p.: 164° C. |
| III-130 | — | — | (2-) 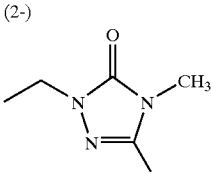 | m.p.: 154° C. |
| III-131 | (4-)Br | — | (2-) 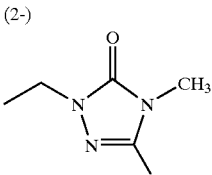 | m.p.: 161° C. |

TABLE 32-continued

Examples of the compounds of the formula (III)

| Ex. No. | (Position) R³ | (Position) (R⁴)ₙ | (Position) —A—Z | Physical data |
|---|---|---|---|---|
| III-132 | (4-)CN | — | (2-) 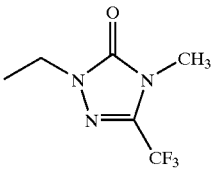 | m.p.: 196° C. |
| III-133 | — | — | (2-) 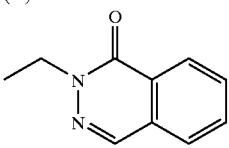 | m.p.: 192° C. |
| III-134 | — | — | 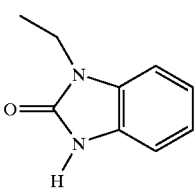 | |

The logP values given in Table 3 were determined in accordance with EEC Directive 79/831 Annex V.A8 by HPLC (High Performance Liquid Chromatography) on a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—corresponding measurement results in Table 1 are marked $^a$).

(b) Mobile phases for the determination in the neutral range: 0.01 molar aqueous phosphate buffer solution, acetonitrile; linear gradient from 10% acetonitrile to 90% acetonitrile—corresponding measurement results in Table 1 are marked $^b$).

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

Starting Materials of the Formula (IV)

Example (IV-1)

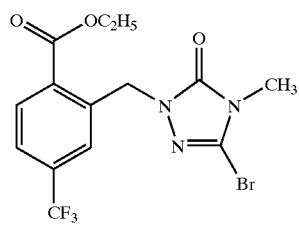

Step 1

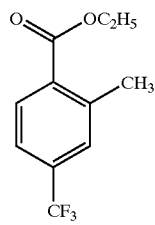

10 g (49 mmol) of 2-methyl-4-trifluoromethyl-benzoic acid are dissolved in 150 ml of ethanol and admixed with 1 ml of conc. sulfuric acid. The solution is heated at reflux for 24 hours and then concentrated, the residue is taken up in methylene chloride and the mixture is extracted with aqueous sodium bicarbonate solution. The methylene chloride phase is dried over sodium sulfate and concentrated under waterpump vacuum.

This gives 9 g (80% of theory) of ethyl 2-methyl-4-trifluoromethyl-benzoate as an amorphous residue.

Step 2

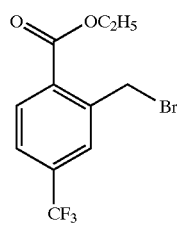

9 g (39 mmol) of ethyl 2-methyl-4-trifluoromethyl-benzoate are dissolved in 200 ml of carbon tetrachloride and admixed with 7 g (39 mmol) of N-bromo-succinimide and 0.1 g of dibenzoyl peroxide. The mixture is heated at reflux for 6 hours, and the precipitated succinimide is then filtered and the filtrate is concentrated under waterpump vacuum.

This gives 12 g of an amorphous residue which, in addition to ethyl 2-bromomethyl4-trifluoromethyl-benzoate, also contains 17% of ethyl 2,2-dibromomethyl-4-trifluoromethyl-benzoate and 12% of ethyl 2-methyl-4-trifluoromethyl-benzoate.

Step 3

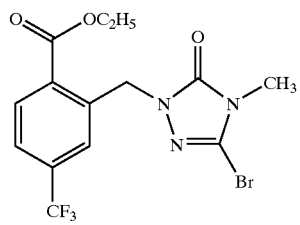

4 g of ethyl 2-bromomethyl-4-trifluoromethyl-benzoate (about 70% pure) and 2.28 g (12.8 mmol) of 5-bromo-4-methyl-2,4-dihydro-3H-1,2,4-triazol-3-one are dissolved in 150 ml of acetonitrile, admixed with 5.3 g (38.4 mmol) of potassium carbonate and, with vigorous stirring, heated at reflux for 2 hours. The reaction mixture is taken up in water and extracted repeatedly with methylene chloride. The combined methylene chloride phases are dried over sodium sulfate, concentrated under waterpump vacuum and chromatographed.

This gives 2 g (38% of theory) of 5-bromo4-methyl-2-(2-ethoxycarbonyl-5-trifluoromethyl-benzyl)-2,4-dihydro-3H-1,2,4-triazol-3-one as an amorphous product.

$^1$H-NMR (CDCl$_3$, δ): 5.46 ppm.

Example (IV-2)

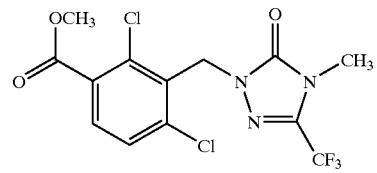

6.7 g (40 mmol) of 4-methyl-5-trifluoromethyl-2,4-dihydro-3H-1,2,4-triazol-3-one are initially charged in 150 ml of acetonitrile and stirred with 11 g (80 mmol) of potassium carbonate. The mixture is heated to 50° C., and a solution of 13.1 g (44 mmol) of methyl 3-bromomethyl-2,4-dichloro-benzoate in 20 ml of acetonitrile is then added dropwise with stirring, and the reaction mixture is heated at reflux with stirring for 15 hours. The mixture is then concentrated under waterpump vacuum and the residue is taken up in methylene chloride, washed with 1N hydrochloric acid, dried with sodium sulfate and filtered. The filtrate is concentrated under reduced pressure, the residue is digested with petroleum ether and the resulting crystalline product is isolated by filtration with suction.

This gives 14.9 g (97% of theory) of 4-methyl-5-trifluoromethyl-2-(2,6-dichloro-3-methoxycarbonyl-benzyl)-2,4-dihydro-3H-1,2,4-triazol-3-one of melting point 109° C.

Similarly to Examples (IV-1) and (IV-2), it is also possible to prepare, for example, the compounds of the general formula (IV) listed in Table 4 below.

(IV)

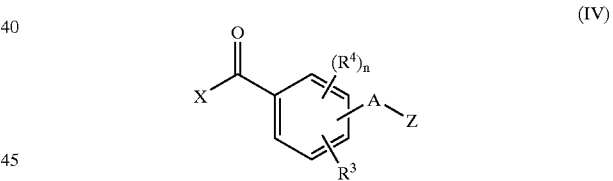

TABLE 4

| | Examples of the compounds of the formula (IV) | | | | |
|---|---|---|---|---|---|
| Ex. No. | (Position) R$^3$ | (Position) (R$^4$)$_n$ | (Position) —A—Z | X | Physical data |
| IV-3 | (2-)Cl | (4-)Cl | (3-) 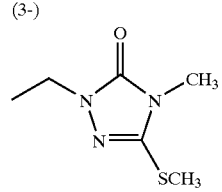 | OCH$_3$ | m.p.: 229° C. logP = 2.27[a)] |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-4 | (2-)Cl | (4-)Cl | (3-) 1-ethyl-4-methyl-5-ethoxy-1,2,4-triazol-3(2H)-one | OCH₃ | m.p.: 120° C. logP = 2.38[a] |
| IV-5 | (2-)Cl | (4-)Cl | (3-) 1-ethyl-4-cyclopropyl-5-cyclopropyl-1,2,4-triazol-3(2H)-one | OCH₃ | m.p.: 127° C. logP = 2.55[a] |
| IV-6 | (2-)Cl | (4-)Cl | (3-) 1-ethyl-4-methyl-5-methoxy-1,2,4-triazol-3(2H)-one | OCH₃ | m.p.: 121° C. logP = 2.04[a] |
| IV-7 | (2-)Cl | (4-)Cl | (3-) 1-ethyl-4-methyl-5-isopropoxy-1,2,4-triazol-3(2H)-one | OCH₃ | m.p.: 68° C. logP = 2.73[a] |
| IV-8 | (2-)Cl | (4-)Cl | (3-) 1-ethyl-4-methyl-5-(2,2,2-trifluoroethoxy)-1,2,4-triazol-3(2H)-one | OCH₃ | m.p.: 129° C. logP = 2.72[a] |
| IV-9 | (2-)Cl | (4-)Cl | (3-) 1-ethyl-4-methyl-5-bromo-1,2,4-triazol-3(2H)-one | OCH₃ | m.p.: 164° C. logP = 2.18[a] |
| IV-10 | (2-)Cl | (4-)Cl | (3-) 1-ethyl-4-methyl-1,2,4-triazol-3(2H)-one | OCH₃ | m.p.: 158° C. logP = 1.55[a] |

TABLE 4-continued
Examples of the compounds of the formula (IV)
| Ex. No. | (Position) R³ | (Position) (R⁴)ₙ | (Position) —A—Z | | X | Physical data |
|---|---|---|---|---|---|---|
| IV-11 | (2-)Cl | (4-)Cl | (3-) | 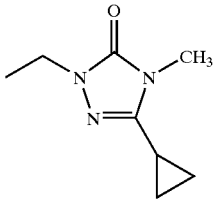 | OCH₃ | m.p.: 106° C.<br>logP = 2.16[a)] |
| IV-12 | (2-)Cl | (4-)Cl | (3-) | 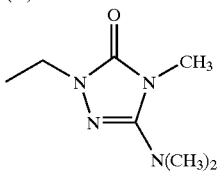 | OCH₃ | m.p.: 126° C.<br>logP = 2.11[a)] |
| IV-13 | (2-)Cl | (4-)Cl | (3-) | 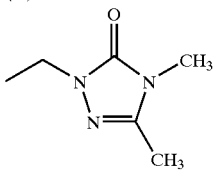 | OCH₃ | m.p.: 146° C.<br>logP = 1.65[a)] |
| IV-14 | (2-)Cl | (4-)Cl | (3-) | 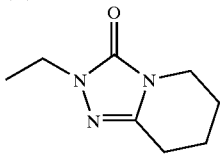 | OCH₃ | m.p.: 178° C.<br>logP = 1.86[a)] |
| IV-15 | (2-)Cl | (4-)Cl | (3-) | 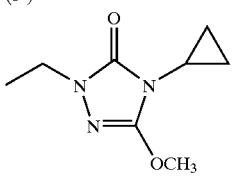 | OCH₃ | m.p.: 97° C.<br>logP = 2.36[a)] |
| IV-16 | (2-)Cl | (4-)Cl | (3-) | 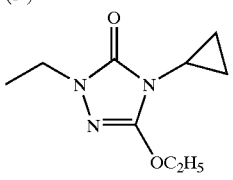 | OCH₃ | m.p.: 99° C.<br>logP = 2.73[a)] |
| IV-17 | (2-)Cl | (4-)Cl | (3-) | 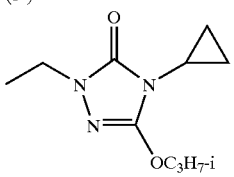 | OCH₃ | m.p.: 56° C.<br>logP = 3.08[a)] |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-18 | (2-)Cl | (4-)Cl | (3-) [1-ethyl-4-cyclopropyl-5-(OCH₂CF₃)-1,2,4-triazol-3(4H)-one] | OCH₃ | m.p.: 102° C. logP = 3.05[a] |
| IV-19 | (2-)Cl | (4-)Cl | (3-) [1-ethyl-4-cyclopropyl-5-(SCH₃)-1,2,4-triazol-3(4H)-one] | OCH₃ | m.p.: 131° C. logP = 2.70[a] |
| IV-20 | (2-)Cl | (4-)Cl | (3-) [1-ethyl-4-cyclopropyl-5-CH₃-1,2,4-triazol-3(4H)-one] | OCH₃ | m.p.: 135° C. logP = 1.97[a] |
| IV-21 | (2-)Cl | (4-)Cl | (3-) [1-ethyl-4-cyclopropyl-5-N(CH₃)₂-1,2,4-triazol-3(4H)-one] | OCH₃ | m.p.: 143° C. logP = 2.42[a] |
| IV-22 | (2-)Cl | (4-)Cl | (3-) [1-ethyl-4-OC₂H₅-5-C₂H₅-1,2,4-triazol-3(4H)-one] | OCH₃ | m.p.: 85° C. logP = 2.58[a] |
| IV-23 | (2-)Cl | (4-)Cl | (3-) [1-ethyl-3-methyl-imidazolidin-2-one] | OCH₃ | logP = 1.98[a] |
| IV-24 | (2-)Cl | (4-)Cl | (3-) [1-ethyl-3-methyl-tetrahydropyrimidin-2-one] | OCH₃ | logP = 2.07[a] |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-25 | (2-)Cl | (4-)Cl | (3-) ethyl-benzisothiazol-3(2H)-one 1,1-dioxide | OCH₃ | m.p.: 157° C. logP = 2.94[a)] |
| IV-26 | (4-)CF₃ | — | (2-) 2-ethyl-4-methyl-5-(methylsulfonyl)-2,4-dihydro-3H-1,2,4-triazol-3-one | OC₂H₅ | $^1$H-NMR (CDCl₃, δ): 5.53 ppm. |
| IV-27 | (4-)NO₂ | — | (3-) 2-ethyl-4-methyl-5-(trifluoromethyl)-2,4-dihydro-3H-1,2,4-triazol-3-one | OC₂H₅ | $^1$H-NMR (CDCl₃, δ): 5.48 ppm. |
| IV-28 | (4-)NO₂ | — | (3-) 2-ethyl-4-cyclopropyl-5-cyclopropyl-2,4-dihydro-3H-1,2,4-triazol-3-one | OC₂H₅ | $^1$H-NMR (CDCl₃, δ): 5.30 ppm. |
| IV-29 | (4-)SO₂CH₃ | — | (3-) 2-ethyl-4-methyl-5-(trifluoromethyl)-2,4-dihydro-3H-1,2,4-triazol-3-one | OC₂H₅ | $^1$H-NMR (CDCl₃, δ): 5.61 ppm. |
| IV-30 | (4-)Cl | — | (3-) 2-ethyl-4,5-dimethyl-2,4-dihydro-3H-1,2,4-triazol-3-one | OC₂H₅ | $^1$H-NMR (CDCl₃, δ): 5.08 ppm. |
| IV-31 | (4-)Cl | — | (3-) 2-ethyl-4-methyl-5-(trifluoromethyl)-2,4-dihydro-3H-1,2,4-triazol-3-one | OC₂H₅ | $^1$H-NMR (CDCl₃, δ): 5.17 ppm. |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-32 | (4-)Cl | — | (3-) [structure: 1-ethyl-4-cyclopropyl-5-cyclopropyl-1,2,4-triazol-3(4H)-one] | OC₂H₅ | ¹H-NMR (CDCl₃, δ): 5.00 ppm |
| IV-33 | (4-)SO₂CH₃ | — | (2-) [structure: 1-ethyl-pyrrolidine-2,5-dione] | OC₂H₅ | logP = 1.53ᵃ⁾ |
| IV-34 | (4-)Br | — | (2-) [structure: 1-ethyl-4-ethoxy-5-ethyl-1,2,4-triazol-3(4H)-one] | OC₂H₅ | logP = 3.24ᵃ⁾ |
| IV-35 | (4-)Br | — | (2-) [structure: 1-ethyl-4-methyl-5-trifluoromethyl-1,2,4-triazol-3(4H)-one] | OC₂H₅ | logP = 3.40ᵃ⁾ |
| IV-36 | (4-)F | — | (3-) [structure: 1-ethyl-4-methyl-5-bromo-1,2,4-triazol-3(4H)-one] | OC₂H₅ | logP = 2.41ᵃ⁾ |
| IV-37 | (4-)F | — | (2-) [structure: 1-ethyl-4-methyl-5-methylthio-1,2,4-triazol-3(4H)-one] | OC₂H₅ | logP = 2.45ᵃ⁾ |
| IV-38 | (4-)Br | — | (3-) [structure: 1-ethyl-4-methyl-5-methyl-1,2,4-triazol-3(4H)-one] | OC₂H₅ | logP = 2.06ᵃ⁾ |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-39 | (4-)Br | — | (3-) ethyl-methyl-Br-triazolinone | OC₂H₅ | logP = 2.64[a] |
| IV-40 | (4-)Br | — | (3-) ethyl-methyl-CF₃-triazolinone | OC₂H₅ | logP = 3.23[a] |
| IV-41 | (4-)Br | — | (3-) ethyl-cyclopropyl-cyclopropyl-triazolinone | OC₂H₅ | logP = 3.02[a] |
| IV-42 | (4-)Cl | — | (2-) ethyl-cyclopropyl-OC₂H₅-triazolinone | OC₂H₅ | logP = 3.23[a] |
| IV-43 | (4-)Cl | — | (2-) ethyl-methyl-CF₃-triazolinone | OC₂H₅ | logP = 3.31[a] |
| IV-44 | (4-)Cl | — | (2-) ethyl-OC₂H₅-C₂H₅-triazolinone | OC₂H₅ | logP = 3.14[a] |
| IV-45 | (4-)NO₂ | — | (2-) ethyl-cyclopropyl-OC₂H₅-triazolinone | OC₂H₅ | logP = 2.42[a] |

TABLE 4-continued
Examples of the compounds of the formula (IV)
| Ex. No. | (Position) R³ | (Position) (R⁴)ₙ | (Position) —A—Z | | X | Physical data |
|---|---|---|---|---|---|---|
| IV-46 | (4-)NO₂ | — | (2-) | 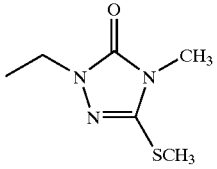 | OC₂H₅ | logP = 2.82[a)] |
| IV-47 | (4-)CF₃ | — | (2-) | 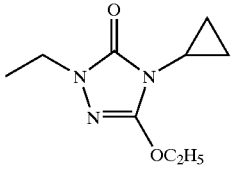 | OC₂H₅ | logP = 3.48[a)] |
| IV-48 | (4-)CF₃ | — | (2-) | 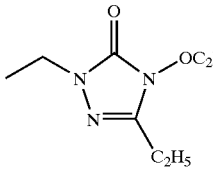 | OC₂H₅ | logP = 3.38[a)] |
| IV-49 | (4-)CF₃ | — | (2-) | 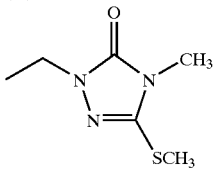 | OC₂H₅ | logP = 3.02[a)] |
| IV-50 | (4-)CF₃ | — | (2-) | 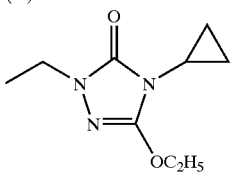 | OC₃H₇ | logP = 3.91[a)] |
| IV-51 | (4-)OCH₃ | — | (2-) | 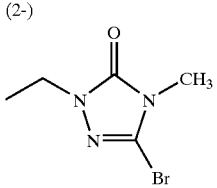 | OC₂H₅ | |
| IV-52 | (4-)OCH₃ | — | (2-) | 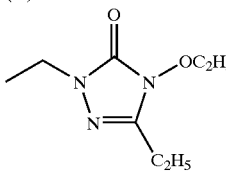 | OC₂H₅ | |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-53 | (4-)CF₃ | — | (2-) [1-ethyl-4-methyl-5-ethoxy-1,2,4-triazol-3(4H)-one] | OC₂H₅ | ¹H-NMR (CDCl₃, δ): 5.37 ppm. |
| IV-54 | (4-)CF₃ | — | (2-) [1-ethyl-4-methyl-5-methoxy-1,2,4-triazol-3(4H)-one] | OC₂H₅ | ¹H-NMR (CDCl₃, δ): 5.37 ppm. |
| IV-55 | — | — | (2-) [1-ethyl-4-methyl-5-ethoxy-1,2,4-triazol-3(4H)-one] | OC₂H₅ | |
| IV-56 | — | — | (2-) [1-ethyl-4-methyl-5-methoxy-1,2,4-triazol-3(4H)-one] | OC₂H₅ | ¹H-NMR (CDCl₃, δ): 5.37 ppm. |
| IV-57 | — | — | (2-) [1-ethyl-4-ethoxy-5-ethyl-1,2,4-triazol-3(4H)-one] | OC₂H₅ | ¹H-NMR (CDCl₃, δ): 5.40 ppm. |
| IV-58 | (4-)Br | — | (2-) [1-ethyl-4-methyl-5-ethoxy-1,2,4-triazol-3(4H)-one] | OC₂H₅ | logP = 2.95ᵃ⁾ |
| IV-59 | (4-)Br | — | (2-) [1-ethyl-4-methyl-5-methoxy-1,2,4-triazol-3(4H)-one] | OC₂H₅ | ¹H-NMR (CDCl₃, δ): 5.31 ppm. |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-60 | (4-)Br | — | (2-) ethyl-succinimide structure | OC₂H₅ | logP = 2.44[a] |
| IV-61 | (4-)F | — | (2-) 1-ethyl-4-methyl-5-ethoxy-1,2,4-triazol-3(4H)-one | OC₂H₅ | ¹H-NMR (CDCl₃, δ): 5.35 ppm. |
| IV-62 | (4-)F | — | (2-) 1-ethyl-4-methyl-5-trifluoromethyl-1,2,4-triazol-3(4H)-one | OC₂H₅ | ¹H-NMR (CDCl₃, δ): 5.53 ppm. |
| IV-63 | (4-)F | — | (2-) 1-ethyl-4-ethoxy-5-ethyl-1,2,4-triazol-3(4H)-one | OC₂H₅ | ¹H-NMR (CDCl₃, δ): 5.40 ppm. |
| IV-64 | (4-)F | — | (2-) 1-ethyl-4-methyl-5-methoxy-1,2,4-triazol-3(4H)-one | OC₂H₅ | ¹H-NMR (CDCl₃, δ): 5.36 ppm. |
| IV-65 | (4-)Br | — | (2-) 1-ethyl-4-methyl-5-isopropoxy-1,2,4-triazol-3(4H)-one | OC₂H₅ | logP = 3.34[a] |
| IV-66 | (4-)Br | — | (2-) 1-ethyl-4-methyl-5-n-propoxy-1,2,4-triazol-3(4H)-one | OC₂H₅ | logP = 3.38[a] |

TABLE 4-continued
Examples of the compounds of the formula (IV)
| Ex. No. | (Position) R³ | (Position) (R⁴)ₙ | (Position) —A—Z | X | Physical data |
|---|---|---|---|---|---|
| IV-67 | (4-)Br | — | (2-) 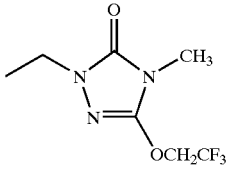 | OC₂H₅ | logP = 3.31[a)] |
| IV-68 | (4-)Br | — | (2-) 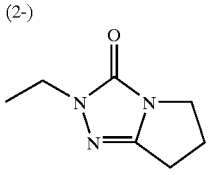 | OC₂H₅ | logP = 2.16[a)] |
| IV-69 | (4-)Br | — | (2-) 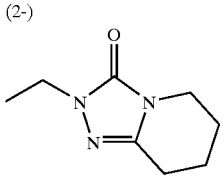 | OC₂H₅ | logP = 2.41[a)] |
| IV-70 | (4-)CF₃ | — | (2-) 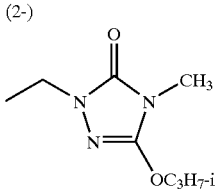 | OC₂H₅ | logP = 3.51[a)] |
| IV-71 | (4-)CF₃ | — | (2-) 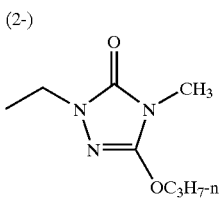 | OC₂H₅ | logP = 3.54[a)] |
| IV-72 | (4-)Br | — | (2-) 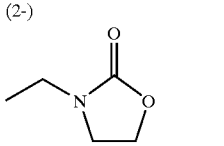 | OC₂H₅ | logP = 2.36[a)] |
| IV-73 | (4-)Br | — | (2-) 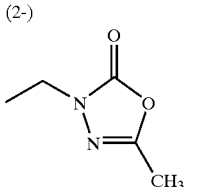 | OC₂H₅ | logP = 2.88[a)] |

TABLE 4-continued
Examples of the compounds of the formula (IV)
| Ex. No. | (Position) R³ | (Position) (R⁴)ₙ | (Position) —A—Z | | X | Physical data |
|---|---|---|---|---|---|---|
| IV-74 | (4-)CF₃ | — | (2-) | 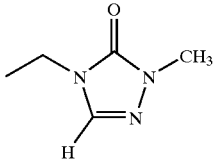 | OC₂H₅ | logP = 2.68[a)] |
| IV-75 | (4-)Br | — | (2-) | 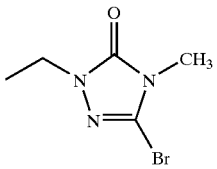 | OC₂H₅ | logP = 2.80[a)] |
| IV-76 | (4-)CF₃ | — | (3-) | 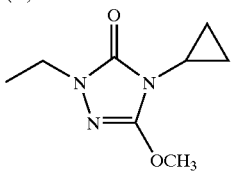 | OC₂H₅ | logP = 3.87[a)] |
| IV-77 | (4-)CF₃ | — | (2-) | 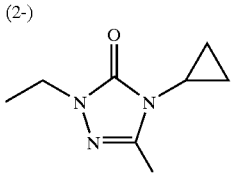 | OC₂H₅ | logP = 2.88[a)] |
| IV-78 | (4-)CF₃ | — | (2-) | 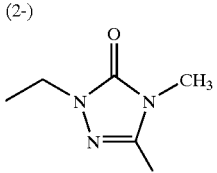 | OC₂H₅ | logP = 2.60[a)] |
| IV-79 | (4-)CF₃ | — | (2-) | 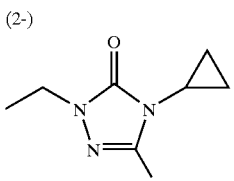 | OC₂H₅ | logP = 3.35[a)] |
| IV-80 | (4-)Br | — | (2-) | 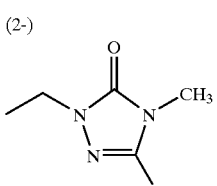 | OC₂H₅ | logP = 2.86[a)] |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-81 | (4-)Cl | — | (2-) ethyl-methyl-triazolone-SCH₃ | OC₂H₅ | logP = 2.83ᵃ⁾ |
| IV-82 | (4-)Br | — | (2-) ethyl-methyl-triazolone-N(CH₃)₂ | OC₂H₅ | logP = 2.60ᵃ⁾ |
| IV-83 | (4-)CF₃ | — | (2-) ethyl-ethyl-triazolone-OC₂H₅ | OC₂H₅ | ¹H-NMR (CDCl₃, δ): 5.36 ppm. |
| IV-84 | (4-)CF₃ | — | (2-) ethyl-ethyl-triazolone-OCH₃ | OC₂H₅ | ¹H-NMR (CDCl₃, δ): 5.37 ppm. |
| IV-85 | (4-)CF₃ | — | (2-) ethyl-methyl-triazolone-N(CH₃)₂ | OC₂H₅ | logP = 2.79ᵃ⁾ |
| IV-86 | (4-)CF₃ | — | (2-) saccharin-N-ethyl | OC₂H₅ | logP = 3.67ᵃ⁾ |
| IV-87 | (4-)CF₃ | — | (2-) phthalimide-N-ethyl | OC₂H₅ | logP = 3.80ᵃ⁾ |

TABLE 4-continued

Examples of the compounds of the formula (IV)

| Ex. No. | (Position) R³ | (Position) (R⁴)ₙ | (Position) —A—Z | X | Physical data |
|---------|---------------|------------------|-----------------|-----|---------------|
| IV-88 | (3-)CH₃ | — | (2-) [1-ethyl-4-methyl-5-ethoxy-1,2,4-triazol-3(4H)-one] | OC₂H₅ | logP = 2.54[a] |
| IV-89 | (4-)SO₂CH₃ | — | (2-) [1-ethyl-4-methyl-5-methylthio-1,2,4-triazol-3(4H)-one] | OC₂H₅ | logP = 1.82[a] |
| IV-90 | (4-)CF₃ | — | (2-) [1-ethyl-5-trifluoromethyluracil] | OC₂H₅ | logP = 2.93[a] |
| IV-91 | (4-)CF₃ | — | (2-) [1-ethyl-4-cyclopropyl-5-methoxy-1,2,4-triazol-3(4H)-one] | OC₂H₅ | logP = 3.08[a] |
| IV-92 | (4-)CF₃ | — | (2-) [3-ethyl-5-methyl-1,3,4-oxadiazol-2(3H)-one] | OC₂H₅ | logP = 3.04[a] |
| IV-93 | (4-)CF₃ | — | (2-) [1-ethyl-4-methyl-5-(2,2,2-trifluoroethoxy)-1,2,4-triazol-3(4H)-one] | OC₂H₅ | logP = 3.45[a] |
| IV-94 | (4-)F | — | (2-) [1-ethyl-4-methyl-5-dimethylamino-1,2,4-triazol-3(4H)-one] | OC₂H₅ | logP = 2.21[a] |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-95 | (4-)F | — | (2-) triazolinone with N-ethyl, N-methyl, OC₃H₇-n | OC₂H₅ | logP = 2.96[a] |
| IV-96 | (4-)F | — | (2-) triazolinone with N-ethyl, N-methyl, CH₂OCH₃ | OC₂H₅ | logP = 2.05[a] |
| IV-97 | (4-)F | — | (2-) triazolinone with N-ethyl, N-cyclopropyl, OCH₃ | OC₂H₅ | logP = 2.50[a] |
| IV-98 | (4-)F | — | (2-) triazolinone with N-ethyl, N-cyclopropyl, OC₂H₅ | OC₂H₅ | logP = 2.89[a] |
| IV-99 | (4-)CF₃ | — | (2-) pyrazolinone with N-ethyl, CH₃, CH₃, CH₃ | OC₂H₅ | logP = 2.91[a] |
| IV-100 | (4-)Cl | — | (2-) triazolinone with N-ethyl, N-methyl, CH₃ | OC₂H₅ | ¹H-NMR (CDCl₃, δ): 5.39 ppm. |
| IV-101 | (4-)Cl | — | (2-) triazolinone with N-ethyl, N-methyl, CF₃ | OC₂H₅ | ¹H-NMR (CDCl₃, δ): 5.50 ppm. |

TABLE 4-continued
Examples of the compounds of the formula (IV)
| Ex. No. | (Position) R³ | (Position) (R⁴)ₙ | (Position) —A—Z | | X | Physical data |
|---|---|---|---|---|---|---|
| IV-102 | (4-)Cl | — | (2-) | 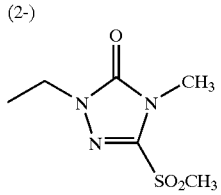 | OC₂H₅ | ¹H-NMR (CDCl₃, δ): 5.49 ppm. |
| IV-103 | (4-)CF₃ | — | (2-) | 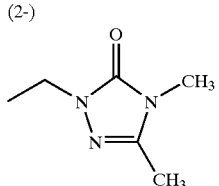 | OC₂H₅ | ¹H-NMR (CDCl₃, δ): 5.29 ppm. |
| IV-104 | (4-)CF₃ | — | (2-) | 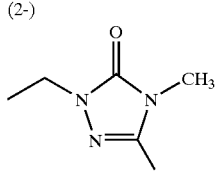 | OC₂H₅ | ¹H-NMR (CDCl₃, δ): 5.53 ppm. |
| IV-105 | (4-)CF₃ | — | (2-) | 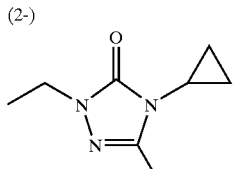 | OC₂H₅ | ¹H-NMR (CDCl₃, δ): 5.34 ppm. |
| IV-106 | (4-)SO₂CH₃ | — | (2-) | 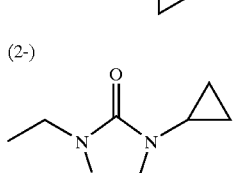 | OC₂H₅ | ¹H-NMR (CDCl₃, δ): 5.39 ppm. |
| IV-107 | (4-)SO₂CH₃ | — | (2-) | 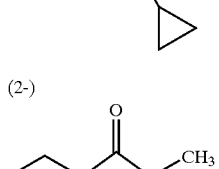 | OC₂H₅ | ¹H-NMR (CDCl₃, δ): 5.43 ppm. |
| IV-108 | (4-)SO₂CH₃ | — | (2-) | 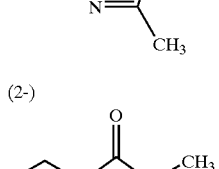 | OC₂H₅ | ¹H-NMR (CDCl₃, δ): 5.40 ppm. |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-109 | (4-)SO₂CH₃ | — | (2-) ethyl-CH₃-OC₂H₅ triazolone | OC₂H₅ | ¹H-NMR (CDCl₃, δ): 5.38 ppm. |
| IV-110 | (4-)Br | — | (2-) ethyl-CH₃-CF₃ triazolone | OC₂H₅ | ¹H-NMR (CDCl₃, δ): 5.49 ppm. |
| IV-111 | — | — | (2-) ethyl-cyclopropyl-cyclopropyl triazolone | OC₂H₅ | ¹H-NMR (CDCl₃, δ): 5.3 ppm. |
| IV-112 | — | — | (2-) ethyl-CH₃-SCH₃ triazolone | OC₂H₅ | ¹H-NMR (CDCl₃, δ): 5.44 ppm. |
| IV-113 | (4-)CF₃ | — | (2-) ethyl-CH₃-H₃C triazolidinedione | OC₂H₅ | logP = 2.58[a)] |
| IV-114 | (4-)SO₂CH₃ | — | (2-) ethyl-CH₃-SCH₃ triazolone | OCH₃ | logP = 1.53[a)] |
| IV-115 | (4-)SO₂CH₃ | — | (2-) ethyl-CH₃-OC₂H₅ triazolone | OCH₃ | logP = 1.59[a)] |

TABLE 4-continued

Examples of the compounds of the formula (IV)

| Ex. No. | (Position) R³ | (Position) (R⁴)ₙ | (Position) —A—Z | X | Physical data |
|---|---|---|---|---|---|
| IV-116 | (4-)I | — | (2-) [1-ethyl-4-methyl-5-ethoxy-1,2,4-triazol-3(4H)-one] | OCH₃ | logP = 2.68[a] |
| IV-117 | (4-)CF₃ | — | (2-) [1-ethyl-4-methyl-5-ethoxy-1,2,4-triazol-3(4H)-one] | OCH₃ | logP = 2.74[a] |
| IV-118 | (4-)CF₃ | — | (2-) [1-ethyl-4-methyl-5-methylthio-1,2,4-triazol-3(4H)-one] | OCH₃ | logP = 2.65[a] |
| IV-119 | (4-)CF₃ | — | (2-) [1-ethyl-4-methyl-5-bromo-1,2,4-triazol-3(4H)-one] | OC₂H₅ | logP = 2.96[a] |
| IV-120 | — | — | (2-) [1-ethyl-2-methyl-4-methyl-1,2,4-triazolidine-3,5-dione] | OCH₃ | m.p.: 106° C. |

The logP values given in Tables 4 were determined in accordance with EEC Directive 79/831 Annex V.A8 by HPLC (High Performance Liquid Chromatography) on a reversed-phase column (C 18). Temperature: 43° C.
(a) Mobile phases for the determination in the acidic range: 0.1% aqueous phosphoric acid, acetonitrile; linear gradient from 10% acetonitrile to 90% acetonitrile—corresponding measurement results in Table 1 are marked a)
(b) Mobile phases for the determination in the neutral range: 0.01 molar aqueous phosphate buffer solution, acetonitrile; linear gradient from 10% acetonitrile to 90% acetonitrile—corresponding measurement results in Table 1 are marked b).

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

USE EXAMPLES

Example A

Pre-emergence Test

| | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound is applied per unit area. The concentration of the spray liquor is chosen such that the particular amount of active compound desired is applied in 1000 liters of water per hectare.

After three weeks, the degree of damage to plants is rated in % damage in comparison to the development of the untreated control.

The figures denote:

0% = no effect (like untreated control)
100% = total destruction

In this test, for example, the compounds of Preparation Example 2 and 3 exhibit strong activity against weeds, and they are tolerated well by crop plants such as, for example, corn.

EXAMPLE B

Post-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0% = no effect (like untreated control)
100% = total destruction

In this test, for example, the compound of preparation example 2 and 3 exhibit strong activity against weeds.

What is claimed is:

1. A substituted benzoylpyrazole of the formula (I),

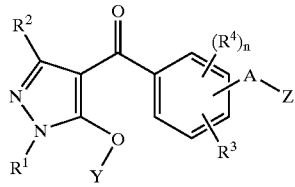

wherein n represents the numbers 0, 1 or 2,

A represents an alkanediyl having 1 to 4 carbon atoms, $R^1$ represents optionally cyano-, carboxyl-, carbamoyl-, halogen-, $C_1$–$C_4$-alkoxy-, $C_1$–$C_4$-alkyl-carbonyl-, $C_1$–$C_4$-alkoxy-carbonyl-, $C_1$–$C_4$-alkylthio-, $C_1$–$C_4$-alkylsulfinyl- or $C_1$–$C_4$-alkylsulfonyl-substituted alkyl having 1 to 6 carbon atoms, represents in each case optionally cyano-, carboxyl-, carbamoyl-, halogen- or $C_1$–$C_4$-alkoxy-carbonyl-substituted alkenyl or alkinyl having in each case 2 to 6 carbon atoms, or represents optionally cyano-, carboxyl-, carbamoyl-, halogen-, $C_1$–$C_4$-alkyl- or $C_1$–$C_4$-alkoxy-carbonyl-substituted cycloalkyl having 3 to 6 carbon atoms, $R^2$ represents hydrogen, cyano, carbamoyl, thiocarbamoyl, halogen, represents in each case optionally cyano-, halogen- or $C_1$–$C_4$-alkoxy-substituted alkyl, alkoxy or alkoxycarbonyl having in each case up to 6 carbon atoms, represents optionally halogen-substituted alkylthio having 1 to 6 carbon atoms, or represents optionally cyano-, halogen- or $C_1$–$C_4$-alkyl-substituted cycloalkyl having 3 to 6 carbon atoms, $R^3$ represents hydrogen, nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulfinyl- or $C_1$–$C_4$-alkylsulfonyl-substituted alkyl, alkoxy, alkylthio, alkylsulfinyl or alkylsulfonyl having in each case up to 4 carbon atoms in the alkyl groups, or represents alkylamino, dialkylamino or dialkylaminosulfonyl having in each case up to 4 carbon atoms in the alkyl groups, $R^4$ represents nitro, cyano, carboxyl, carbamoyl, thiocarbamoyl, halogen, represents in each case optionally halogen-, $C_1$–$C_4$-alkoxy-, $C_1$–$C_4$-alkylthio-, $C_1$–$C_4$-alkylsulfinyl- or $C_1$–$C_4$-alkylsulfonyl-substituted alkyl, alkoxy, alkylthio, alkylsulfinyl or alkylsulfonyl having in each case up to 4 carbon atoms in the alkyl groups, or represents alkylamino, dialkylamino or dialkylaminosulfonyl having in each case up to 4 carbon atoms in the alkyl groups, Y represents hydrogen, represents in each case optionally cyano-, carboxyl-, carbamoyl-, halogen- or $C_1$–$C_4$-alkoxycarbonyl-substituted alkyl, alkylcarbonyl or alkoxycarbonyl having in each case up to 6 carbon atoms, represents in each case optionally halogen-substituted alkylsulfonyl, alkylaminocarbonyl or dialkylaminocarbonyl having in each case up to 6 carbon atoms in the alkyl groups, represents in each case optionally cyano-, carboxyl-, carbamoyl-, halogen- or $C_1$–$C_4$-alkoxycarbonyl-substituted alkenyl, alkenylcarbonyl, alkinyl or alkinylcarbonyl having in each case 2 to 6 carbon atoms, represents optionally halogen-substituted alkenylsulfonyl having up to 6 carbon atoms represents in each case optionally cyano-, halogen- or $C_1$–$C_4$-alkyl-substituted cycloalkyl, cycloalkylcarbonyl or cycloalkylalkyl having in each case 3 to 6 carbon atoms in the cycloalkyl groups and optionally 1 to 3 carbon atoms in the alkyl moiety, or represents in each case optionally nitro-, cyano-, carboxyl-, carbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenylcarbonyl, phenylsulfonyl, phenyl-$C_1$–$C_4$-alkyl or phenylcarbonyl-$C_1$–$C_4$-alkyl, and Z represents one of the heterocyclic groupings below

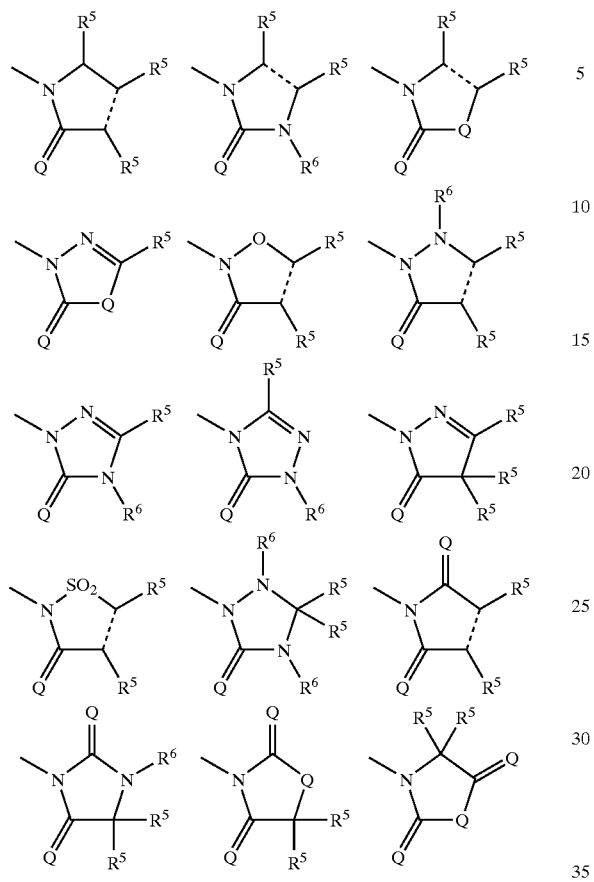

in which in each case the broken bond is a single bond or a double bond,

Q represents oxygen, $R^5$ represents hydrogen, hydroxyl, mercapto, cyano, halogen, represents in each case optionally cyano-, halogen-, $C_1$–$C_4$-alkoxy-, $C_1$–$C_4$-alkylthio-, $C_1$–$C_4$-alkylsulfinyl- or $C_1$–$C_4$-alkylsulfonyl-substituted alkyl, alkylcarbonyl, alkoxy, alkoxycarbonyl, alkylthio, alkylsulfinyl or alkylsulfonyl having in each case up to 6 carbon atoms in the alkyl groups, represents propadienylthio, represents in each case optionally halogen-substituted alkylamino or dialkylamino having in each case up to 6 carbon atoms in the alkyl groups, represents in each case optionally halogen-substituted alkenyl, alkinyl, alkenyloxy, alkenylthio or alkenylamino having in each case up to 6 carbon atoms in the alkenyl or alkinyl groups, represents in each case optionally halogen-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and optionally up to 4 carbon atoms in the alkyl moiety, represents in each case optionally halogen-, $C_1$–$C_4$-alkyl- or $C_1$–$C_4$-alkoxy-substituted phenyl, phenyloxy, phenylthio, phenylamino, benzyl, benzyloxy, benzylthio or benzylamino, represents pyrrolidino, piperidino or morpholino, or—if two adjacent radicals $R^5$ and $R^5$ are located on a double bond—together with the adjacent radical $R^5$ also represents a benzo grouping, and $R^6$ represents hydrogen, hydroxyl, amino, alkylideneamino having up to 4 carbon atoms, represents in each case optionally halogen- or $C_1$–$C_4$-alkoxy-substituted alkyl, alkoxy, alkylamino, dialkylamino or alkanoylamino having in each case up to 6 carbon atoms in the alkyl groups, represents in each case optionally halogen-substituted alkenyl, alkinyl or alkenyloxy having in each case up to 6 carbon atoms in the alkenyl or alkinyl groups, represents in each case optionally halogen-substituted cycloalkyl, cycloalkylalkyl or cycloalkylamino having in each case 3 to 6 carbon atoms in the cycloalkyl groups and optionally up to 3 carbon atoms in the alkyl moiety, or represents in each case optionally halogen-, $C_1$–$C_4$-alkyl- or $C_1$–$C_4$-alkoxy-substituted phenyl or benzyl, or together with an adjacent radical $R^5$ or $R^6$ represents optionally halogen- or $C_1$–$C_4$-alkyl-substituted alkanediyl having 3 to 5 carbon atoms, where the individual radicals $R^5$ and $R^6$—if a plurality of these are attached to the same heterocyclic groupings, may have identical or different meanings within the scope of the above definition.

2. The compound according to claim 1, wherein n represents the numbers 0 or 1,

A represents methylene, ethylidene or dimethylene, $R^1$ represents in each case optionally fluorine-, chlorine-, methoxy-, ethoxy-, n- or i-propoxy-, methylthio-, ethylthio-, n- or i-propylthio-, methylsulfinyl-, ethylsulfinyl-, n- or i-propylsulfinyl-, methylsulfonyl-, ethylsulfonyl-, n- or i-propylsulfonyl-substituted methyl, ethyl, n- or i-propyl, n-, i-, s- or t-butyl, represents in each case optionally fluorine-, chlorine- or bromine-substituted propenyl, butenyl, propinyl or butinyl, or represents in each case optionally cyano-, fluorine-, chlorine-, bromine-, methyl- or ethyl-substituted cyclopropyl, cyclobutyl, cyclopentyl or cyclohexyl, $R^2$ represents hydrogen, cyano, carbamoyl, thiocarbamoyl, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, methoxycarbonyl, ethoxycarbonyl, n- or i-propoxycarbonyl, represents in each case optionally fluorine- and/or chlorine-substituted methylthio, ethylthio, n- or i-propylthio, or represents in each case optionally cyano-, fluorine-, chlorine-, bromine-, methyl- or ethyl-substituted cyclopropyl, cyclobutyl, cyclopentyl or cyclohexyl, $R^3$ represents hydrogen, nitro, cyano, carboxyl, carbamoyl, thiocarbamoyl, fluorine, chlorine, bromine, iodine, represents in each case optionally fluorine- and/or chlorine-, methoxy-, ethoxy-, n- or i-propoxy-, methylthio-, ethylthio-, n- or i-propylthio-, methylsulfinyl-, ethylsulfinyl-, methylsulfonyl- or ethylsulfonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulfinyl, ethylsulfinyl, n- or i-propylsulfinyl, methylsulfonyl, ethylsulfonyl, n- or i-propylsulfonyl, or represents methylamino, ethylamino, n- or i-propylamino, dimethylamino, diethylamino, dimethylaminosulfonyl or diethyiaminosulfonyl,

151

R⁴ represents nitro, cyano, carboxyl, carbamoyl, thiocarbamoyl, fluorine, chlorine, bromine, represents in each case optionally fluorine- and/or chlorine-, methoxy-, ethoxy-, n- or i-propoxy-, methylthio-, ethylthio-, n- or i-propylthio-, methylsulfinyl-, ethylsulfinyl-, methylsulfonyl- or ethylsulfonyl-substituted methyl, ethyl, n- or i-propyl, n-, i-, s- or t-butyl, represents in each case optionally fluorine- and/or chlorine-, methoxy-, ethoxy-, n- or i-propoxy-substituted methoxy, ethoxy, n- or i-propoxy, represents in each case optionally fluorine- and/or chlorine-substituted methylthio, ethylthio, n- or i-propylthio, methylsulfinyl, ethylsulfinyl, n- or i-propylsulfinyl, methylsulfonyl, ethylsulfonyl, n- or i-propylsulfonyl, or represents methylamino, ethylamino, n- or i-propylamino, dimethylamino, diethylamino, dimethylaminosulfonyl or diethylaminosulfonyl, R⁵ represents hydrogen, hydroxyl, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, fluoroethyl, chloroethyl, difluoroethyl, dichloroethyl, fluoro-n-propyl, fluoro-i-propyl, chloro-n-propyl, chloro-i-propyl, methoxymethyl, ethoxymethyl, methoxyethyl, ethoxyethyl, methoxy, ethoxy, n- or i-propoxy, n-, i-, s- or t-butoxy, fluoroethoxy, chloroethoxy, difluoroethoxy, dichloroethoxy, trifluoroethoxy, trichloroethoxy, chlorofluoroethoxy, chlorodifluoroethoxy, fluorodichloroethoxy, methylthio, ethylthio, n- or i-propylthio, fluoroethylthio, chloroethylthio, difluoroethylthio, dichloroethylthio, chlorofluoroethylthio, chlorodifluoroethylthio, fluorodichloroethylthio, methylsulfinyl, ethylsulfinyl, n- or i-propylsulfinyl, methylsulfonyl, ethylsulfonyl, n- or i-propylsulfonyl, dimethylamino, propenylthio, butenylthio, propinylthio, butinylthio, cyclopropyl, cyclopropylmethyl cyclopropylmethoxy, phenyl or phenoxy, R⁶ represents amino, methyl, ethyl, n- or i-propyl, n-, i-, s- or t-butyl, methoxy, ethoxy, methylamino, dimethylamino, cyclopropyl or cyclopropylmethyl, or together with R⁵ represents propane-1,3-diyl (trimethylene), butane-1,4-diyl(tetramethylene) or pentane-1,5diyl(pentamethylene), and Y represents hydrogen, represents in each case optionally cyano-, fluorine-, chlorine-, methoxy- or ethoxy-substituted methyl, ethyl, n- or i-propyl, acetyl, propionyl, n- or i-butyroyl, methoxycarbonyl or ethoxycarbonyl, represents in each case optionally fluorine-, chlorine- and/or bromine-substituted methylsulfonyl-, ethylsulfonyl-, n- or i-propylsulfonyl-, n-, i-, s- or t-butylsulfonyl-, methylaminocarbonyl, ethylaminocarbonyl, n- or i-propylaminocarbonyl, dimethylaminocarbonyl or diethylaminocarbonyl, represents in each case optionally fluorine-, chlorine- or bromine-substituted propenyl, butenyl, propenylcarbonyl, butenylcarbonyl, propenylsulfonyl, butenylsulfonyl, propinyl, butinyl, propinylcarbonyl or butinylcarbonyl, represents in each case optionally cyano-, fluorine-, chlorine-, methyl- or ethyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropylmethyl, cyclobutylmethyl, cyclopentylmethyl or cyclohexylmethyl, or represents in each case optionally nitro-, cyano-, fluorine-, chlorine-, bromine-,

152 methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenylcarbonyl, phenylsulfonyl, benzyl or phenylcarbonylmethyl.

3. The compound according to claim 1, wherein Z represents the grouping below

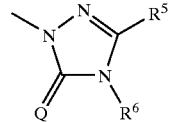

4. The compound according to claim 1, wherein n represents 0.

5. A process for preparing a compound according to claim 1, comprising:

(a) reacting a pyrazole of the formula (II)

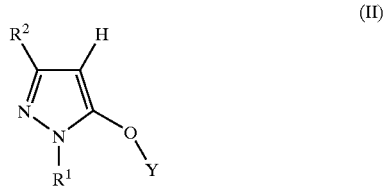

(II)

in which
R¹, R² and Y are as defined in claim 1, with
a substituted benzoic acid of the formula (III),

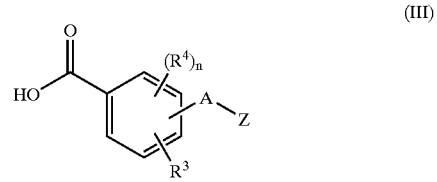

(III)

in which
n, A, R³, R⁴ and Z are as defined in claim 1, in the presence of a dehydrating agent, optionally in the presence of one or more reaction auxiliaries and optionally in the presence of a diluent, or (b) reacting a pyrazole of the formula (II)

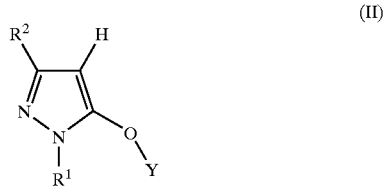

(II)

in which
R¹, R² and Y are as defined in claim 1, with
a member selected from the group consisting of a substituted benzoic acid derivative of the formula (IV)

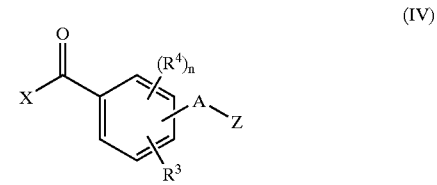

(IV)

in which n A, $R^3$, $R^4$ and Z are as defined in claim 1, and
X represents cyano, halogen or alkoxy,
and corresponding carboxylic anhydrides thereof
optionally in the presence of one or more reaction auxiliaries and optionally in the presence of a diluent, or (c) reacting a substituted benzoylpyrazole of the formula (Ia)

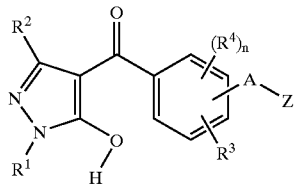

(Ia)

in which
n, A, $R^1$, $R^2$, $R^3$, $R^4$ and Z are as defined in claim 2,
with
a compound of the formula (V)

H—Y (V)

in which
Y is as defined in claim 2, except for hydrogen,
and optionally further comprising the step of including as a reactant corresponding isocyanates or isothiocyanates thereof
optionally in the presence of one or more reaction auxiliaries and optionally in the presence of a diluent,
and, optionally further comprising the step of subjecting the resulting compound of the formula (I) to one or more reactions selected from the group consisting of an electrophilic reaction, a nucleophilic reaction, an oxidation reaction, a reduction reaction and combinations thereof within the scope of the definition of the substituents, or further comprising the step of converting the compound of the formula (I) into a salt.

6. A compound of the formula (Ia)

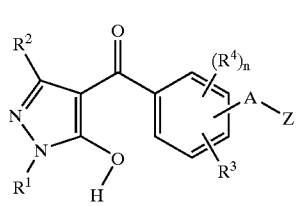

(Ia)

in which
n, A, $R^1$, $R^2$, $R^3$, $R^4$ and Z are as defined in claim 1.

7. An herbicidal composition comprising at least one compound according to claim 1 and an extender.

8. A method for controlling undesirable plants comprising the step of applying an herbicidally effective amount at least one compound according to claim 1 to a member selected from the group consisting of said plant and a habitat of said plant.

9. The compound of claim 1 wherein Z represents a member selected from the group consisting of

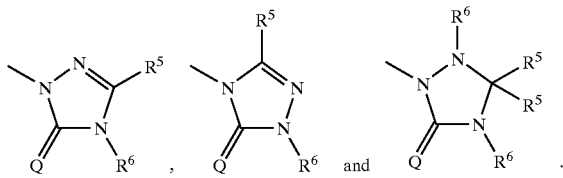

* * * * *